(12) United States Patent
Wang et al.

(10) Patent No.: US 7,968,305 B2
(45) Date of Patent: Jun. 28, 2011

(54) BIOCHIPS INCLUDING ION TRANSPORT DETECTING STRUCTURES AND METHODS OF USE

(75) Inventors: Xiaobo Wang, San Diego, CA (US); Lei Wu, San Diego, CA (US); Jun Quan Xu, Beijing (CN); Ming Xiang Huang, San Diego, CA (US); Weiping Yang, San Diego, CA (US); Jing Cheng, Beijing (CN); Jia Xu, San Diego, CA (US)

(73) Assignee: Aviva Biosciences Corporation, San Diego, CA (US)

( * ) Notice: Subject to any disclaimer, the term of this patent is extended or adjusted under 35 U.S.C. 154(b) by 1552 days.

(21) Appl. No.: 10/104,300

(22) Filed: Mar. 22, 2002

(65) Prior Publication Data

US 2002/0182627 A1    Dec. 5, 2002

Related U.S. Application Data

(60) Provisional application No. 60/311,327, filed on Aug. 10, 2001, provisional application No. 60/278,308, filed on Mar. 24, 2001.

(51) Int. Cl.
    *G01N 33/53*    (2006.01)
(52) U.S. Cl. .................................................. 435/7.2
(58) Field of Classification Search ............. 435/4, 7.2, 435/7.1, 5, 7.21, 7.22, 7.23, 7.24, 7.25, 7.3, 435/7.31, 7.32, 283.1, 284.1, 285.2, 286.5, 435/287.1, 287.2, 287.3, 288.4, 288.5, 288.7; 436/514; 422/50, 55, 58, 61, 62, 63
See application file for complete search history.

(56) References Cited

U.S. PATENT DOCUMENTS

| | | | |
|---|---|---|---|
| 3,364,087 A | 1/1968 | Solomon et al. | |
| 3,410,979 A | 11/1968 | Larson | |
| 4,055,799 A | 10/1977 | Coster et al. | |
| 4,160,645 A | 7/1979 | Ullman | |
| 4,275,149 A | 6/1981 | Litman et al. | |
| 4,318,980 A | 3/1982 | Boguslaski et al. | |
| 4,324,255 A | 4/1982 | Barach et al. | |
| 4,454,032 A * | 6/1984 | Dupont et al. ............... | 210/96.1 |
| 4,894,343 A | 1/1990 | Tanaka et al. | |
| 4,894,443 A | 1/1990 | Greenfield et al. | |
| 5,079,169 A | 1/1992 | Chu et al. | |
| 5,364,744 A | 11/1994 | Buican et al. | |
| 5,389,215 A | 2/1995 | Horiuchi et al. | |
| 5,422,272 A | 6/1995 | Papp et al. | |
| 5,506,141 A | 4/1996 | Weinreb et al. | |
| 5,585,277 A | 12/1996 | Bowie et al. | |
| 5,612,474 A | 3/1997 | Patel | |
| 5,653,939 A | 8/1997 | Hollis et al. | |
| 5,661,035 A | 8/1997 | Tsien et al. | |
| 5,679,582 A | 10/1997 | Bowie et al. | |
| 5,795,457 A | 8/1998 | Pethig et al. | |
| 5,840,041 A | 11/1998 | Petter et al. | |
| 5,846,396 A | 12/1998 | Zanzucchi et al. | |
| 5,858,666 A | 1/1999 | Weiss | |
| 5,880,071 A | 3/1999 | Parce et al. | |
| 5,883,760 A | 3/1999 | Yamada et al. | |
| 5,932,485 A | 8/1999 | Schofield | |
| 5,948,684 A | 9/1999 | Weigl et al. | |
| 5,972,710 A | 10/1999 | Weigl et al. | |
| 5,981,268 A | 11/1999 | Kovacs | |
| 5,998,129 A | 12/1999 | Schutze et al. | |
| 6,063,260 A * | 5/2000 | Olesen et al. ................ | 205/793 |
| 6,071,702 A | 6/2000 | Yamamoto et al. | |
| 6,107,066 A | 8/2000 | Tsien et al. | |
| 6,117,291 A | 9/2000 | Olesen et al. | |
| 6,120,666 A | 9/2000 | Jacobson et al. | |
| 6,159,749 A | 12/2000 | Liu | |
| 6,171,865 B1 | 1/2001 | Weigl et al. | |
| 6,177,000 B1 | 1/2001 | Peterson | |
| 6,225,059 B1 | 5/2001 | Ackley et al. | |
| 6,251,691 B1 | 6/2001 | Seul | |
| 6,267,872 B1 | 7/2001 | Akeson et al. | |
| 6,284,113 B1 | 9/2001 | Bjornson et al. | |
| 6,284,459 B1 | 9/2001 | Nova et al. | |
| 6,315,940 B1 * | 11/2001 | Nisch et al. ................ | 435/287.1 |
| 6,352,853 B1 | 3/2002 | King et al. | |
| 6,355,491 B1 | 3/2002 | Zhou et al. | |
| 6,379,916 B1 | 4/2002 | Meyer | |
| 6,387,707 B1 | 5/2002 | Weigl et al. | |
| 6,416,642 B1 | 7/2002 | Alajoki et al. | |

(Continued)

FOREIGN PATENT DOCUMENTS

DE    196 53 659    5/1998

(Continued)

OTHER PUBLICATIONS

Wang and Li, Assay and Drug Devel. Technol. 1:1-13 (2003).
Xiao et al., Anal. Chem 74:1333-1339 (2002).
Mathes, DDT 8:1022-1024 (2003).
Almers et al., J. Physiol. 312:159-176 (1981).
Costa et al., Biophysical Journal 64:395-401 (1994).
Karnakis et al, Proc. SPIE 4443:150-158 (2001) Abstract.
Dunsky, Proc. SPIE 4443:135-149 (2001) Abstract.
Nishimae, Proc. SPIE 4088:209-211 (2000) Abstract.
Okada, Proc. SPIE 4088:148-153 (2000) Abstract.
Asada, Proc. SPIE 4088:132-135 (2000) Abstract.

(Continued)

*Primary Examiner* — Ann Y Lam
(74) *Attorney, Agent, or Firm* — Morrison & Foerster LLP

(57) ABSTRACT

The present invention recognizes that the determination of ion transport function or property using direct detection methods, such as patch-clamps, whole cell recording or single channel recording, are preferable to methods that utilize indirect detection methods, such as FRET based detection system. The present invention provides biochips and methods of use that allow for the direct analysis of ion transport function or property using microfabricated structures that can allow for automated detection of ion transport function or property. These biochips and methods of use thereof are particularly appropriate for automating the detection of ion transport function or property, particularly for screening purposes.

32 Claims, 24 Drawing Sheets

U.S. PATENT DOCUMENTS

| | | | |
|---|---|---|---|
| 6,448,794 B1 | 9/2002 | Cheng et al. | |
| 6,488,829 B1* | 12/2002 | Schroeder et al. | 204/403.01 |
| 6,572,830 B1* | 6/2003 | Burdon et al. | 422/186.29 |
| 6,596,143 B1 | 7/2003 | Wang et al. | |
| 6,610,188 B1 | 8/2003 | Fuhr et al. | |
| 6,699,697 B2 | 3/2004 | Klemic | |
| 6,758,961 B1* | 7/2004 | Vogel et al. | 205/777.5 |
| 6,766,817 B2 | 7/2004 | Da Silva | |
| 6,776,896 B1* | 8/2004 | Osipchuk | 205/777.5 |
| 6,936,462 B1 | 8/2005 | Owen | |
| 7,056,430 B1* | 6/2006 | Osipchuk et al. | 205/777.5 |
| 7,361,500 B2* | 4/2008 | Stett et al. | 435/285.2 |
| 7,462,324 B2* | 12/2008 | Ozaki et al. | 422/82.01 |
| 7,723,029 B2* | 5/2010 | Huang et al. | 435/6 |
| 2002/0006357 A1 | 1/2002 | McGeoch | |
| 2002/0014408 A1 | 2/2002 | Schroeder | |
| 2002/0022219 A1 | 2/2002 | Clements et al. | |
| 2002/0025573 A1 | 2/2002 | Maher et al. | |
| 2002/0053915 A1 | 5/2002 | Weaver et al. | |
| 2002/0064841 A1 | 5/2002 | Klemic et al. | |
| 2002/0086280 A1 | 7/2002 | Lynes | |
| 2002/0104757 A1 | 8/2002 | Schmidt | |
| 2002/0108869 A1 | 8/2002 | Savtchenko | |
| 2002/0123134 A1 | 9/2002 | Huang et al. | |
| 2002/0144905 A1 | 10/2002 | Schmidt et al. | |
| 2002/0146845 A1 | 10/2002 | Parce et al. | |
| 2002/0164777 A1 | 11/2002 | Kelly et al. | |
| 2002/0182627 A1 | 12/2002 | Wang et al. | |
| 2002/0195337 A1 | 12/2002 | Osipchuk et al. | |
| 2003/0031829 A1 | 2/2003 | Tanner et al. | |
| 2003/0052002 A1 | 3/2003 | Vogel et al. | |
| 2003/0098248 A1 | 5/2003 | Vogel et al. | |
| 2003/0146091 A1* | 8/2003 | Vogel et al. | 204/403.01 |
| 2004/0146849 A1* | 7/2004 | Huang et al. | 435/4 |
| 2005/0009004 A1* | 1/2005 | Xu et al. | 435/4 |

FOREIGN PATENT DOCUMENTS

| | | |
|---|---|---|
| DE | 197 44 649 | 4/1999 |
| DE | 199 36 302 | 2/2001 |
| EP | 0 816 837 | 1/1998 |
| EP | 1195432 A2 | 4/2002 |
| WO | WO 94/25862 | 10/1994 |
| WO | WO 96/13721 | 5/1996 |
| WO | WO-98/22819 | 5/1998 |
| WO | WO 98/50791 A1 | 11/1998 |
| WO | WO 99/19729 | 4/1999 |
| WO | 99/31503 | 6/1999 |
| WO | WO-99/38612 | 8/1999 |
| WO | WO 99/66329 | 12/1999 |
| WO | 00/25121 | 5/2000 |
| WO | WO-00/54882 | 9/2000 |
| WO | WO 00/54882 A1 | 9/2000 |
| WO | WO 00/71742 A2 | 11/2000 |
| WO | WO 01/25769 A2 | 4/2001 |
| WO | WO 01/25769 A3 | 4/2001 |
| WO | WO 01/27614 A1 | 4/2001 |
| WO | WO 01/34764 A2 | 5/2001 |
| WO | WO 01/48474 A1 | 7/2001 |
| WO | WO 01/59447 A1 | 8/2001 |
| WO | WO 01/69241 | 9/2001 |
| WO | WO 02/04943 A2 | 1/2002 |
| WO | WO 02/04943 A3 | 1/2002 |
| WO | WO 02/52045 | 1/2002 |
| WO | WO 02/12986 A1 | 2/2002 |
| WO | WO 02/16647 A1 | 2/2002 |
| WO | WO 02/24862 | 3/2002 |
| WO | WO 02/27909 A2 | 4/2002 |
| WO | WO 02/28523 A2 | 4/2002 |
| WO | WO 02/29400 | 4/2002 |
| WO | WO 02/29402 A2 | 4/2002 |
| WO | WO 02/29402 A3 | 4/2002 |
| WO | WO 02/30562 A1 | 4/2002 |
| WO | WO 02/31505 A1 | 4/2002 |
| WO | WO 02/31506 A1 | 4/2002 |
| WO | WO 02/42766 A2 | 5/2002 |
| WO | WO 02/42766 A3 | 5/2002 |
| WO | WO 02/059603 | 8/2002 |
| WO | WO 02/065092 A2 | 8/2002 |
| WO | WO 02/066596 | 8/2002 |
| WO | WO 02/075309 | 9/2002 |
| WO | WO 02/077259 | 10/2002 |
| WO | WO03/093494 | 11/2003 |

OTHER PUBLICATIONS

Knowles, Proc. SPIE 3888:210-216 (2000) Abstract.

Madou, Proc. SPIE 3877:44-53 (1999) Abstract.

Kreutz, Proc. SPIE 2879:37-44 (1996) Abstract.

Bard, F., et al., "Epitope and Isotype Specificities of Antibodies to β-Amyloid Peptide for Protection Against Alzheimer's Disease-Like Neuropathology", *Proc. Nat'l Acad. Sci. USA* 100(4), (Feb. 18, 2003), 2023-2028.

Bard, F., et al., "Peripherally Administered Antibodies Against Amyloid β-Peptide Enter the Central Nervous System and Reduce Pathology in a Mouse Model of Alzheimer Disease", *Natural Medicine* 6 (8), (Aug. 2000), 916-919.

Demattos, R. B., et al., "Brain to Plasma AmyLoid-β Efflux: A Measure of Brain Amyloid Burden in a Mouse Model of Alzheimer's Disease", *Science*, 295, (Mar. 22, 2002), 2264-2267.

Dodel, R., et al., "Human Antibodies Against Amyloid-β Peptide: A Potential Treatment of Alzheimer's Disease", *Annals of Neurology*, 52(2), (Aug. 2002), 253-256.

Dodel, R., et al., "Human Immunoglobulins for the Treatment of Alzheimer's Disease", *Aktuelle Neurologie*, (Abstract Only) (2003), 1 pg.

Dodel, R., et al., Intravenous Immunoglobulins Containing Antibodies Against β-Amyloid for the Treatment of Alzheimer's Disease, *Journal of Neurology, Neurosurgery, and Psychiatry*, 75, 75 (2004), 1472-1474.

Du, Y, et al., "Reduced Levels of Amyloid β-Peptide Antibody in Alzheimer Disease", *Neurology*, 57(5), (Sep. 11, 2001), 801-805.

Friedland, R P., et al., "Prospects for Noninvasive Imaging of Brain Amyloid β in Alzheimer's Disease", *Annals of the New York Academy of Sciences*, 903, (Apr. 2000), 123-128.

Hyman, B T., et al., "Autoantibodies to Amyloid-β and Alzheimer's Disease", *Annals of Neurology*, 49(6), (Jun. 2001), 808-810.

Kazatchkine, M. D., et al., "Immunomodulation of Autoimmune and Inflammatory Diseases With Intravenous Immune Globulin", *New England Journal of Medicine*, 345(10), (Sep. 6, 2001), 747-755.

Kountouris, D., "The Efficiency of Intravenous Immunoglobulin by Dementia Alzheimer Type Patients" (Abstract Only) *Abstract Book, 9th Congress of the International Psychogeriatric Association*, (1999), http://users.otenet.gr/~dkount/oldpage/ 56.htm, (Observed Mar. 2, 2004), 1 pg.

Ota, M., et al., "Immunological Study on Alzheimer's Disease Using Anti-β-Protein Monoclonal Antibodies" (with English Abstract), *Nippon Ronen lgakkai Zasshi*, 30(1), (Jan. 1993), 23-29.

Rosenberg, R N., et al., "Dominantly Inherited Dementia and Parkinsonism, With Non-Alzheimer Amyloid Plaques: a New Neurogenetic Disorder", *Annals of Neurology*, 25(2), (Feb. 1989), 152-158.

Weksler, M E., et al., "Patients With Alzheimer Disease Have Lower Levels of Serum Anti-Amyloid Peptide Antibodies Than Healthy Elderly Individuals", *Experimental Gerontology*, 37(7), (Jul. 2002), 943-948.

Yoshida, T, et al., "Amyloid Precursor Protein, A β and Amyloid-Associated Proteins Involved in Chloroquine Retinopathy in Rats—Immunopathological Studies.", *Brain Research*, 764(1-2), (Aug. 1, 1997), 283-288.

U. S. Appl. No. 60/164,128, filed Nov. 8, 1999, Schmidt.

U. S. Appl. No. 60/322,365, filed Sep. 14, 2000, Schmidt.

U. S. Appl. No. 60/233,800, filed Sep. 19, 2000, Schmidt.

U. S. Appl. No. 60/322,178, filed Sep. 13, 2001, Schmidt.

Lindner et al., Microelectronic Engineering 41/42: 75-78 (1998).

Vogler et al., Microelectronic Engineering 53: 149-152 (2000).

Gutmann et al., Pharma. Research 16: 402-407 (1999).

Luong et al., Anal. Chem. 73: 1844-1848 (2001).

Wegener et al., Exp. Cell Research 259:158-166 (2000).

Xiao et al., Anal. Chem. 74:5748-5753 (2002).

Xiao et al., Biotechnol. Prog. 19:1000-1005 (2003).

Schmidt et al., Angewandte Chemie. International Edition (2000) 39(3137):3137-3140.
Supplementary European Search Report for EP 02753879.2, mailed Oct. 1, 2008, 10 pages.
Office Action for Canadian Application No. 2,441,366, date mailed on Jul. 6, 2004.
Response to Office Action for Canadian Application No. 2,441,366, filed on Jan. 6, 2005.
Office Action for Canadian Application No. 2,441,366, date mailed on Dec. 18, 2006.
WO 99/31503 and Search Report, Jun. 24, 1999, PCT.
Nehr et al., Pflueger Arch., 375:219-278 (1978).
Liem et al., Neurosurgery, 36: 382-392 (1995).
Nehr and Sakman, Scientific American, 266:44-51 (1992).
Sakman and Nehr, Ann. Rev. Physiol., 46:455-472 (1984).
Cahalan and Nehr, Methods in Enzymology, 207:3-14 (1992).
Levis and Rae, Mehods in Enzymology, 207:14-66 (1992).
Armstrong and Gilly, Methods in Enzymology, 207:100-122 (1992).
Heinmann and Conti, Methods in Enzymology, 207:131-148 (1992).
Bean, Methods in Enzymology, 207:181-193 (1992).
Lester, Ann. Rev. Physiol., 53:477-496 (1991).
Hamill and McBride, Ann. Rev. Physiol., 59:621-637 (1997).
Bustamante and Verranda, Brazilian Journal.,31:333-354 (1998).
Martinez-Pardon and Ferrus, Current Topics in Developmental. Biol., 36:303-312 (1998).
Herness, Physiology and Behavior, 69:17-27 (2000).
Wang et al., IEEE Transaction on Industry Applications, 33(3):660-669 (1997).
Cheng et al., Nature Biotechnology, 16:541-546 (1998).
Markx et al., Microbiology, 140:585-591 (1994).
Huang and Pethig, Meas. Sci. Technol., 2:1142-1146 (1991).
Gascoyne et al., IEEE Transactions, 33(3):670-678 (1997).
De Gasperis et al., Biomedical Microdevices, 2:41-49 (1999).
Wang et al., Biochim. Biophys. Acta., 1243:185-194 (1995).
Wang et al., Biophys. J., 74:2689-2701 (1998).
Huang et al., Biophys J., 73:1118-1129 (1997).
Yang et al., Anal. Chem., 71(5):911-918 (1999).
Becker et al., Proc. Natl Acad. Sci. USA, 92:860-864 (1995).
Becker et al., J. Phys. D: Appl. Phys., 27:2659-2662 (1994).
Huang et al., J. Phys. D: Appl. Phys., 26:1528-1535 (1993).
Wang et al., J. Phys. D: Appl. Phys., 26:1278-1285 (1993).
Stephens et al., Bone Marrow Transplantation, 18:777-782 (1996).
Washizu et al., IEEE Trans Ind. Appl., 30:835-843 (1994).
Hughes et al., Biochim. Biophys. Acta., 1425:119-126 (1998).
Morgan et al., Biophys. J., 77:516-525 (1999).
Fuhr et al., Biochim. Biophys. Acta., 1108:215-233 (1992).
Washizu et al., IEEE Trans. Ind. Appl., 26:352-358 (1990).
Fiedler et al., Anal. Chem., 70:1909-1915 (1998).
Muller et al., Biosensors and Bioelectronics, 14:247-256 (1999).
Schnelle et al., Biochim. Biophys. Acta. 1157:127-140 (1993).
Morgan et al., J. Micromech. Microeng., 7:65-70 (1997).
Wang et al., Biophys. J., 72:1887-1899 (1997).
Batra et al., Molecular Immunol., 30:379-386 (1993).
Huston et al., Proc. Natl. Acad. Sci., USA, 85:5879-5883 (1998).
Whitlow et al., Protein Engineering, 6:989-995 (1993).
Newton et al., Biochemistry, 35:545-553 (1996).
Cumber et al., Bioconj. Chem., 3:397-401 (1992).
Ladurner et al., J. Mol. Biol., 273:330-337 (1997).
Ahn et al., J. Microelectromechanical systems, 5:151-158 (1996).
Liakopoulos et al., Transducers 97, pp. 484-488, presented in 1997 international conference on solid state sensors and actuators, Chicago, Jun. 16, 1997.
Safarik and Safarikova, J. Chromotography, 722(B):33-53 (1999).
Fuhr et al., Biochim. Biophys. Acta., 1269:221-232 (1995).
Course Description for MEM System taught by James Klemic.
Protein Chip Data Archive Archive-Yale Gershein Lab, http://entry.eng.yale.edu/genome/yeast/chip Mar. 13, 2001.
Zhu et al., Nature Genetics, 26:283-289 (2000).
About Axon Instruments (Axoclamp and Axopatch Series Microelectrode Amplifiers).
Axon Instruments, Inc. Press Release Apr. 17, 2001.
Micro Vacuum Ltd. A Surface Engineering Approach Towards the Development of Cell Based Biochips, www.microvacuum.com/research/memocs/meeting1/.
Aston-Jones and Siggins, www.acnp.org/GA/GN401000005/CH005.html.
Straub et al., Nature Biotechnology, 19:121-124 (2001).
Chun et al., IEEE, pp. 406-411 (1999).
Erbe et al., App. Phys. Lett., 77(19):3102-3104 (2000).
Tilke et al., Superlattices and Microstructures, 27(5/6):597-601 (2000).
Blick et al., Physics 6 E pp. 821-827 (2000).
Krommer et al., Europhys. Lett., 50(1):101-106 (2000).
Fertig et al., Appl. Phys. Lett., 77(8)1218-1220 (2000).
Islas and Sigworth, J. Gen. Physol., 117(1):69-68 (2001) (Abstract).
Presentation—Cambridge Healthtech Institutes HTT Expo (High-Throughput Technologies), Philadelphia Jun. 13, 2001.
Automated Patch-Clamp, CeNes Ltd. Homepage.
Vegel, Development of Bioassays for Odorant Molecule Analysis, www.ehrat.ch/topnano21/english/11e.html (Abstract).
Vegel, http://bioweb.psi.ch/abstracts.html (Abstract).
Axon Instruments Inc., Press Release Oct. 30, 2000.
Axon Instruments Inc., Press Release May 25, 2000.
Axon Instruments, Inc., Press Release Aug. 29, 2000.
Patch Clamp—Method of Choice for Receptor Analysis, www.cytion.com/principe.htm.
Summary of Projects in the Laboratory of Dr. Albert Folch.
Liu et al., J. Chromotogr., 891(1):149-156 (2000) (Abstract).
Niwa et al., Anal. Chem., 72(5):949-955 (2000) (Abstract).
Niwa et al., Anal. Chem., 68(11):18650-1870 (1996) (Abstract).
Ryttsen, et al., Biophys. J., 79(4):1993-2001 (2000) (Abstract).
Chiu et al., Science, 283(5409):1892-1895 (Abstract), (1999).
Jardemark et al., Anal. Chem., 70(13):2468-1474 (Abstract), (1998).

* cited by examiner

✱ The measurement of device (63) optionally is not within the substrate (10).

✱ The electrode (60) can be positioned in either configuration.

⊛ Signal source can be AC or DC.
Typically, the signal source is integral to the measuring device, but this is not a requirement.

| | |
|---|---|
| I | Viability Unit |
| II | Ion Transport Unit |
| III | Fluorescence Unit |
| IV | Proteomics Unit |
| V | Genomics Unit |
| VI | Separation of Particles |

BIOCHIPS INCLUDING ION TRANSPORT DETECTING STRUCTURES AND METHODS OF USE

This application claims benefit of priority to U.S. Provisional Patent Application No. 60/311,327 filed Aug. 10, 2001 entitled "Biochips including ion transport detecting structures and methods of use" naming Wang et al. as inventors which is incorporated herein by reference in its entirety and to U.S. Provisional Patent Application No. 60/278,308 filed Mar. 24, 2001 entitled "Biochips including ion transport detecting structures and methods of use" naming Wang et al. as inventors which is incorporated herein by reference in its entirety.

This application incorporates by reference the following applications in their entirety:

U.S. patent application No. 60/278,308 filed Mar. 26, 2001, entitled "Biochips Including Ion Transport Detecting Structures and Methods of Use" naming Wang et al. as inventors.

U.S. patent application Ser. No. 09/399,299 filed Sep. 17, 1999, entitled "Individually Addressable Micro-Electromagnetic Unit Array Chips" naming Zhou et al. as inventors, U.S. patent application Ser. No. 09/685,410 filed Oct. 10, 2000, entitled "Individually Addressable Micro-Electromagnetic Unit Array Chips in Horizontal Configurations" naming Wu et al. as inventors, PCT application number WO/00/54882 published Sep. 21, 2000, entitled "Individually Addressable Micro-Electromagnetic Unit Array Chips" naming Zhou et al as inventors, U.S. patent application Ser. No. 09/678,263 entitled "Apparatus for Switching and Manipulating Particles and Methods of Use Thereof" filed on Oct. 3, 2000 and naming as inventors Xiaobo Wang, Weiping Yang, Junquan Xu, Jing Cheng, and Lei Wu;

U.S. patent application Ser. No. 09/643,362 entitled "Apparatus and Method for High Throughput Electrorotation Analysis" filed on Aug. 22, 2000, naming as inventors Jing Cheng, Junquan Xu, Xiaosan Zhu, Litian Liu, Xiaobo Wang and Lei Wu, and U.S. patent application Ser. No. 09/679,024 entitled "Apparatuses Containing Multiple Active Force Generating Elements and Uses Thereof" filed Oct. 4, 2000, and naming as inventors Xiaobo Wang, Jing Cheng, Lei Wu, Junquan Xu, and Weiping Yang.

U.S. patent application No. 60/239,299, filed Oct. 10, 2000, entitled "An Integrated Biochip System for Sample Preparation and Analysis" and naming as inventors Jing Cheng, Xiaobo Wang, Lei Wu, Weiping Yang and Junquan Xu.

The following applications are also incorporated herein by reference in their entirety:

U.S. patent application Ser. No. 09/636,104 filed Aug. 10, 2000, entitled "Methods for Manipulating Moieties in Microfluidic Systems", and to People's Republic of China Patent Application 00122631.2, filed Aug. 8, 2000, and to PCT Patent Application Number PCT/US00/25381 entitled "Method for Manipulating Moieties in Microfluidic Systems" filed Sep. 15, 2000, and naming Xiaobo Wang, Lei Wu, Jing Cheng, Weiping Yang, and Junquan Yu as inventors, all herein incorporated by reference in their entireties.

U.S. patent application Ser. No. 09/399,299 filed Sep. 17, 1999, entitled, "Individually Addressable Micro-Electromagnetic Unit Array Chips"; and to People's Republic of China Application Number 99104113.5, entitled "Individually Addressable Micro-Electromagnetic Unit Array Chips, Electromagnetic Biochips, and Their Applications", filed Mar. 15, 1999; and PCT Application Number PCT/US99/21417, filed Sep. 17, 1999, entitled "Individually Addressable Micro-Electromagnetic Unit Array Chips"; all of which are herein incorporated by reference in their entireties.

U.S. patent application Ser. No. 09/648,081 entitled "Methods and Compositions for Identifying Nucleic Acid Molecules Using Nucleolytic Activities and Hybridization" naming as inventors Guoqing Wang, Lei Wu, Xiaobo Wang, Jing Cheng, and WeiPing Yang, and filed on Aug. 25, 2000.

U.S. Patent Application No. 60/258,281 entitled "Active and Biocompatible Platforms Prepared by Polymerization of Surface Coating Films" naming as inventors Huang, Wang, Wu, Yang and Cheng, and filed on Dec. 26, 2000.

U.S. patent application Ser. No. 09/679,023 entitled "Apparatuses and Methods for Field Flow Fractionation of Particles Using Acoustic and Other Forces" naming as inventors Wang, Cheng, Wu and Xu, and filed on (TO BE DETERMINED).

U.S. patent application Ser. No. 09/686,737 entitled "Compositions and Methods for Separation of Moieties on Chips" naming as inventors Xu, Wang, Cheng, Yang and Wu, and filed on (TO BE DETERMINED).

TECHNICAL FIELD

The present invention relates generally to the field of ion transport detection systems and methods, particularly those that relate to the use of biochip technologies. Such biochip technologies can include micromanipulation methods to direct particles, such as cells, to areas on a biochip that have ion transport detection or measuring structures.

BACKGROUND

Ion transports are located within cellular membranes and regulate the flow of ions across the membrane. Ion transports participate in diverse processes, such as generating and timing of action potentials, synaptic transmission, secretion of hormones, contraction of muscles etc. Ion transports are popular candidates for drug discovery, and many known drugs exert their effects via modulation of ion transport functions or properties. For example, antiepileptic compounds such as phenytoin and lamotrigine which block voltage dependent sodium ion transports in the brain, anti-hypertension drugs such as nifedipine and diltiazem which block voltage dependent calcium ion transports in smooth muscle cells, and stimulators of insulin release such as glibenclamide and tolbutamine which block an ATP regulated potassium ion transport in the pancreas.

One popular method of measuring ion transport function or property is the patch-clamp method, which was first reported by Neher, Sakmann and Steinback (Pflueger Arch. 375:219-278 (1978)). This first report of the patch clamp method relied on pressing a glass pipette containing acetylcholine (Ach) against the surface of a muscle cell membrane, where discrete jumps in electrical current were attributable to the opening and closing of Ach-activated ion transports.

The method was refined by fire polishing the glass pipettes and applying gentle suction to the interior of the pipette when contact was made with the surface of the cell. Seals of very high resistance (between about 1 and about 100 giga ohms) could be obtained. This advancement allowed the patch clamp method to be suitable over voltage ranges which ion transport studies can routinely be made.

A variety of patch clamp methods have been developed, such as whole cell, vesicle, outside-out and inside-out patches (Liem et al., Neurosurgery 36:382-392 (1995)). Additional methods include whole cell patch clamp recordings, pressure patch clamp methods, cell free ion transport recording, perfusion patch pipettes, concentration patch clamp methods, perforated patch clamp methods, loose patch voltage clamp methods, patch clamp recording and patch clamp methods in tissue samples such as muscle or brain (Boulton et al, Patch-Clamp Applications and Protocols, Neuromethods V. 26 (1995), Humana Press, New Jersey).

These and later methods relied upon interrogating one sample at a time using large laboratory apparatus that require a high degree of operator skill and time. Attempts have been made to automate patch clamp methods, but these have met with little success. Alternatives to patch clamp methods have been developed using fluorescent probes, such as cumarin-lipids (cu-lipids) (Tsien et al., U.S. Pat. No. 6,107,066, issued August 2000). These methods rely upon change in polarity of membranes and the resulting motion of cu-lipids across the membrane. This motion allows for detection using fluorescence resonance energy transfer (FRET). Unfortunately, these methods do not measure ion transport directly but measure the change of indirect parameters as a result of ionic flux. For example, the characteristics of the lipid used in the cu-lipid can alter the biological and physical characteristics of the membrane, such as fluidity and polarizability.

Thus, what is needed is a simple device and method to measure ion transport directly. Preferably, these devices would utilize patch clamp detection methods because these types of methods represent a gold standard in this field of study. The present invention provides these devices and methods particularly miniaturized devices and automated methods for the screening of chemicals or other moieties for their ability to modulate ion transport function or property.

BRIEF DESCRIPTION OF THE FIGURES

FIG. 1A depicts a biochip of the present invention optionally with a coating. FIG. 1B depicts a cross section of FIG. 1A along A-A showing the coating in place. FIG. 1C depicts a biochip not having a coating.

FIG. 2A depicts the biochip of FIG. 1A with a cell (22) engaged thereto. FIG. 2B depicts a substrate (10) with a coating (14), wherein the substrate has been machined or etched to form a funnel shaped structure (20) continuous with a hole in the substrate (10). This funnel shaped structure (20) allows for less rigorous manufacturing parameters as compared to the straight walled holes (12) depicted in FIG. 2A. A cell (24) is depicted engaged on the structure of FIG. 2B. FIG. 2C depicts the structure of FIG. 2B inverted with a cell (24) engaged thereto. FIG. 2D depicts a structure having a double funnel structure (20, 22) that defines a hole (12) in the substrate (10). FIG. 2E depicts a substrate (10) with a smaller hole (12) with a funnel structure (20) engaged with a cell (24) with electrodes (60, 61) placed in a trans-like configuration. Although holes of particular shapes and dimensions are depicted, the holes can be of any appropriate shape or dimensions. Shapes of holes can be geometric or non-geometric, such as circular, oval, square, triangular, pentagonal, hexagonal, heptagonal, octagonal or the like. Non-geometrical shapes such as kidney bead or other shapes are also appropriate. Geometric shapes can have the advantage of allowing higher density packing of holes, such as in a honeycomb configuration. The diameter or cross section of the holes at the portion where a particle is contacted can be of any appropriate size, but is preferably between about 0.1 micrometer and about 100 micrometers, more preferably between about 1 micrometer and about 10 micrometers.

FIG. 3 depicts a variety of particle positioning means provided on a biochip of the present invention. The particle positioning means can be provided on the surface of the substrate, coated by a coating or be imbedded within the substrate. FIG. 3B depicts a spiral electrode structure (34), circular in nature, that is useful for positioning particles (35) at or near a hole (12, 16) wherein the depicted electrical connection leads (37) are operably engaged with an electrical signal source (32). The number of spiral electrode structures is preferably three or more, and more preferably between about three and about ten. The electrodes structures are preferably parallel at the tangent. FIG. 3C depicts a concentric electrode structure (36), circular in nature, that is useful for positioning particles (35) at or near a hole (12, 16) wherein the depicted electrical connection leads (37) are operably engaged with an electrical signal source (32). FIG. 3D depicts a square electrode structure (38), square in nature, that is useful for positioning particles (35) at or near a hole (12, 16) wherein the depicted electrical connection leads (37) are operably engaged with an electrical signal source (32). FIG. 3E depicts an electromagnetic electrode (31), that is useful for positioning particles (35) having bound thereto a magnetic moiety (39) at or near a hole (12, 16) wherein the depicted electrical connection leads (37) are operably engaged with an electrical signal source (32). FIG. 3F depicts a traveling wave dielectrophoresis structure (33), that is useful for positioning particles (35) at or near a hole (12, 16) wherein the depicted electrical connection leads (37) are operably engaged with an electrical signal source (32).

FIG. 5A depicts such a structure with a coating (50) over all surfaces. The coating can be made of appropriate materials, such as polymers or functional coatings that can allow for immobilization of materials such as biological moieties or chemical moieties. The coating can also include binding members, such as specific binding members, such as antibodies, that can facilitate the localization or immobilization of particles such as cells at or near the hole (12). In one aspect of the present invention, the coating is made of a polymer that has the characteristic of changing size with temperature. By increasing in size, the polymer can promote the formation of an efficient seal between a particle (24) such as a cell and the hole. In FIG. 5B the coating (52) is depicted as being localized to an area in close proximity to the hole (12) in the substrate. In one aspect of the present invention, the coating in this configuration includes specific binding members present on particles such as cells. In FIG. 5C the coating is depicted as being localized to the hole (12) and optionally surrounding areas. This configuration can promote a strong seal between the cell and the hole (12). In one aspect of the present invention, the substrate (10) is made of silicon. The substrate (10) is then heated to make a structure that includes the substrate (10) of silicon and a coating (50) of silicon dioxide. FIG. 5D depicts one aspect of the present invention where the coating (56) is localized in the hole and the surrounding areas on the bottom of the substrate (10). The coating (56) is of material, such as detergent or lipid binding proteins, preferably provided in a matrix such as polymer matrix that can dissolve or weaken membrane lipids or structure. As an example, use of this device to measure ion transport function or properties in eukaryotic cells such as mammalian cells, a cell is pushed into a hole (12) to achieve appropriate electric sealing between the cell membrane and the hole. When membrane patch of the cell is pushed or pulled down into the hole to be in contact with the coating (56) the lipid molecules in the membrane that are in contact or in close proximity with the coating (56) will dissolve or weaken by action of the coating (56). As a result, the membrane patch breaks off or is otherwise removed from the cell. This coating (56) serves as a means to rupture a membrane patch for certain whole cell ion transport assay methods.

FIG. 6B is viewed from the top of FIG. 6A, similar structures can be provided as electrodes (61) as viewed from the bottom of FIG. 6B. The electrodes (61) can be provided in or outside of the funnel structure (22) when present.

In FIG. 9A, a particle (24) such as a cell is engaged with the protrusions or wires (80). This is preferably accomplished by applying a positive or negative force, such as depicted in FIG. 7. The particle, such as a cell, is ruptured, such as through a pulse of force, to form a whole cell configuration. As depicted in FIG. 9B, the electrical connection leads (62) from the electrodes (60, 61) connect to a measuring device (63) that can monitor and optionally record the electric properties in the circuit completed as depicted by the dashed line.

FIG. 16 depicts the manufacture and use of needle structures for ion transport function or transport determinations.

FIG. 18 depicts chambers (190) being formed by a top channel (192) and a bottom channel (194) that can be made using appropriate methods such as etching, machining or polymerization. The channels are preferably closed, but can also be in an open configuration, in particular the top channel (192). The channels are separated by a barrier (196) and are preferably provided on a substrate (198). Particle positioning means (191) can be present to guide a particle, such as a cell (193), to an ion channel function detecting structure, such as an aperture (195).

SUMMARY

Figure 1:
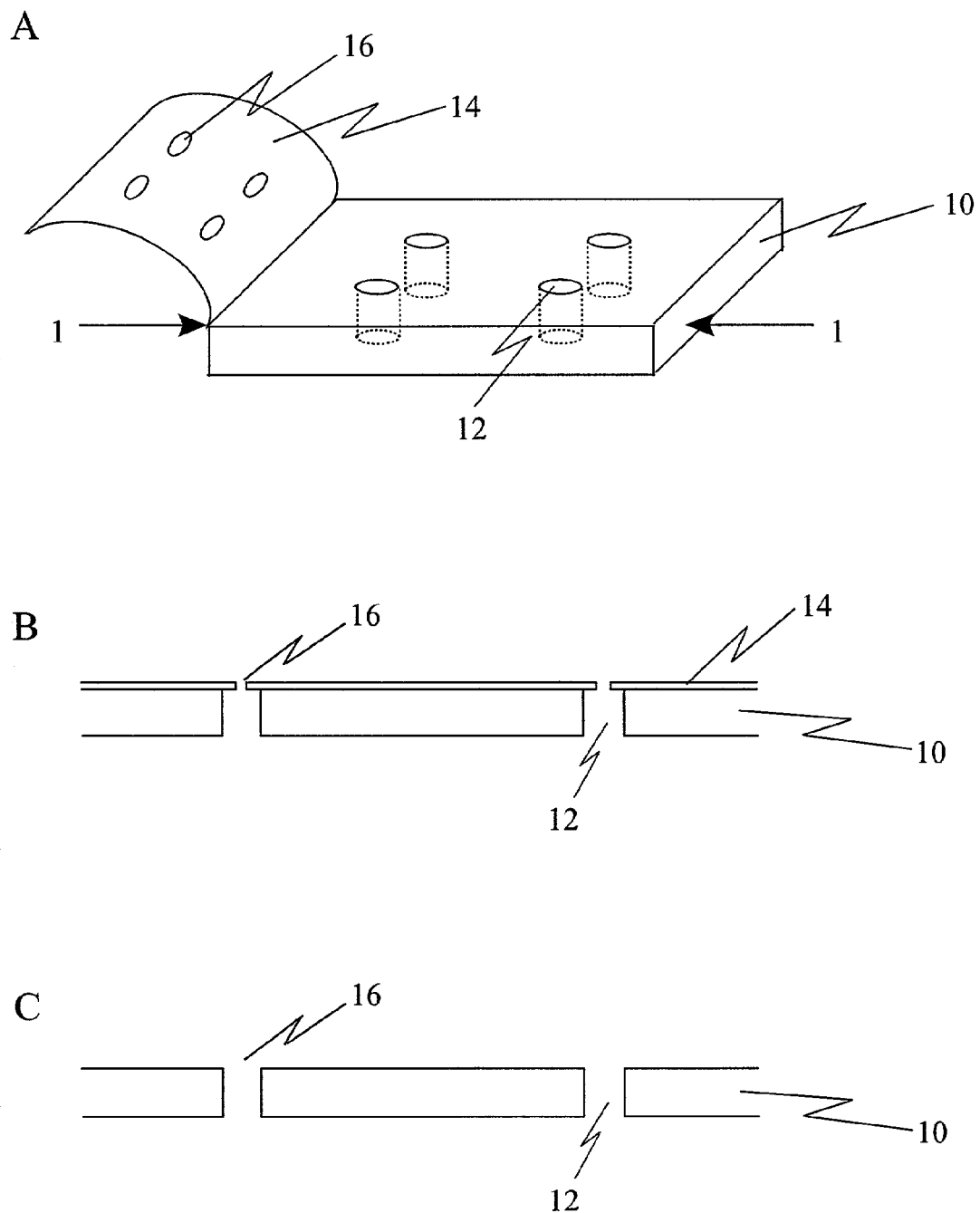
FIG. 1A, FIG. 1B and FIG. 1C depict one aspect of a biochip of the present invention. A substrate (10) made of appropriate material, such as fused silica, glass, silica, $SiO_2$, silicon, plastics, polymers or a combination or combinations thereof can define holes (12) that form at least in part ion transport measuring means of the present invention. Optionally, a coating (14) such as a polymer coating can be placed on top of the surface of the substrate. The coating can include functional groups to aid in the localization and immobilization particles at or near the holes (12). Such functional groups can include, for example, specific binding members that can facilitate such localization or immobilization of particles. The coating can also define holes (16) that can functionally engage the holes (16) defined by the substrate (10). In one aspect of the present invention, such holes (12) in the coating (14) are preferable because the accuracy and precision for machining or molding such holes in the coating is better suited for the coating (14) rather than the substrate (10). For example, it is more efficient, accurate and precise to manufacture holes in the thin coating (14) rather than the relatively thick substrate (10). This is particularly true when the coating (14) is made of polymers whereas the substrate (10) is made of harder materials that may be less suitable for machining, etching or molding, such as silica.

The present invention recognizes that the determination of ion transport function or property using direct detection methods, such as patch-clamp, whole cell recording or single channel recording, are preferable to methods that utilize indirect detection methods, such as fluorescence-based detection systems. The present invention provides biochips and methods of use that allow for the direct analysis of ion transport function or property using microfabricated structures that can allow for automated detection of ion transport functions or properties. These biochips and methods of use thereof are particularly appropriate for automating the detection of ion transport function or property, particularly for screening purposes.

A first aspect of the present invention is a biochip cell positioning device and methods of use. The biochip preferably includes particle positioning means and ion transport measuring means. The particle positioning means are preferably active upon cells such as eukaryotic cells using appropriate forces, particularly dielectric forces. The ion transport measuring means can be any appropriate, such as but not limited to patch clamp detection means, whole cell detection means, single ion transport detection means and the like.

A second aspect of the present invention is an array of capillaries on a biochip and methods of use. The array of capillaries is preferably microfabricated and integrated onto the chip such that they are useful in ion transport determinations. In one aspect of the present invention, the capillaries can be used as the basis of patch clamp assay methods, whole cell assay methods or single channel assay methods.

A third aspect of the invention is an array of needle electrodes on a biochip and methods of use. The array of needle electrodes is preferably microfabricated such that they are useful in ion transport determinations. These structures are particularly useful in ion transport determinations using whole cells.

A fourth aspect of the invention is an array of holes on a biochip and methods of use. The holes are preferably microfabricated and are useful as part of methods for the determination of ion transport function or property. The holes can be used in patch clamp methods such as whole cell or single ion channel methods. In one aspect of the present invention, the holes can be used in whole cell or single ion channel methods, particularly when negative pressure is applied upon a solution through such holes.

A fifth aspect of the invention is a biochip having ion transport detection structures being "detection channels" with appropriate geometries and dimensions, which are located along the side walls of other microfluidic channels, and methods of use. This type of patch-clamp-in-a-channel technology provides means of efficient simultaneous recording on and fluid delivery to a chip of current invention.

A sixth aspect of the invention is a biochip with ion transport detection structure combined with high information content screening and methods of use. This type of on-chip procedural combination allows for high throughput detection of multiple cellular signals in a time and space-controlled manner that cannot be achieved by existing technologies.

A seventh aspect of the invention is a biochip with three-dimensionally configured channels that can be microfabricated using sacrificial methodologies such as sacrificial wire methods and methods of use. This method provides an efficient procedure to microfabricate three-dimensional microfluidic structures that could be used for high-density bioassays and lab-on-a-chip systems.

The particle positioning means, particularly for positioning biological cells in an array format for single cell analysis, can be used with significant advantages for cell-based assays over current cell based assays. Current cell based assays analyze and examine a population of cells by measuring averaged, integrated signals and do not allow for assays at the single cell level. The cell positioning means disclosed in this application provides the devices and methods for analyzing individual cellular events in high throughput events. These analyses could be performed by reading out electrical (for example, ion transport assay) and optical signals (for example, fluorescent readout) from individual cells. With the high throughput capability for ion transport assay in this application, one could begin to analyze the intracellular signaling events on ion transporter functions or properties in a systematic fashion. That is the high throughput proteomics and functional analysis of ion channels at the single cell level. Furthermore, the devices and methods in the present invention allow the electrophysiology measurement of native cells isolated from tissues (normal or diseased). Such analysis would allow for a more accurate determination for cellular variation as hundreds or thousands of cells could be investigated individually for their biological, pharmacological and physiological responses. Cellular variation has proven to be a factor complicating the scientific analysis of complex systems, for example, in the diseases such as arrhythmias, cancer, and nervous system disorders. The present inventions provide devices and methods to address such cellular variations by providing single cell measurement.

In addition, positioning of the individual cells in an array format may permit better studies in subcellular organization and microdomain measurements. With the cells positioned, dynamic subcellular locations of cellular compartments, structures and molecules such as receptors and enzymes may be examined. Cells may be engineered to express recombinant ion channels or receptors with appropriate scaffolding proteins or chaperone proteins so that the surface expression of these proteins can be achieved at certain locations in a timed manner. For microdomain measurement of individual cells, various detection technologies such as imaging could be applied. Individual cells are positioned in an array format and the examination of hundreds even thousands of the cells could be performed in a single device for their chemical and biochemical parameters or properties in given subcellular microdomains. These parameters include, but not limited to, calcium, enzyme activity, translocation, membrane and molecular trafficking, pH, concentration of specific molecules.

DETAILED DESCRIPTION OF THE INVENTION

Definitions
Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Terms of orientation such as "up" and "down" or "upper" or "lower" and the like refer to orientation of parts during use of a device. Where a term is provided in the singular, the inventors also contemplate the plural of that term. The nomenclature used herein and the laboratory procedures described below are those well known and commonly employed in the art. Where there are discrepancies in terms and definitions used in references that are incorporated by reference, the terms used in this application shall have the definitions given herein. As employed throughout the disclosure, the following terms, unless otherwise indicated, shall be understood to have the following meanings:

"Dielectrophoresis" is the movement of polarized particles in electrical fields of nonuniform strength. There are generally two types of dielectrophoresis, positive dielectrophoresis and negative dielectrophoresis. In positive dielectrophoresis, particles are moved by dielectrophoretic forces toward the strong field regions. In negative dielectrophoresis, particles are moved by dielectrophoretic forces toward weak field regions. Whether moieties exhibit positive or negative dielectrophoresis depends on whether particles are more or less polarizable than the surrounding medium.

A "dielectrophoretic force" is the force that acts on a polarizable particle in an AC electrical field of non-uniform strength. The dielectrophoretic force $\vec{F}_{DEP}$ acting on a particle of radius r subjected to a non-uniform electrical field can be given, under the dipole approximation, by:

$$\vec{F}_{DEP} = 2\pi\varepsilon_m r^3 \chi_{DEP} \nabla E_{rms}^2$$

where $E_{rms}$ is the RMS value of the field strength, the symbol $\nabla$ is the symbol for gradient-operation, $\varepsilon_m$ is the dielectric permittivity of the medium, and $\chi_{DEP}$ is the particle polarization factor, given by:

$$\chi_{DEP} = \text{Re}\left(\frac{\varepsilon_p^* - \varepsilon_m^*}{\varepsilon_p^* + 2\varepsilon_m^*}\right).$$

"Re" refers to the real part of the "complex number". The symbol $\varepsilon_x^* = \varepsilon_x - j\sigma_x/2\pi f$ is the complex permittivity (of the particle x=p, and the medium x=m) and $j=\sqrt{-1}$. The parameters $\varepsilon_p$ and $\sigma_p$ are the effective permittivity and conductivity of the particle, respectively. These parameters may be frequency dependent. For example, a typical biological cell will have frequency dependent, effective conductivity and permittivity, at least, because of cytoplasm membrane polarization. Particles such as biological cells having different dielectric property (as defined by permittivity and conductivity) will experience different dielectrophoretic forces. The dielectrophoretic force in the above equation refers to the simple dipole approximation results. However, the dielectrophoretic force utilized in this application generally refers to the force generated by non-uniform electric fields and is not limited by the dipole simplification. The above equation for the dielectrophoretic force can also be written as $$\vec{F}_{DEP} = 2\pi\varepsilon_m r^3 \chi_{DEP} V^2 \nabla p(x,y,z)$$

where p(x,y,z) is the square-field distribution for a unit-voltage excitation (Voltage V=1 V) on the electrodes, V is the applied voltage.

"Traveling-wave dielectrophoretic (TW-DEP) force" refers to the force that is generated on particles or molecules due to a traveling-wave electric field. An ideal traveling-wave field is characterized by the distribution of the phase values of AC electric field components, being a linear function of the position of the particle. In this case the traveling wave dielectrophoretic force $\vec{F}_{TW-DEP}$ on a particle of radius r subjected to a traveling wave electrical field $E=E\cos(2\pi(ft-z/\lambda_0))\vec{a}_x$ (i.e., a x-direction field is traveling along the z-direction) is given, again, under the dipole approximation, by $$\vec{F}_{TW-DEP} = -\frac{4\pi^2 \varepsilon_m}{\lambda_0} r^3 \zeta_{TW-DEP} E^2 \cdot \vec{a}_z$$

where E is the magnitude of the field strength, $\varepsilon_m$ is the dielectric permittivity of the medium. $\zeta_{TW-DEP}$ is the particle polarization factor, given by $$\zeta_{TW-DEP} = \text{Im}\left(\frac{\varepsilon_p^* - \varepsilon_m^*}{\varepsilon_p^* + 2\varepsilon_m^*}\right).$$

"Im" refers to the imaginary part of the "complex number". The symbol $\varepsilon_x^* = \varepsilon_x - j\sigma_x/2\pi f$ is the complex permittivity (of the particle x=p, and the medium x=m). The parameters $\varepsilon_p$ and $\varepsilon_p$ are the effective permittivity and conductivity of the particle, respectively. These parameters may be frequency dependent.

A traveling wave electric field can be established by applying appropriate AC signals to the microelectrodes appropriately arranged on a chip. For generating a traveling-wave-electric field, it is necessary to apply at least three types of electrical signals each having a different phase value. An example to produce a traveling wave electric field is to use four phase-quardrature signals (0, 90, 180 and 270 degrees) to energize four linear, parallel electrodes patterned on the chip surfaces. Such four electrodes may be used to form a basic, repeating unit. Depending on the applications, there may be more than two such units that are located next to each other. This will produce a traveling-electric field in the spaces above or near the electrodes. As long as electrode elements are arranged following certain spatially sequential orders, applying phase-sequenced signals will result in establishing traveling electrical fields in the region close to the electrodes.

"Electric field pattern" refers to the field distribution in space or in a region of interest. An electric field pattern is determined by many parameters, including the frequency of the field, the magnitude of the field, the magnitude distribution of the field, and the distribution of the phase values of the field components, the geometry of the electrode structures that produce the electric field, and the frequency and/or magnitude modulation of the field.

"Dielectric properties" of a particle are properties that determine, at least in part, the response of a particle to an electric field. The dielectric properties of a particle include the effective electric conductivity of a particle and the effective electric permittivity of a particle. For a particle of homogeneous composition, for example, a polystyrene bead, the effective conductivity and effective permittivity are independent of the frequency of the electric field at least for a wide frequency range (e.g. between 1 Hz to 100 MHz). Particles that have a homogeneous bulk composition may have net surface charges. When such charged particles are suspended in a medium, electrical double layers may form at the particle/ medium interfaces. Externally applied electric field may interact with the electrical double layers, causing changes in the effective conductivity and effective permittivity of the particles. The interactions between the applied field and the electrical double layers are generally frequency dependent. Thus, the effective conductivity and effective permittivity of such particles may be frequency dependent. For moieties of nonhomogeneous composition, for example, a cell, the effective conductivity and effective permittivity are values that take into account the effective conductivities and effective permittivities of both the membrane and internal portion of the cell, and can vary with the frequency of the electric field. In addition, the dielectrophoretic force experience by a particle in an electric field is dependent on its size; therefore, the overall size of particle is herein considered to be a dielectric property of a particle. Properties of a particle that contribute to its dielectric properties include but are not limited to the net charge on a particle; the composition of a particle (including the distribution of chemical groups or moieties on, within, or throughout a particle); size of a particle; surface configuration of a particle; surface charge of a particle; and the conformation of a particle. Particles can be of any appropriate shape, such as geometric or non-geometric shapes. For example, particles can be spheres, non-spherical, rough, smooth, have sharp edges, be square, oblong or the like.

"Magnetic forces" refer to the forces acting on a particle due to the application of a magnetic field. In general, particles have to be magnetic or paramagnetic when sufficient magnetic forces are needed to manipulate particles. For a typical magnetic particle made of super-paramagnetic material, when the particle is subjected to a magnetic field $\vec{B}$, a magnetic dipole $\vec{\mu}$ is induced in the particle $$\vec{\mu} = V_p(\chi_p - \chi_m)\frac{\vec{B}}{\mu_m},$$
$$= V_p(\chi_p - \chi_m)\vec{H}_m$$

where $V_p$ is the particle volume, $\chi_p$ and $\chi_m$ are the volume susceptibility of the particle and its surrounding medium, $\mu_m$ is the magnetic permeability of medium, $\vec{H}_m$ is the magnetic field strength. The magnetic force $\vec{F}_{magnetic}$ acting on the particle is determined, under the dipole approximation, by the magnetic dipole moment and the magnetic field gradient:

$$\vec{F}_{magnetic} = -0.5V_p(\chi_p-\chi_m)\vec{H}_m \bullet \nabla \vec{B}_m,$$

where the symbols "●" and "∇" refer to dot-product and gradient operations, respectively. Whether there is magnetic force acting on a particle depends on the difference in the volume susceptibility between the particle and its surrounding medium. Typically, particles are suspended in a liquid, non-magnetic medium (the volume susceptibility is close to zero) thus it is necessary to utilize magnetic particles (its volume susceptibility is much larger than zero). The particle velocity $v_{particle}$ under the balance between magnetic force and viscous drag is given by:

$$v_{particle} = \frac{\vec{F}_{magnetic}}{6\pi r \eta_m}$$

where r is the particle radius and $\eta_m$ is the viscosity of the surrounding medium.

As used herein, "manipulation" refers to moving or processing of the particles, which results in one-, two- or three-dimensional movement of the particle, in a chip format, whether within a single chip or between or among multiple chips. Non-limiting examples of the manipulations include transportation, focusing, enrichment, concentration, aggregation, trapping, repulsion, levitation, separation, isolation or linear or other directed motion of the particles. For effective manipulation, the binding partner and the physical force used in the method should be compatible. For example, binding partner such as microparticles that can be bound with particles, having magnetic properties are preferably used with magnetic force. Similarly, binding partners having certain dielectric properties, for example, plastic particles, polystyrene microbeads, are preferably used with dielectrophoretic force.

A "sample" is any sample from which particles are to be separated or analyzed. A sample can be from any source, such as an organism, group of organisms from the same or different species, from the environment, such as from a body of water or from the soil, or from a food source or an industrial source. A sample can be an unprocessed or a processed sample. A sample can be a gas, a liquid, or a semi-solid, and can be a solution or a suspension. A sample can be an extract, for example a liquid extract of a soil or food sample, an extract of a throat or genital swab, or an extract of a fecal sample. Samples are can include cells or a population of cells. The population of cells can be a mixture of different cells or a population of the same cell or cell type, such as a clonal population of cells. Cells can be derived from a biological sample from a subject, such as a fluid, tissue or organ sample. In the case of tissues or organs, cells in tissues or organs can be isolated or separated from the structure of the tissue or organ using known methods, such as teasing, rinsing, washing, passing through a grating and treatment with proteases. Samples of any tissue or organ can be used, including mesodermally derived, endodermally derived or ectodermally derived cells. Particularly preferred types of cells are from the heart and blood. Cells include but are not limited to suspensions of cells, cultured cell lines, recombinant cells, infected cells, eukaryotic cells, prokaryotic cells, infected with a virus, having a phenotype inherited or acquired, cells having a pathological status including a specific pathological status or complexed with biological or non-biological entities.

A "blood sample" as used herein can refer to a processed or unprocessed blood sample, for example, it can be a centrifuged, filtered, extracted, or otherwise treated blood sample, including a blood sample to which one or more reagents such as, but not limited to, anticoagulants or stabilizers have been added. An example of blood sample is a buffy coat that is obtained by processing human blood for enriching white blood cells. A blood sample can be of any volume, and can be from any subject such as an animal or human. A preferred subject is a human. Blood samples can be from a given individual or specific or known or unknown condition or pooled samples. Such conditions can be practically inherent or acquired from contact with objects or exposure to environmental conditions, including but not limited to toxins or radiation. Environmental conditions include those provided during medical treatment, including chemotherapy, drug therapy, therapy and radiation therapy. Environmental conditions also include voluntary exposure or ingestion of compounds, including plant extracts, drugs of abuse, pharmaceuticals, food, toxins, ethanol, tobacco products and the like.

A "white blood cell" is a leukocyte, or a cell of the hematopoietic lineage that is not a reticulocyte or platelet and that can be found in the blood of an animal. Leukocytes can include lymphocytes, such as B lymphocytes or T lymphocytes. Leukocytes can also include phagocytic cells, such as monocytes, macrophages, and granulocytes, including basophils, eosinophils and neutrophils. Leukocytes can also comprise mast cells.

A "red blood cell" is an erythrocyte.

"Neoplastic cells" refers to abnormal cells that grow by cellular proliferation more rapidly than normal and can continue to grow after the stimuli that induced the new growth has been withdrawn. Neoplastic cells tend to show partial or complete lack of structural organization and functional coordination with the normal tissue, and may be benign or malignant.

A "malignant cell" is a cell having the property of locally invasive and destructive growth and metastasis.

A "stem cell" is an undifferentiated cell that can give rise, through one or more cell division cycles, to at least one differentiated cell type.

A "progenitor cell" is a committed but undifferentiated cell that can give rise, through one or more cell division cycles, to at least one differentiated cell type. Typically, a stem cell gives rise to a progenitor cell through one or more cell divisions in response to a particular stimulus or set of stimuli, and a progenitor gives rise to one or more differentiated cell types in response to a particular stimulus or set of stimuli.

An "etiological agent" refers to any etiological agent, such as a bacteria, virus, parasite or prion that can be associated with, such but not limited to infecting, a subject. An etiological agent can cause symptoms or a disease state in the subject it infects. A human etiological agent is an etiological agent that can infect a human subject. Such human etiological agents may be specific for humans, such as a specific human etiological agent, or may infect a variety of species, such as a promiscuous human etiological agent.

"Subject" refers to any organism, such as an animal or a human. An animal can include any animal, such as a feral animal, a companion animal such as a dog or cat, an agricultural animal such as a pig or a cow, or a pleasure animal such as a horse.

A "chamber" is a structure that comprises a chip and that is capable of containing a fluid sample. The chamber may have various dimensions and its volume may vary between 0.001 microliter and 50 milliliter.

A "port" is an opening in the housing of a chamber through which a fluid sample can enter or exit the chamber. A port can be of any dimensions, but preferably is of a shape and size that allows a sample to be dispensed into a chamber by means of a pipette, syringe, or conduit, or other means of dispensing a sample.

A "conduit" is a means for fluid to be transported from one compartment to another compartment of a device of the present invention or to another structure, such as a dispensation or detection device. Preferably a conduit engages a port in the housing of a chamber. A conduit can comprise any material that permits the passage of a fluid through it. Preferably a conduit is tubing, such as, for example, rubber, teflon, or tygon tubing. A conduit can be of any dimensions, but preferably ranges from 10 microns to 5 millimeters in internal diameter.

A "chip" is a solid substrate on which one or more processes such as physical, chemical, biochemical, biological or biophysical processes can be carried out. Such processes can be assays, including biochemical, cellular, and chemical assays; ion transport or ion channel function or activity determinations, separations, including separations mediated by electrical, magnetic, physical, and chemical (including biochemical) forces or interactions; chemical reactions, enzymatic reactions, and binding interactions, including captures. The micro structures or micro-scale structures such as, channels and wells, electrode elements, electromagnetic elements, may be incorporated into or fabricated on the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips of the present invention can vary considerably, for example, from about 1 mm$^2$ to about 0.25 m$^2$. Preferably, the size of the chips is from about 4 mm$^2$ to about 25 cm$^2$ with a characteristic dimension from about 1 mm to about 5 cm. The chip surfaces may be flat, or not flat. The chips with non-flat surfaces may include wells fabricated on the surfaces.

A "biochip" is a chip that is useful for a biochemical, biological or biophysical process. In this regard, a biochip is preferably biocompatible.

"Micro-scale structures" are structures integral to or attached on a chip, wafer, or chamber that have characteristic dimensions of scale for use in microfluidic applications ranging from about 0.1 micron to about 20 mm. Example of micro-scale structures that can be on chips of the present invention are wells, channels, scaffolds, electrodes, electromagnetic units, or microfabricated pumps or valves.

"Separation" is a process in which one or more components of a sample is spatially separated from one or more other components of a sample or a process to spatially redistribute particles within a sample such as a mixture of particles, such as a mixture of cells. A separation can be performed such that one or more particles is translocated to one or more areas of a separation apparatus and at least some of the remaining components are translocated away from the area or areas where the one or more particles are translocated to and/or retained in, or in which one or more particles is retained in one or more areas and at least some or the remaining components are removed from the area or areas. Alternatively, one or more components of a sample can be translocated to and/or retained in one or more areas and one or more particles can be removed from the area or areas. It is also possible to cause one or more particles to be translocated to one or more areas and one or more moieties of interest or one or more components of a sample to be translocated to one or more other areas. Separations can be achieved through the use of physical, chemical, electrical, or magnetic forces. Examples of forces that can be used in separations include but are not limited to gravity, mass flow, dielectrophoretic forces, traveling-wave dielectrophoretic forces, and electromagnetic forces.

"Capture" is a type of separation in which one or more particles is retained in one or more areas of a chip. In the methods of the present application, a capture can be performed when physical forces such as dielectrophoretic forces or electromagnetic forces are acted on the particle and direct the particle to one or more areas of a chip.

An "assay" is a test performed on a sample or a component of a sample. An assay can test for the presence of a component, the amount or concentration of a component, the composition of a component, the activity of a component, the electrical properties of an ion transport protein, etc. Assays that can be performed in conjunction with the compositions and methods of the present invention include, but not limited to, biochemical assays, binding assays, cellular assays, genetic assays, ion transport assay, gene expression assays and protein expression assays.

A "binding assay" is an assay that tests for the presence or the concentration of an entity by detecting binding of the entity to a specific binding member, or an assay that tests the ability of an entity to bind another entity, or tests the binding affinity of one entity for another entity. An entity can be an organic or inorganic molecule, a molecular complex that comprises, organic, inorganic, or a combination of organic and inorganic compounds, an organelle, a virus, or a cell. Binding assays can use detectable labels or signal generating systems that give rise to detectable signals in the presence of the bound entity. Standard binding assays include those that rely on nucleic acid hybridization to detect specific nucleic acid sequences, those that rely on antibody binding to entities, and those that rely on ligands binding to receptors.

A "biochemical assay" is an assay that tests for the composition of or the presence, concentration, or activity of one or more components of a sample.

A "cellular assay" is an assay that tests for or with a cellular process, such as, but not limited to, a metabolic activity, a catabolic activity, an ion transport function or property, an intracellular signaling activity, a receptor-linked signaling activity, a transcriptional activity, a translational activity, or a secretory activity.

An "ion transport assay" is an assay useful for determining ion transport functions or properties and testing for the abilities and properties of chemical entities to alter ion transport functions. Preferred ion transport assays include electrophysiology-based methods which include, but are not limited to patch clamp recording, whole cell recording, perforated patch or whole cell recording, vesicle recording, outside out and inside out recording, single channel recording, artificial membrane channel recording, voltage gated ion transport recording, ligand gated ion transport recording, stretch activated (fluid flow or osmotic) ion transport recording, and recordings on energy requiring ion transporters (such as ATP), non energy requiring transporters, and channels formed by toxins such a scorpion toxins, viruses, and the like. See, generally Neher and Sakman, Scientific American 266: 44-51 (1992); Sakmann and Heher, Ann. Rev. Physiol. 46:455-472 (1984); Cahalan and Neher, Methods in Enzymology 207:3-14 (1992); Levis and Rae, Methods in Enzymology 207:14-66 (1992); Armstrong and Gilly, Methods in Enzymology 207:100-122 (1992); Heinmann and Conti, Methods in Enzymology 207:131-148 (1992); Bean, Methods in Enzymology 207:181-193 (1992); Leim et al., Neurosurgery 36:382-392 (1995); Lester, Ann. Rev. Physiol 53:477-496 (1991); Hamill and McBride, Ann. Rev. Physiol 59:621-631 (1997); Bustamante and Varranda, Brazilian Journal 31:333-354 (1998); Martinez-Pardon and Ferrus, Current Topics in Developmental Biol. 36:303-312 (1998); Hemess, Physiology and Behavior 69:17-27 (2000); Aston-Jones and Siggins, www.acnp.org/GA/GN40100005/CH005.html (Feb. 8, 2001); U.S. Pat. Nos. 6,117,291; 6,107,066; 5,840,041 and 5,661,035; Boulton et al., Patch-Clamp Applications and Protocols, Neuromethods V. 26 (1995), Humana Press, New Jersey; Ashcroft, Ion Channels and Disease, Cannelopathies, Academic Press, San Diego (2000); Sakmann and Neher, Single Channel Recording, second edition, Plenuim Press, New York (1995) and Soria and Cena, Ion Channel Pharmacology, Oxford University Press, New York (1998), each of which is incorporated by reference herein in their entirety.

An "electric sealing" refers to a high-resistance engagement between a particle such as a cell membrane and a measuring device, such as a hole, capillary or needle of the present invention. Preferred resistance of such electric sealing is between about 1 mega ohm and about 100 giga ohms, but that need not be the case. Generally, a large resistance results in decreased noise in the recording signals. For specific types of ion channels (with different magnitude of recording current) appropriate electric sealing in terms of mega ohms or giga ohms can be used A "ligand gated ion transport" refers to ion transporters such as ligand gated ion channels, including extracellular ligand gated ion channels and intracellular ligand gated ion channels, whose activity or function is activated or modulated by the binding of a ligand. The activity or function of ligand gated ion transports can be detected by measuring voltage or current in response to ligands or test chemicals. Examples include but are not limited to $GABA_A$, strychnine-sensitive glycine, nicotinic acetylcholine (Ach), ionotropic glutamate (iGlu), and 5-hydroxytryptamine$_3$ (5-HT$_3$) receptors.

A "voltage gated ion transport" refers to ion transporters such as voltage gated ion channels whose activity or function is activated or modulated by voltage. The activity or function of voltage gated ion transports can be detected by measuring voltage or current in response to different commanding currents or voltages respectively. Examples include but are not limited to voltage dependent $Na^+$ channels.

"Perforated" patch clamp refers to the use of perforation agents such as but not limited to nystatin or amphotericin B to form pores or perforations that are preferably ion-conducting, which allows for the measurement of current, including whole cell current.

An "electrode" is a structure of highly electrically conductive material. A highly conductive material is a material with conductivity greater than that of surrounding structures or materials. Suitable highly electrically conductive materials include metals, such as gold, chromium, platinum, aluminum, and the like, and can also include nonmetals, such as carbon, conductive liquids and conductive polymers. An electrode can be any shape, such as rectangular, circular, castellated, etc. Electrodes can also comprise doped semi-conductors, where a semi-conducting material is mixed with small amounts of other "impurity" materials. For example, phosphorous-doped silicon may be used as conductive materials for forming electrodes.

A "well" is a structure in a chip, with a lower surface surrounded on at least two sides by one or more walls that extend from the lower surface of the well or channel. The walls can extend upward from the lower surface of a well or channel at any angle or in any way. The walls can be of an irregular conformation, that is, they may extend upward in a sigmoidal or otherwise curved or multi-angled fashion. The lower surface of the well or channel can be at the same level as the upper surface of a chip or higher than the upper surface of a chip, or lower than the upper surface of a chip, such that the well is a depression in the surface of a chip. The sides or walls of a well or channel can comprise materials other than those that make up the lower surface of a chip. In this way the lower surface of a chip can comprise a thin material through which electrical (including dielectrophoretic, traveling-wave dielectrophoretic, electromagnetic) forces can be transmitted, and the walls of one or more wells and/or one or more channels can optionally comprise other insulating materials that can prevent the transmission of electrical forces. The walls of a well or a channel of a chip can comprise any suitable material, including silicon, glass, rubber, and/or one or more polymers, plastics, ceramics, or metals.

A "channel" is a structure in a chip with a lower surface and at least two walls that extend upward from the lower surface of the channel, and in which the length of two opposite walls is greater than the distance between the two opposite walls. A channel therefore allows for flow of a fluid along its internal length. A channel can be covered (a "tunnel") or open.

"Continuous flow" means that fluid is pumped or injected into a chamber of the present invention continuously during the separation process. This allows for components of a sample that are not selectively retained on a chip to be flushed out of the chamber during the separation process.

"Binding partner" refers to any substances that both bind to the moieties with desired affinity or specificity and are manipulatable with the desired physical force(s). Non-limiting examples of the binding partners include cells, cellular organelles, viruses, particles, microparticles or an aggregate or complex thereof, or an aggregate or complex of molecules.

A "specific binding member" is one of two different molecules having an area on the surface or in a cavity that specifically binds to and is thereby defined as complementary with a particular spatial and polar organization of the other molecule. A specific binding member can be a member of an immunological pair such as antigen-antibody, can be biotin-avidin or biotin streptavidin, ligand-receptor, nucleic acid duplexes, IgG-protein A, DNA-DNA, DNA-RNA, RNA-RNA, and the like.

A "nucleic acid molecule" is a polynucleotide. A nucleic acid molecule can be DNA, RNA, or a combination of both. A nucleic acid molecule can also include sugars other than ribose and deoxyribose incorporated into the backbone, and thus can be other than DNA or RNA. A nucleic acid can comprise nucleobases that are naturally occurring or that do not occur in nature, such as xanthine, derivatives of nucleobases, such as 2-aminoadenine, and the like. A nucleic acid molecule of the present invention can have linkages other than phosphodiester linkages. A nucleic acid molecule of the present invention can be a peptide nucleic acid molecule, in which nucleobases are linked to a peptide backbone. A nucleic acid molecule can be of any length, and can be single-stranded, double-stranded, or triple-stranded, or any combination thereof. The above described nucleic acid molecules can be made by a biological process or chemical synthesis or a combination thereof.

A "detectable label" is a compound or molecule that can be detected, or that can generate readout, such as fluorescence, radioactivity, color, chemiluminescence or other readouts known in the art or later developed. Such labels can be, but are not limited to, photometric, colorimetric, radioactive or morphological such as changes of cell morphology that are detectable, such as by optical methods. The readouts can be based on fluorescence, such as by fluorescent labels, such as but not limited to, Cy-3, Cy-5, phycoerythrin, phycocyanin, allophycocyanin, FITC, rhodamine, or lanthanides; and by fluorescent proteins such as, but not limited to, green fluorescent protein (GFP). The readout can be based on enzymatic activity, such as, but not limited to, the activity of beta-galactosidase, beta-lactamase, horseradish peroxidase, alkaline phosphatase, or luciferase. The readout can be based on radioisotopes (such as $^{33}P$, $^{3}H$, $^{14}C$, $^{35}S$, $^{125}I$, $^{32}P$ or $^{131}I$). A label optionally can be a base with modified mass, such as, for example, pyrimidines modified at the C5 position or purines modified at the N7 position. Mass modifying groups can be, for examples, halogen, ether or polyether, alkyl, ester or polyester, or of the general type XR, wherein X is a linking group and R is a mass-modifying group. One of skill in the art will recognize that there are numerous possibilities for mass-modifications useful in modifying nucleic acid molecules and oligonucleotides, including those described in Oligonucleotides and Analogues: A Practical Approach, Eckstein, ed. (1991) and in PCT/US94/00193.

A "signal producing system" may have one or more components, at least one component usually being a labeled binding member. The signal producing system includes all of the reagents required to produce or enhance a measurable signal including signal producing means capable of interacting with a label to produce a signal. The signal producing system provides a signal detectable by external means, often by measurement of a change in the wavelength of light absorption or emission. A signal producing system can include a chromophoric substrate and enzyme, where chromophoric substrates are enzymatically converted to dyes, which absorb light in the ultraviolet or visible region, phosphors or fluorescers. However, a signal producing system can also provide a detectable signal that can be based on radioactivity or other detectable signals.

The signal producing system can include at least one catalyst, usually at least one enzyme, and can include at least one substrate, and may include two or more catalysts and a plurality of substrates, and may include a combination of enzymes, where the substrate of one enzyme is the product of the other enzyme. The operation of the signal producing system is to produce a product that provides a detectable signal at the predetermined site, related to the presence of label at the predetermined site.

In order to have a detectable signal, it may be desirable to provide means for amplifying the signal produced by the presence of the label at the predetermined site. Therefore, it will usually be preferable for the label to be a catalyst or luminescent compound or radioisotope, most preferably a catalyst. Preferably, catalysts are enzymes and coenzymes that can produce a multiplicity of signal generating molecules from a single label. An enzyme or coenzyme can be employed which provides the desired amplification by producing a product, which absorbs light, for example, a dye, or emits light upon irradiation, for example, a fluorescer. Alternatively, the catalytic reaction can lead to direct light emission, for example, chemiluminescence. A large number of enzymes and coenzymes for providing such products are indicated in U.S. Pat. Nos. 4,275,149 and 4,318,980, which disclosures are incorporated herein by reference. A wide variety of non-enzymatic catalysts that may be employed are found in U.S. Pat. No. 4,160,645, issued Jul. 10, 1979, the appropriate portions of which are incorporated herein by reference.

The product of the enzyme reaction will usually be a dye or fluorescer. A large number of illustrative fluorescers are indicated in U.S. Pat. No. 4,275,149, which is incorporated herein by reference.

An "ion transport" can be any protein or non-protein moiety that modulates, regulates or allows transfer of ions across a membrane, such as a biological membrane or an artificial membrane. Ion transporters include but are not limited to ion channels, proteins allowing transport of ions by active transport, proteins allowing transport of ions by passive transport, toxins such as from insects, viral proteins or the like. Viral proteins, such as the M2 protein of influenza virus can form an ion channel on cell surfaces.

A "particle" refers to an organic or inorganic particulate that is suspendable in a solution and can be manipulated by a particle positioning means. A particle can include a cell, such as a prokaryotic or eukaryotic cell, or can be a cell fragment, such as a vesicle or a microsome that can be made using methods known in the art. A particle can also include artificial membrane preparations that can be made using methods known in the art. Preferred artificial membrane preparations are lipid bilayers, but that need not be the case. A particle in the present invention can also be a lipid film, such as a black-lipid film (see, Houslay and Stanley, Dynamics of Biological Membranes, Influence on Synthesis, Structure and Function, John Wiley & Sons, New York (1982)). In the case of a lipid film, a lipid film can be provided over a hole, such as a hole or capillary of the present invention using methods known in the art (see, Houslay and Stanley, Dynamics of Biological Membranes, Influence on Synthesis, Structure and Function, John Wiley & Sons, New York (1982)). A particle preferably includes or is suspected of including at least one ion transport or an ion transport of interest. Particles that do not include an ion transport or an ion transport of interest can be made to include such ion transport using methods known in the art, such as by fusion of particles or insertion of ion transports into such particles such as by detergents, detergent removal, detergent dilution, sonication or detergent catalyzed incorporation (see, Houslay and Stanley, Dynamics of Biological Membranes, Influence on Synthesis, Structure and Function, John Wiley & Sons, New York (1982)). A microparticle, such as a bead, such as a latex bead or magnetic bead, can be attached to a particle, such that the particle can be manipulated by a particle positioning means.

A "microparticle" is a structure of any shape and of any composition that is manipulatable by desired physical force(s). The microparticles used in the methods could have a dimension from about 0.01 micron to about ten centimeters. Preferably, the microparticles used in the methods have a dimension from about 0.1 micron to about several hundred microns. Such particles or microparticles can be comprised of any suitable material, such as glass or ceramics, and/or one or more polymers, such as, for example, nylon, polytetrafluoroethylene (TEFLON™), polystyrene, polyacrylamide, sepaharose, agarose, cellulose, cellulose derivatives, or dextran, and/or can comprise metals. Examples of microparticles include, but are not limited to, plastic particles, ceramic particles, carbon particles, polystyrene microbeads, glass beads, magnetic beads, hollow glass spheres, metal particles, particles of complex compositions, microfabricated free-standing microstructures, etc. The examples of microfabricated free-standing microstructures may include those described in "Design of asynchronous dielectric micromotors" by Hagedorn et al., in Journal of Electrostatics, Volume: 33, Pages 159-185 (1994). Particles of complex compositions refer to the particles that comprise or consists of multiple compositional elements, for example, a metallic sphere covered with a thin layer of non-conducting polymer film.

"A preparation of microparticles" is a composition that comprises microparticles of one or more types and can optionally include at least one other compound, molecule, structure, solution, reagent, particle, or chemical entity. For example, a preparation of microparticles can be a suspension of microparticles in a buffer, and can optionally include specific binding members, enzymes, inert particles, surfactants, ligands, detergents, etc.

"Coupled" means bound. For example, a moiety can be coupled to a microparticle by specific or nonspecific binding. As disclosed herein, the binding can be covalent or noncovalent, reversible or irreversible.

A "cell" refers to a viable or non-viable prokaryotic or eukaryotic cell. A eukaryotic cell can be any eukaryotic cell from any source, such as obtained from a subject, human or non-human, fetal or non-fetal, child or adult, such as from a tissue or fluid, including blood, which are obtainable through appropriate sample collection methods, such as biopsy, blood collection or otherwise. Eukaryotic cells can be provided as is in a sample or can be cell lines that are cultivated in vitro. Differences in cell types also include cellular origin, distinct surface markers, sizes, morphologies and other physical and biological properties.

A "cell fragment" refers to a portion of a cell, such as cell organelles, including but not limited to nuclei, endoplasmic reticulum, mitochondria or golgi apparatus. Cell fragments can include vesicles, such as inside out or outside out vesicles or mixtures thereof. Preparations that include cell fragments can be made using methods known in the art.

A "population of cells" refers to a sample that includes more than one cell or more than one type of cell. For example, a sample of blood from a subject is a population of white cells and red cells. A population of cells can also include a sample including a plurality of substantially homogeneous cells, such as obtained through cell culture methods for a continuous cell lines.

A "population of cell fragments" refers to a sample that includes more than one cell fragment or more than one type of cell fragments. For example, a population of cell fragments can include mitochondria, nuclei, microsomes and portions of golgi apparatus that can be formed upon cell lysis.

A "particle positioning means" refers to a means that is capable of manipulating the position of a particle relative to the X-Y coordinates or X-Y-Z coordinates of a biochip. Positions in the X-Y coordinates are in a plane. The Z coordinate is perpendicular to the plane. In one aspect of the present invention, the X-Y coordinates are substantially perpendicular to gravity and the Z coordinate is substantially parallel to gravity. This need not be the case, however, particularly if the biochip need not be level for operation or if a gravity free or gravity reduced environment is present. Several particle positioning means are disclosed herein, such as but not limited to dielectric structures, dielectric focusing structures, quadropole electrode structures, electrorotation structures, traveling wave dielectrophoresis structures, concentric electrode structures, spiral electrode structures, circular electrode structures, square electrode structures, particle switch structures, electromagnetic structures, DC electric field induced fluid motion structure, acoustic structures, negative pressure structures and the like.

An "ion transport measuring means" refers to a means that is capable of measuring ion transport function, properties or response to various chemical, biochemical or electrical stimuli. For example, holes, capillaries, needles and other detection structures of the present invention can be used as ion transport measuring means. An ion transport measuring means is preferably positioned on or within a biochip or a chamber.

A "patch clamp detection structure" refers to a structure that is on or within a biochip or a chamber that is capable of measuring ion transport function or property via patch clamp methods.

A "dielectric focusing structure" refers to a structure that is on or within a biochip or a chamber that is capable of modulating the position of a particle in the X-Y or X-Y-Z coordinates of a biochip using dielectric forces or dielectrophoretic forces.

A "quadropole electrode structure" refers to a structure that includes four electrodes arranged around a locus such as a hole, capillary or needle on a biochip and is on or within a biochip or a chamber that is capable of modulating the position of a particle in the X-Y or X-Y-Z coordinates of a biochip using dielectrophoretic forces or dielectric forces generated by such quadropole electrode structures.

An "electrorotation structure" refers to a structure that is on or within a biochip or a chamber that is capable of producing a rotating electric field in the X-Y or X-Y-Z coordinates that can rotate a particle. Preferred electrorotation structures include a plurality of electrodes that are energized using phase offsets, such as 360/N degrees, where N represents the number of electrodes in the electroroation structure (see generally U.S. patent application Ser. No. 09/643,362 entitled "Apparatus and Method for High Throughput Electrorotation Analysis" filed Aug. 22, 2000, naming Jing Cheng et al. as inventors). A rotating electrode structure can also produce dielectrophoretic forces for positioning particles to certain locations under appropriate electric signal or excitation. For example, when N=4 and electrorotation structure corresponds to a quadropole electrode structure.

A "traveling wave dielectrophoresis structure" refers to a structure that is on or within a biochip or a chamber that is capable of modulating the position of a particle in the X-Y or X-Y-Z coordinates of a biochip using traveling wave dielectrophoretic forces (see generally U.S. patent application Ser. No. 09/686,737 filed Oct. 10, 2000, to Xu, Wang, Cheng, Yang and Wu; and U.S. application Ser. No. 09/678,263, entitled "Apparatus for Switching and Manipulating Particles and Methods of Use Thereof" filed on Oct. 3, 2000 and naming as inventors Xiaobo Wang, Weiping Yang, Junquan Xu, Jing Cheng, and Lei Wu).

A "concentric circular electrode structure" refers to a structure having multiple concentric circular electrodes that are on or within a biochip or a chamber that is capable of modulating the position of a particle in the X-Y or X-Y-Z coordinates of a biochip using dielectrophoretic forces.

A "spiral electrode structure" refers to a structure having multiple parallel spiral electrode elements that is on or within a biochip or a chamber that is capable of modulating the position of a particle in the X-Y or X-Y-Z coordinates of a biochip using dielectric forces.

A "square spiral electrode structure" refers to a structure having multiple parallel square spiral electrode elements that are on or within a biochip or a chamber that is capable of modulating the position of a particle in the X-Y or X-Y-Z coordinates of a biochip using dielectrophoretic or traveling wave dielectrophoretic forces.

A "particle switch structure" refers to a structure that is on or within a biochip or a chamber that is capable of transporting particles and switching the motion direction of a particle or particles in the X-Y or X-Y-Z coordinates of a biochip. The particle switch structure can modulate the direction that a particle takes based on the physical properties of the particle or at the will of a programmer or operator (see, generally U.S. application Ser. No. 09/678,263, entitled "Apparatus for Switching and Manipulating Particles and Methods of Use Thereof" filed on Oct. 3, 2000 and naming as inventors Xiaobo Wang, Weiping Yang, Junquan Xu, Jing Cheng, and Lei Wu.

An "electromagnetic structure" refers to a structure that is on or within a biochip or a chamber that is capable of modulating the position of a particle in the X-Y or X-Y-Z coordinates of a biochip using electromagnetic forces. See generally U.S. patent application Ser. No. 09/685,410 filed Oct. 10, 2000, to Wu, Wang, Cheng, Yang, Zhou, Liu and Xu and WO 00/54882 published Sep. 21, 2000 to Zhou, Liu, Chen, Chen, Wang, Liu, Tan and Xu.

A "DC electric field induced fluid motion structure" refers to a structure that is on or within a biochip or a chamber that is capable of modulating the position of a particle in the X-Y or X-Y-Z coordinates of a biochip using DC electric field that produces a fluidic motion.

An "electroosomosis structure" refers to a structure that is on or within a biochip or a chamber that is capable of modulating the position of a particle in the X-Y or X-Y-Z coordinates of a biochip using electroosmotic forces. Preferably, an electroosmosis structure can modulate the positioning of a particle such as a cell or fragment thereof with an ion transport measuring means such that the particle's seal (or the particle's sealing resistance) with such ion transport measuring means is increased.

An "acoustic structure" refers to a structure that is on or within a biochip or a chamber that is capable of modulating the position of a particle in the X-Y or X-Y-Z coordinates of a biochip using acoustic forces. In one aspect of the present invention, the acoustic forces are transmitted directly or indirectly through an aqueous solution to modulate the positioning of a particle. Preferably, an acoustic structure can modulate the positioning of a particle such as a cell or fragment thereof with an ion transport measuring means such that the particle's seal with such ion transport measuring means is increased.

A "negative pressure structure" refers to a structure that is on or within a biochip or a chamber that is capable of modulating the position of a particle in the X-Y or X-Y-Z coordinates of a biochip using negative pressure forces, such as those generated through the use of pumps or the like. Preferably, a negative pressure structure can modulate the positioning of a particle such as a cell or fragment thereof with an ion transport measuring means such that the particle's seal with such ion transport measuring means is increased.

A "horizontal positioning means" refers to a particle positioning means that can position a particle in the X-Y coordinates of a biochip or chamber wherein the Z coordinate is substantially defined by gravity.

A "vertical positioning means" refers to a particle positioning means that can position a particle in the Z coordinate of a biochip or chamber wherein the Z coordinate is substantially defined by gravity.

Other technical terms used herein have their ordinary meaning in the art that they are used, as exemplified by a variety of technical dictionaries.

Introduction

The present invention recognizes that the determination of ion transport function or property using direct detection methods, such as patch-clamps, are preferable to methods that utilize indirect detection methods, such as fluorescence-based detection system. The present invention provides biochips and methods of use that allow for the direct detection of ion transport function or property using microfabricated structures that can allow for automated detection of ion transport function or property. These biochips and methods of use thereof are particularly appropriate for automating the detection of ion transport function or property, particularly for screening purposes.

As a non-limiting introduction to the breath of the present invention, the present invention includes several general and useful aspects, including:

1) A biochip cell positioning device and methods of use;
2) An array of capillaries on a biochip optionally with electrodes and methods of use thereof;
3) An array of needle electrodes on a biochip and methods of use;
4) An array of holes on a biochip and methods of use;
5) A biochip having ion transport detection structures located along the side of channel;
6) A biochip combined with high information content screening methods; and
7) A biochip with three-dimensionally configured channels that can be microfabricated using sacrificial methodologies such as sacrificial wire methods These aspects of the invention, as well as others described herein, can be achieved by using the methods, articles of manufacture and compositions of matter described herein. To gain a full appreciation of the scope of the present invention, it will be further recognized that various aspects of the present invention can be combined to make desirable embodiments of the invention.

I A Biochip Cell Positioning Device and Methods of Use

The present invention includes a biochip that includes a particle positioning means and an ion transport measuring means. The particle positioning means such as, but not limited to dielectric focusing devices, electrorotation devices, dielectrophoresis devices, traveling wave dielectrophoresis devices or acoustic devices that can precisely position a particle, such as a cell, at or near an ion transport measuring means. Preferred ion transport measuring means include holes or capillaries that can form a seal with the particle, such as a biological membrane, so that ion transport function or property of the particle can be determined. Coupled with holes or capillaries there can be electrodes that can record electric responses of ion channels.

Biochips in General

Biochips of the present invention generally are made using microfabrication methods such as those generally used in electronic chip manufacture. For example, methods of photolithography, MEMS fabrication, micromachining, molding, casting and other methods can be used. Generally, biochips include a substrate that forms a solid support or platform on which a separation or an assay can take place. Biochips can also include chambers or conduits to allow for the introduction of materials onto the substrate or within the channels of the biochip.

Substrate

The substrate can be of any appropriate material or combination of materials for the manufacture of chips, such as through microfabrication methods used in the semiconductor industry. Preferred materials include, but are not limited to silicon, glass, sintered glass, quartz, silicon-oxide, plastics, ceramics or the like. The substrate is preferably non-porous, but porous materials are also useful, particularly for applications that utilize the transfer of materials through a substrate to take part in methods of the present invention, such as but not limited to binding reactions or detection of binding reactions.

The substrate is preferably of dimensions that are appropriate for microfabrication methods, such as etching, sputtering, masking and the like. The substrate is also preferably of a size appropriate for micromanipulation of particles and for ion transport function or properties such as described in the methods herein. For example, the substrate is preferably thin, such as about a millimeter in thickness, and between about 5 millimeters and about 50 centimeters in length and width, preferably between about 1 centimeter and about 5 centimeters in length and width. However, such sizes are not considered limiting to the present invention. The substrate can be of any appropriate shape, such as geometric or non-geometric shapes, such as square, circular, oblong, elliptical or the like. Preferred shapes include squares, circles, and appropriate polygons.

The substrate can be part of a single layer or multi-layered chip that can have a plurality of functions. For example, a single layer chip can include a variety of structures to perform a variety of functions, particularly particle positioning means. Preferred particle positioning means include, for example, such as acoustic structures or vibrational structures such as piezoelectric materials as they are known in the art to generate acoustic fields in a sample; dielectric structures such as dielectric focusing structures, quadropole electrode structures, traveling wave dielectrophoresis structures, concentric circular electrode structure, spiral electrode structure, square spiral electrode structure, particle switch structure; electrorotational structures; electromagnetic structures; DC electric field induced fluid motion structures, electroosmosis structures or negative pressure structures to move or modulate moieties or particles. Alternatively, these additional structures, such as vibrational structures or dielectric structures can be provided in separate layers of substrate. In this aspect of the present invention, a plurality of substrates can be sandwiched and adhered together and fabricated into a multifunctional chip. The different functional elements can be independently controlled by appropriate controlling devices, such as switches and conductive materials (see, generally U.S. application Ser. No. 09/679,024, entitled "Apparatuses Containing Multiple Active Force Generating Elements and Uses Thereof" filed Oct. 4, 2000, and naming as inventors Xiaobo Wang, Jing Cheng, Lei Wu, Weiping Yang and Junquan Xu).

Coating

The substrate can optionally include a coating. The coating can be provided as a thin film of appropriate material to prevent direct interaction of particles with the substrate of a biochip. Alternatively, the coating can provide structures, such as holes, that can align with or interact with structures on or within the substrate, such as particle positioning means or holes or capillaries. Because a coating can be thinner than a substrate, precise micromanufacture of structures, particularly holes, can be done with higher degrees of accuracy or precision when compared with substrates. The film can be of any appropriate material, but is preferably a polymer, such as a plastic. The film can be made by adhering a premade film to a substrate, or can be made on the substrate. In the latter instance, for example, a solution of monomer can be dispensed onto a surface and the monomer polymerized using appropriate methods, such as the use of a polymerizing agent, such as an initiator. In one aspect of the present invention, two or more layers of polymerized materials can be made such that the polymerized layer can be made incrementally thicker using this type of process.

The coating can be a functional layer. A functional layer can include at least one immobilized moiety or ligand. Preferred immobilized moieties include charged groups, nucleic acid molecules, antibodies or receptors. The functional layer, when present, can be provided on the surface of the substrate such as to provide a variety of chemical groups or biological groups that can be utilized in the methods of the present invention. For example, antibodies or cell adhesion molecules or active fragments thereof can be localized at, near or on or within holes, capillaries or needles of the devices of the present invention so that a good electric seal between the particle such as a cell and the device can be achieved.

The functional layer can be of any appropriate material, but is preferably includes at least one of the following materials: a hydrophilic molecular monolayer, a hydrophilic molecular monolayer with functional groups, a hydrophobic molecular monolayer, a hydrophobic molecular monolayer with functional groups, a hydrophilic membrane, a hydrophilic membrane with functional groups, a hydrophobic membrane, a hydrophobic membrane with functional groups, a hydrophilic gel, a hydrophilic gel with functional groups, a hydrophobic gel, a hydrophobic gel with functional groups, a porous material, a porous material with functional groups, a non-porous material and a non-porous material with functional groups.

The functional layer can be a sheet of material that is contacted, attached or adhered to the substrate. In the alternative, the functional layer can be made by modifying, such as by chemical modification, of the substrate. Furthermore, the functional layer can be made by spraying, dipping or otherwise contacting liquid or semisolid material onto the substrate, wherein the material is then solidified such as through cooling, gelling, solidifying or polymerization.

The functional layer can have a variety of functional groups that can take part in a variety of chemical or biochemical reactions designed to immobilize particles thereon. Preferred functional groups include but are not limited to aldehydes, carbodiimides, succinimydyl esters, antibodies, receptors and lectins. Materials having these functional groups are known in the art. In addition, methods of making a variety of surfaces having these functional groups are known in the art.

The functional layer can include a moiety or ligand immobilized thereon. Preferred immobilized moieties or ligands include, but are not limited to nucleic acid molecules (such as single stranded or double stranded DNA or RNA or a combination thereof), binding reagents (such as antibodies or active fragments thereof), receptors or other members of binding pair, polypeptides, proteins, carbohydrates, lipids, prokaryotic cells, eukaryotic cells, prions, viruses, parasites, bacteria antibodies, lectins or receptors. Functional layers having such immobilized moieties thereon can be made using a variety of methods. For example, a functional layer with an appropriate functional group can be contacted with a preparation having a moiety to be immobilized thereon. The immobilization of such moieties on a functional layer can be throughout the functional layer or localized using appropriate methods, such as masking. For example, antibodies or cell adhesion molecules or active fragments thereof can be localized at, near or on or within holes, capillaries or needles of the devices of the present invention so that a good electric seal between the particle such as a cell and the device can be achieved.

Chambers

The substrate is preferably provided as part of a chamber that can hold samples, such as fluids. The chamber forms walls around at least a portion of the substrate such that fluid can be stored. Optionally, the chamber can be sealed on all sides, but that need not be the case. In addition, a chamber can be connected to a variety of structures such as ports or conduits to allow fluids or solids such as samples or reagents to enter the chamber, such as through conduits. The fluids or solids are introduced into the chamber by appropriate methods or forces, such as by gravity feed or pumps. The chamber can also include exit structures, such as conduits or ports that allow materials within the chamber to be removed. In one preferred aspect of the present invention, the chamber is a flow through chamber that allows materials to be introduced by way of entry structures such as ports or conduits and materials to be removed by way of exit structures such as ports or conduits.

A chamber of the present invention is a structure that can contain a fluid sample. A chamber can be of any size or dimensions, and preferably can contain a fluid sample of between one nanoliter and 50 milliliters, more preferably between about 1 microliter and about 10 milliliters, and most preferably between about 10 microliters and about 1 milliliter. Preferably, a chamber comprises a chip. A chamber can comprise any suitable material, for example, silicon, glass, metal, ceramics, polymers, plastics, etc. and can be of a rigid or flexible material.

Chambers used in the methods of the present invention can comprise chips, where chips are solid supports on which one or more separations, assays, transportation switching, electrophysiology measurements or capturing procedures can be performed. A chip can comprise one or more metals, ceramics, polymers, copolymers, plastics, rubber, silicon, or glass. A chip can comprise one or more flexible materials. A chip can be from about one $mm^2$ to about 0.25 $m^2$. Preferably, the size of the chips useable in the present methods is from about four $mm^2$ to about 25 $cm^2$. The shape of the chips useable in the present methods can be regular shapes such as square, rectangular, circular, or oval, or can be irregularly shaped. Chips useable in the methods of the present invention can have one or more wells or one or more channels that can be etched into a chip or built onto the surface of a chip.

Preferably, in embodiments where the chamber comprises electrodes, the electrodes will be incorporated onto or within the chip, but this is not a requirement of the present invention. Electrodes on a chip can be of any shape, such as rectangular, castellated, triangular, circular, and the like. Electrodes can be arranged in various patterns, for example, spiral, parallel, interdigitated, polynomial, etc. Electrodes can be arranged so that dielectrophoretic forces can be produced to position particles such as cells to desired locations. Electrode arrays can be fabricated on a chip by methods known in the art, for example, electroplating, sputtering, photolithography or etching. Examples of a chip comprising electrodes include, but are not limited to, the dielectrophoresis electrode array on a glass substrate (for example, Dielectrophoretic Manipulation of Particles by Wang et al., in IEEE Transaction on Industry Applications, Vol. 33, No. 3, May/June, 1997, pages 660-669), individually addressable electrode array on a microfabricated bioelectronic chip (e.g., Preparation and Hybridization Analysis of DNA/RNA from E. coli on Microfabricated Bioelectronic Chips by Cheng et al., Nature Biotechnology, Vol. 16, 1998, pages 541-546), and the capillary electrophoresis chip (for example, Combination of Sample-Preconcentration and Capillary Electrophoresis On-Chip by Lichtenberg, et al., in Micro Total Analysis Systems 2000 edited by A. van den Berg et al., pages 307-310).

A chamber that comprises a chip useable in the methods of the present invention can comprise one or more ports, or openings in the walls of a chamber. Preferably, a port is of a shape and size that allows a conduit to engage a port for the dispensing of a sample into the chamber. A conduit can be any tube that allows for the entry of a fluid sample into the chamber. Preferred conduits for use in the present invention include tubing, for example, rubber or polymeric tubing, for example, tygon or Teflon tubing. Alternatively, a port can provide an opening in a wall of a chamber for the dispensing of sample into the chamber by, for example, pipetting or injection.

Conduits that engage one or more ports of the sample can introduce a sample by means of a pump (for example, a peristaltic pump or infusion pump), pressure source syringe, or gravity feed. One or more reagents, buffers, or solutions, including, but not limited to, a solution of the present invention that selectively modifies the dielectric properties of one or more moieties in a sample, can be added to the chamber before, after, or concurrently with the addition of a sample to a chamber. It is also within the scope of the invention to mix the sample with a reagent, buffer, or solution, before adding the sample to the chamber. Such mixing can optionally occur in one or more conduits leading to a chamber, or in one or more reservoirs connected to conduits.

Particle Positioning Means

A biochip of the present invention preferably includes particle positioning means on substrate, within the substrate, partially within the substrate or on within or partially within the coating, although such particle positioning means can be separate from such substrate altogether. These particle positioning means are preferably manufactured using microfabrication methods, such as etching, lithography or masking, but other methods, such as machining or micro-machining can be used. The particle positioning means are active upon a particle, parts of a particle or population of particles, such as a cell, portions of cells, or cells depending on their physical characteristics. Particles can include, for example, cells or portions of cells that are linked directly or indirectly to another particle, such as a bead or microparticle, such as a polymeric bead or magnetic bead. These particles such as cells associated with additional particles can have physical properties different from the cell or cell fragment, such as dielectrophoretic mobility or susceptibility to a magnetic field.

The particle positioning means are preferably arranged such that particles can be mobilized using such particle positioning means so that particles are mobilized and positioned at, on or in close proximity to an ion transport measuring means.

The particle positioning means preferably include at least one structure selected from the group consisting of dielectric focusing structure, quadropole electrode structure, electrorotation structure, traveling wave dielectrophoresis structure, concentric circular electrode structure, spiral electrode structure, square spiral electrode structure, particle switch structure, electromagnetic structure, DC electric field-induced fluid motion structure, AC electric field induced fluid motion structure, electrophoretic structure, electroosmosis structure, acoustic structure or negative pressure structure. One or more of these structures can be integrated into a biochip for use as particle positioning structures or means. In one aspect of the present invention, one or more of these structures can be integral to a chip and can optionally be serviced by the same or different set of electrodes leading to a chip.

Dielectric Structures

A number of dielectrophoretic manipulation methods may be used for manipulating particles or cells in the present invention. For example, dielectrophoretic separation methods may be used for separating or isolating target cells or particles before they are transported to the ion transport determining means for assaying their ion transport properties. The methods that can be used for the dielectrophoretic separation in the present invention include but are not limited to the following: dielectrophoretic techniques, dielectrophoretic migration, dielectrophoretic retention, dielectrophoretic/gravitational field flow fractionation, traveling-wave dielectrophoresis and 2-D dielectrophoresis.

For an electric field of non-uniform magnitude distribution, the dielectrophoretic force on a particle of radius r can be determined, under the dipole approximation, by the following equation:

$$\vec{F}_{DEP} = 2\pi \in_m r^3 \chi_{DEP} \nabla E_{rms}^2 \quad (1)$$

where $E_{rms}$ is the RMS value of the field strength, the symbol $\nabla$ is the symbol for gradient-operation, $\in_m$ is the dielectric permittivity of the medium, and $\chi_{DEP}$ is the particle polarization factor (or dielectrophoretic polarization factor), given by:

$$\chi_{DEP} = \text{Re}\left(\frac{\varepsilon_p^* - \varepsilon_m^*}{\varepsilon_p^* + 2\varepsilon_m^*}\right), \quad (2)$$

"Re" refers to the real part of the "complex number". The symbol $\in_x^* = \in_x - j\sigma_x/2\pi f$ is the complex permittivity (of the particle x=p, and the medium x=m) and $j=\sqrt{-1}$. The parameters $\in_p$ and $\in_p$ are the effective permittivity and conductivity of the particle, respectively.

When a particle exhibits a positive dielectrophoretic polarization factor ($\chi_{DEP}>0$), the particle is moved by dielectrophoretic forces toward regions where the field is the strongest.

On the other hand, when a particle exhibits a negative dielectrophoretic polarization factor ($\chi_{DEP}<0$), the particle is moved by dielectrophoretic forces away from those regions where the field is strongest and toward those regions where the field is weakest.

The traveling wave dielectrophoretic force for an ideal traveling wave field acting on a particle of radius r an subjected to a traveling-wave electrical field E=E cos(2π(ft−z/λ₀))$\vec{a}_x$ (i.e. the x-component of an E-field traveling in the $\vec{a}_x$-direction, the phase value of the field x-component being a linear function of the position along the z-direction) is given by:

$$\vec{F}_{TW-DEP} = -\frac{4\pi^2 \varepsilon_m}{\lambda_0} r^3 \zeta_{TWD} E^2 \cdot \vec{a}_z \quad (4)$$

where where E is the magnitude of the field strength, $\in_m$ is the dielectric permittivity of the medium. $\zeta_{TWD}$ is the particle traveling-wave dielectrophoretic polarization factor, given by $$\zeta_{TW-DEP} = \text{Im}\left(\frac{\varepsilon_p^* - \varepsilon_m^*}{\varepsilon_p^* + 2\varepsilon_m^*}\right),$$

"Im" refers to the imaginary part of the "complex number". The symbol $\in_x^* = \in_x - j\sigma_x/2\pi f$ is the complex permittivity (of the particle x=p, and the medium x=m). The parameters $\in_p$ and $\in_p$ are the effective permittivity and conductivity of the particle, respectively. These parameters may be frequency dependent.

The traveling wave dielectrophoretic force acts on a particle that is either oriented with or against that of the direction of propagation of the traveling-wave field, depending upon whether the traveling wave dielectrophoretic polarization factor is negative or positive. If a particle exhibits a positive traveling wave dielectrophoretic polarization factor ($\zeta_{TW-DEP}>0$) at the frequency of operation, the traveling wave dielectrophoretic force will be exerted on the particle in a direction opposite that of the direction in which the electric field travels. On the other hand, if a particle exhibits a negative traveling wave dielectrophoretic polarization factor ($\zeta_{TW-DEP}<0$) at the frequency of operation, the traveling wave dielectrophoretic force will be exerted on the particle in the same direction in which the electric field travels.

Thus, the movement of a particle in a non-uniform electric field depends in part on the size (r), permittivity ($\in_p$), and conductivity ($\sigma_p$) of the particle. The size of a particle in part determines the magnitude of the dielectrophoretic force, whereas the conductivity and permittivity of a particle influence the direction and the magnitude of a particle's movement in a non-uniform field. Accordingly, particles that have different dielectric properties but are subjected to identical electrical fields will experience different dielectrophoretic forces and different traveling wave dielectrophoretic forces.

The following discussion of the dielectric properties of particles is provided as background information for factors to be considered in the selection and derivation of particle suspending media or solution for dielectrophoretic positioning and manipulation of particles such as cells. The applicants provide this model as background only, and expressly do not wish to be limited to any mechanism of action described herein.

The permittivies and conductivities of particles depend upon the composition of the particles. For example, a homogeneous particle such as a polystyrene bead has a single permittivity value that determines the effective permittivity of the bead, and a single conductivity value that determines the effective conductivity of the bead. These properties may be independent of the field frequency in a wide frequency range, for example, between 1 Hz and 100 MHz. Particles that have a homogeneous bulk composition may have net surface charges. When such charged particles are suspended in a medium, electrical double layers may form at the particle/medium interfaces. Externally applied electric field may interact with the electrical double layers, causing changes in the effective conductivity and effective permittivity of the particles. The interactions between the applied field and the electrical double layers are generally frequency dependent. Thus, the effective conductivity and effective permittivity of such particles may be frequency dependent.

In contrast, non-homogeneous particles such as cells have a membrane permittivity and an internal permittivity, and a membrane conductivity and an internal conductivity. The effective permittivity and the effective conductivity of a non-homogeneous particle is dependent on both its membrane properties and its internal properties. The effective permittivity and effective conductivity of a non-homogeneous particle are dependent on the field frequency. Different dielectric models have been developed to represent different cell types. In particular, single-shell modeling has been applied to mammalian cells, in which cells are modeled as conducting spheres (corresponding to cell interiors) surrounded by poorly-conducting thin shells (corresponding to cell membranes). The effective cell dielectric property is then determined by dielectric parameters of the cell interiors and membranes and can be calculated according to:

$$\varepsilon_{cell}^* = \varepsilon_{mem}^* \frac{\left(\frac{r}{r-d}\right)^3 + 2\frac{\varepsilon_{int}^* - \varepsilon_{mem}^*}{\varepsilon_{int}^* + 2\varepsilon_{mem}^*}}{\left(\frac{r}{r-d}\right)^3 - \frac{\varepsilon_{int}^* - \varepsilon_{mem}^*}{\varepsilon_{int}^* + 2\varepsilon_{mem}^*}}$$

Here is the complex permittivity $\varepsilon_x^*$ of a cell (x=cell), or its membrane (x=mem) or its interior (x=int). The parameters r and d refer to the cell radius and membrane thickness, respectively.

The frequency dependence of the dielectrophoretic polarization factor ($\chi_{DEP}$) and the traveling wave dielectrophoretic polarization factor ($\zeta_{TW\text{-}DEP}$) of non-homogeneous particles such as cells arises from the frequency dependence of the particles' dielectric properties. The dielectric properties of a mammalian cell are influenced by cell size, membrane thickness, the dielectric properties of the cell membrane, and the dielectric properties of the cell interior. Typically, a viable cell has a poorly-conducting membrane (membrane conductivity is typically small, less than $10^{-4}$ Siemens/m) which encloses a moderately conducting cell interior (interior conductivity is typically high, larger than 0.1 Siemens/m). At low frequencies, the applied field the cell membrane drops across the cell membrane, and the cell membrane dominates the dielectric properties of the whole cell. Under these conditions the cell may have negative values for the dielectrophoretic polarization factor ($\chi_{DEP}$<0) and exhibit negative dielectrophoresis. As frequency is increased, the applied field gradually penetrates through the cell membrane into the cell interior, and the cell's dielectrophoretic polarization factor changes from negative to positive ($\chi_{DEP}$>0). In such a frequency range, the interaction between the cell and the applied field tends to cause the cell to exhibit positive values for the traveling wave polarization factor ($\zeta_{TW\text{-}DEP}$>0). As the frequency is increased further, the cells interior properties (at first the effective conductivity and then the effective permittivity) determine the cell's responses. The cell first exhibits positive values for the dielectrophoresis polarization factor ($\chi_{DEP}$>0) and then at even higher frequencies exhibits gradually decreasing values for $\chi_{DEP}$. In this frequency range, the cell exhibits negative values for the traveling wave dielectrophoretic polarization factor ($\zeta_{TW\text{-}DEP}$<0). The exact frequency ranges for these different regimes of dielectrophoresis and traveling wave dielectrophoresis polarization factors depend on the cell's dielectric properties and the electrical conductivity of the solution in which the cells are suspended.

Some cells, notably bacterial, fungal, and plant cells, have a cell wall in addition to a cell membrane. The dielectric properties of such complex particles are complex, with the electrical permittivities and conductivities of each of the cell wall, cell membrane, and cell interior dominating the dielectrophoretic behavior of the cells at particular field frequencies. The determination of electrical properties of the cell walls of micro-organisms and the dielectrophoretic behavior of cell wall-containing micro-organisms is described in Markx et al. (Microbiology 140: 585-591 (1994)).

The overall size of a particle or a component of a sample also determines its response to an electric field, and thus is herein considered a dielectric property. A sample component's conductivity, permittivity, or size, or any combination of these properties, can be altered by a solution of the present invention.

Electrode arrays can be used to test behavior of particles in suspending solution or media. For example, positive or negative dielectrophoresis of particles can be observed after applying an electric field. For example, a particle suspended in solution can be pipetted onto a polynomial electrode array and a sinusoidal signal at certain frequencies (for example, between about 10 Hz to about 500 MHz) and at certain magnitude (<20 V peak-to-peak) can be applied to the electrodes. Particles that experience positive dielectrophoresis collect at the electrode edges, while components that experience negative dielectrophoresis collect at the central region between the electrodes (Huang and Pethig, Meas. Sci. Technol. 2: 1142-1146 (1991).

Tests for manipulation or positioning of particles by dielectrophoresis can use detectable labels, where at least one particle in a sample is detectably labeled. For example, a biological sample having a population of particles such as cells can be subjected to a dielectrophoretic manipulation procedure, one cell type can be labeled using antibodies that recognize that cell type and not other cell types or components of the sample. The antibodies can be bound to a detectable label, such as, for example, a fluorescent molecule, such as rhodamine, fluorescein, Texas red, phycoerythrin, phycocyanin, green fluorescent protein, cyan fluorescent protein, blue fluorescent protein, yellow fluorescent protein, D.s. red protein, etc. Another cell type can optionally be labeled with a different antibody and a different detectable label. In this way, the positions of the cells carrying the fluorescent labels can be visualized and the quality of dielectrophoretic separation using a buffer of the present invention can be assessed.

The dielectric manipulation and positioning of particles such as cells can also be monitored by loading cells with detectable labels, such as dyes, as they are known in the art. For example, cells can be loaded with BCECF-AM (available from Molecular Probes, Eugene, Oreg.) a flourescein probe that can be taken up by viable cells and there position after dielectric positioning can be determined (Gascoyne et al. IEEE Transcactions 33:670-678 (1997)). A chip on which positioning of particles such as cells has been tested can be viewed microscopically.

Separation, manipulation or positioning of particles in a sample in a chamber can occur through the application of a non-uniform electric field. Preferably, separation, manipulation or positioning of particles occurs on a chip that is part of a chamber, and application of the non-uniform electric field can be by means of controls that are external to a chamber and a chip. One or more power sources or electrical signal generators, which may be capable of varying voltage, frequency, phase, or any combination thereof, can transmit at least one electrical signal to one or more electrodes to create a spatially non-homogeneous alternating electric field. The voltage applied to the electrodes can be in the range of from about 0 to about 100 volts, more preferably from about 0 to about 15 volts, and the frequency of the electrical signal can be in the range of from about 0.01 kHz to about 500 MHz, and preferably from between about 1 kHz to about 20 MHz. These frequencies are exemplary only, as the frequency of the separation, manipulation or positioning of particles will depend upon a dielectric property of the particles to be separated, manipulated or positioned and the conductivity of the solution the particles are suspended in.

Separation, manipulation or positioning of particles by dielectrophoretic forces can occur by any dielectrophoretic mechanism, for example, by dielectrophoretic retention, dielectrophoretic migration, dielectrophoretic/gravitational field flow fractionation, or traveling wave dielectrophoresis-based separation, or 2-D dielectrophoresis. The following examples of separations, manipulations or positionings are given by way of illustration, and not by way of limitation. Dielectrophoretic retention can be employed, in which the particle is selectively retained in one or more areas of the chamber and other components of the sample are optionally washed out of the chamber by fluid flow. In a different approach of dielectrophoretic migration, one or more particles can be dielectrophoretically translocated to one or more areas of a chip and one or more other components of a sample can be dielectrophoretically repelled from those areas. It is also possible to effect a dielectric separation, manipulation or positioning using dielectrophoretic/gravitational field flow fractionation, in which different particles are levitated to different heights, or in which one or more particles is levitated while other particles are directed to one or more locations on the chip, and fluid flow through the chamber comprising the chip carries different sample components out of the chip at different speeds. It is also possible to direct one or more particles out of the chamber using traveling wave dielectrophoresis, to effect a separation, manipulation or positioning from the other components. It is also possible to use 2-dimensional dielectrophoresis in which both dielectrophoretic forces and traveling-wave dielectrophoretic forces are exploited for separation, manipulation or positioning of one or more particles from a sample (De Gasperis et al., Biomedical Microdevices 2: 41-49 (1999)).

Because a sample can comprise components whose behaviors in various dielectric field patterns is unknown, separation of moieties can be achieved and optimized by altering such parameters as electrode geometry, electric field magnitude, and electric field frequency.

The separation can be achieved by collecting and trapping the positive dielectrophoresis-exhibiting moieties on electrode edges while removing other cells with forces such as fluidic forces. Similar methods may be applied for the case of using negative dielectrophoresis-exhibiting particles for selective separation of target cells from cell mixtures where most or many cell types exhibit positive dielectrophoresis. In aspects where dielectrophoretic/gravitational field-flow fractionation, traveling wave dielectrophoresis, or 2-dimensional dielectrophoresis is used, the separation can be achieved by collecting fractions of the sample-sample solution mixture as they "elute" or flow out of, a chamber experiencing fluid flow and dielectrophoretic forces.

There are a number of dielectrophoretic methods for separating and manipulating cells, bioparticles and moieties from a sample mixture. These methods include, but not limited to, dielectrophoretic migration, dielectrophoretic retention, dielectrophoretic/gravitational field flow fractionation, traveling-wave dielectrophoresis, and 2-D dielectrophoresis. Those who are skilled in the art of dielectrophoretic manipulation and dielectrophoretic separation may readily use and apply these methods for separating moieties of interest from a mixture in combination with the sample solution of the present invention. The following articles provide detailed descriptions of a number of dielectrophoretic manipulation and dielectrophoretic separation methods: Wang, et al., *Biochim. Biophys. Acta.* 1243:185-194 (1995), Wang, et al., *IEEE Trans. Ind. Appl.* 33:660-669 (1997) (various electrode structures, manipulation by dielectrophoresis and traveling wave dielectrophoresis); Wang, et al., *Biophys. J* 72:1887-1899 (1997) (concentration, isolation and separation using spiral electrodes using traveling wave dielectrophoresis); Wang, et al., *Biophys. J.* 74:2689-2701 (1998), Huang, et al., *Biophys. J.* 73:1118-1129 (1997) and Yang, et al., *Anal. Chem.* 71(5):911-918 (1999) (levitation, repulsion from electrodes and separation by dielectrophoretic/gravitational field-flow-fractionation); Gascoyne, et al., *IEEE Trans. Ind. Apps.* 33(3):670-678 (1997), Becker, et al., *Proc. Natl. Acad. Sci. USA* 92:860-864 (1995) and Becker, et al., *J. Phys. D: Appl. Phys.* 27:2659-2662 (1994) (trapping, repulsion, redistribution and separation, separation by dielectrophoretic migration, separation by dielectrophoresis retention); Huang, et al., *J. Phys. D: Appl. Phys.* 26:1528-1535 (1993) (transportation, separation and trapping by traveling-wave-dielectrophoresis); and Wang, et al., *J. Phys. D: Appl. Phys.* 26:1278-1285 (1993) (trapping, separation and repulsion, separation by dielectrophoretic migration). All the above cited papers are incorporated in the present application by reference. Other examples of manipulation and separation methods that are reported in the literature and may be adapted for manipulating moieties using the present methods include: separation of bacteria from blood cells, and of different types of microorganisms (Hawkes, et al., *Microbios.* 73:81-86 (1993); and Cheng, et al., *Nat. Biotech.* 16:546-547 (1998)); enriching CD34+ stem cells from blood (Stephens, et al., *Bone Marrow Transplantation* 18:777-782 (1996)); DEP collection of viral particles, sub-micron beads, biomolecules (Washizu, et al., *IEEE Trans. Ind. Appl.* 30:835-843 (1994); Green and Morgan, *J. Phys. D: Appl. Phys.* 30:L41-L44 (1997); Hughes, et al., *Biochim. Biophys. Acta.* 1425:119-126 (1998); and Morgan, et al., *Biophys J.* 77:516-525 (1999)); dielectrophoretic levitation for cell characterization (Fuhr, et al., *Biochim. Biophys. Acta.* 1108:215-233 (1992)); single-particle homogeneous manipulation (Washizu, et al., *IEEE Trans. Ind. Appl.* 26:352-358 (1990); Fiedler, et al., *Anal. Chem.* 70:1909-1915 (1998); and Müller, et al., *Biosensors and Bioelectronics* 14:247-256 (1999)); dielectrophoretic field cages (Schnelle, et al., *Biochim. Biophys. Acta.* 1157:127-140 (1993); Fiedler, et al. (1995); Fuhr, et al. (1995a); Fiedler, et al. (1998); Müller, et al. (1999)); traveling-wave DEP manipulation of cells with linear electrode arrays (Hagedorn, et al., *Electrophoresis* 13:49-54 (1992); Fuhr, et al., *Sensors and Actuators*

A: 41:230-239 (1994); and Morgan, et al., *J. Micromech. Microeng.* 7:65-70 (1997)) All the above cited papers are incorporated in the present application by reference.

Dielectric Focusing Structures

Dielectric focusing structures refer to any electrode structure elements fabricated or machined onto a chip substrate that have the following properties. These electrode elements can produce electric fields in the spaces around the chip when they are connected with and energized with electrical signals. Such electric fields may be non-uniform AC electric fields, traveling-wave electric fields, or non-uniform traveling wave electric fields, or electric fields of any other configuration. These electric fields preferably can exert dielectrophoretic forces and traveling wave dielectrophoretic forces the particles that are suspended or placed in the solutions that are in contact with the electrode elements. Such dielectrophoretic and/or traveling-wave dielectrophoretic forces can then direct or focus or move the particles onto certain specific locations.

In operation, a fluidic chamber is first constructed that includes a biochip of the present invention. A sample that includes particles such as cells is introduced into the chamber. The appropriate electrical signals are applied to the electrodes to produce an electrical field that exert dielectrophoretic and traveling-wave dielectrophoretic forces that can direct or focus or move the particles to the specific locations on the chip. Those locations correspond to the positions at which the ion-channel means are located.

Non-limiting examples of the dielectric focusing structures include spiral electrode structures, circular electrode structures, squared spiral electrode structures, traveling wave dielectrophoresis structures, particle switch structures, quadropole electrode structures, and electrorotation structures.

Spiral electrode structures include multiple, parallel, linear spiral electrode elements. For example, the structure can include three, four, five or even more, parallel, linear spiral elements. AC electrical signals of same frequency, but different phases are applied to these multiple electrode elements to generate a traveling wave electric field towards or away from the center of the electrode array. In order to produce such traveling wave electric field, phases of the signals applied to these electrode elements should be 0, 360/N, 2*360/N, . . . (N−1)*360/N, where N is the number of the spiral elements. The structure and operational principle of a spiral electrode array (N=4) is described in "Dielectrophoretic manipulation of cells using spiral electrodes by Wang et al., *Biophys. J.*, 72:1887-1899 (1997)", which is incorporated in its entirety by reference.

In operation, a fluidic chamber is first constructed that includes a biochip having a spiral electrode structure. A sample that includes particles such as cells is introduced into the chamber. The electrical signals of appropriate phase, voltage and frequencies are applied to the electrodes to produce an electrical field that exert dielectrophoretic and traveling-wave dielectrophoretic forces that can direct or focus or move the particles to the center regions of the spiral electrode elements. The details for choosing such operation conditions for the maximum response effects in a 4-phase spiral electrode system are described and discussed in "Dielectrophoretic manipulation of cells using spiral electrodes by Wang et al., *Biophys. J,* 72:1887-1899 (1997)". Based on the details on this article, those who are skilled in dielectrophoresis and traveling-wave dielectrophoresis can readily choose the operation conditions for other spiral electrode structures with different numbers of the parallel elements. An ion-channel measuring means is located at the central region of the spiral electrode structures. For example, a hole of appropriate size and geometry is at the center of the spiral electrode. After the particles are moved or focused to the center of the spiral electrodes and over the hole at the center of the spiral electrode elements, appropriate electrophysiology measurements are performed on the particles to determine the electrical functions and properties of the ion channels (or ion transporters or other proteins or non-peptide entity that permit the passage of the ions) on the surface of the particles.

Concentric circular electrodes are electrode structures that include multiple concentric circular electrode elements. The circular electrode elements are connected to external signal source through electrode lines cutting cross these circular elements. These electrode lines have to be fabricated into a different layer on the chip and have to be isolated from the circular elements. In order to produce a traveling electric field, the electrical signals applied to the circular elements have to be phase-sequenced. For example, the signals with the phase values of 0, 90, 180, 270 can be applied sequentially to the circular elements. If we number the circular elements from outermost element (as No. 1) to the innermost as 1, 2, 3, 4, 5, 6, . . . , then the electrode elements 1, 5, 9, . . . etc are connected with 0 phase signal, the elements 2, 6, 10, . . . etc are connected with 90 phase signal, the elements 3, 7, 11, . . . etc are connected with 180 phase signal, the elements, 4, 8, 12, . . . etc are connected with 270 phase signals. Other phase combinations can be used and applied so long as a complete phase sequence (0 to 360 degree) can be established over the electrode elements. For example, signals having phase values of 0, 120 and 240 degrees can be used to energize three neighboring electrode elements.

The operational principle of the concentric circular electrodes is similar to the spiral electrode elements (see, Wang et al., "Dielectrophoretic manipulation of cells using spiral electrodes by Wang et al., *Biophys. J,* 72:1887-1899 (1997)".

In operation, a fluidic chamber is first constructed including a biochip having a concentric electrode structure. A sample that includes particles such as cells is introduced into the chamber. The electrical signals of appropriate phase, voltage and frequencies are applied to the electrodes to produce an electrical field that exert dielectrophoretic and traveling-wave dielectrophoretic forces that can direct or focus or move the particles to the center regions of the concentric electrodes. The details as for how to choose such operation conditions for the maximized response effects in a 4-phase spiral electrode structure are described and discussed in "Dielectrophoretic manipulation of cells using spiral electrodes by Wang et al., *Biophys. J.,* 72:1887-1899 (1997)". Based on the details on this article, those skilled in dielectrophoresis and traveling-wave dielectrophoresis can readily choose the operation conditions for the concentric electrode structures. An ion-channel measuring means is located at the central region of the concentric electrode elements. For example, a hole of appropriate size and geometry is at the center of the concentric electrode structure. After the particles are moved or focused to the center of the spiral electrodes and over the hole at the center of the concentric circular electrode elements, appropriate electrophysiology measurements are performed on the particles to determine the electrical functions and properties of the ion channels (or ion transporters or other proteins or non-peptide entity that permit the passage of the ions) on the surface of the particles.

Squared-spiral electrodes are electrode structures that include multiple squared-spiral electrode elements. The operation principle of the squared-spiral electrodes is similar to that of a spiral electrode structure, and the traveling wave dielectrophoretic forces produced by the squared spiral electrodes are directed to be normal the linear electrode segments in these electrode elements.

In operation, a fluidic chamber is first constructed including a biochip having a squared-spiral electrode structure. A sample that includes particles such as cells is introduced into the chamber. The electrical signals of appropriate phase, voltage and frequencies are applied to the electrodes to produce an electrical field that exert dielectrophoretic and traveling-wave dielectrophoretic forces that can direct or focus or move the particles to the center regions of the squared-spiral electrode structures. The details as for how to choose such operation conditions for the maximized response effects in a 4-phase spiral electrode structure are described and discussed in "Dielectrophoretic manipulation of cells using spiral electrodes by Wang et al., *Biophys. J.*, 72:1887-1899 (1997)". Based on the details on this article, those skilled in dielectrophoresis and traveling-wave dielectrophoresis can readily choose the operation conditions for the squared-spiral structures. An ion-channel measuring means is located at the central region of the squared-spiral electrode elements. For example, a hole of appropriate size and geometry is at the center of the squared-spiral electrode structure. After the particles are moved or focused to the center of the squared spiral electrodes and over the hole at the center of the squared-spiral electrode elements, appropriate electrophysiology measurements are performed on the particles to determine the electrical functions and properties of the ion channels (or ion transporters or other proteins or non-peptide entity that permit the passage of the ions) on the surface of the particles.

Traveling Wave Dielectrophoresis Structures

Traveling wave dielectrophoresis structure generally refers to an electrode structure that can produce traveling wave electric fields and exert traveling wave dielectrophoresis forces on the particles. Examples of the traveling wave dielectrophoresis structures include, but not limited to, the spiral electrode structure, the squared electrode structure and the concentric circular electrode structures, particle switch structures. Another example of the traveling wave dielectrophoresis structures is a set of linear, parallel electrodes that can be energized with phase-sequenced signals and can induce traveling electric fields. A number of traveling wave dielectrophoresis structures are disclosed and described on the co-pending U.S. applications (Ser. No. 09/678,263), titled "AN APPARATUS FOR SWITCHING AND MANIPULATING PARTICLES AND METHOD OF USE THEREOF" by Wang et al., filed on Oct. 3, 2000, which is incorporated by reference in its entirety. Those electrode structures can be utilized for the manipulation and positioning of particles such as cells and cell fragments for ion channel or ion transport measurement described in this application. An ion-channel measuring means (or a means to measure electrical responses of ion channels, ion transporters and any other molecules or entities that permit ion passage across an enclosed membrane envelope or across a spread-out membrane area) is located at appropriate locations in respect to the traveling wave dielectrophoresis structures. For example, it is preferred that the ion channel measuring means are located at the regions where the particles can be manipulated into when appropriate electrical signals are applied.

In one specific embodiment, traveling wave dielectrophoresis structures take the form of a set of linear, parallel electrode elements. An ion-channel measuring means (or a means to measure electrical responses of ion channels, ion transporters and any other molecules or entities that permit ion passage across an enclosed membrane envelope or across a spread-out membrane area) is located on one end of the linear set of the electrodes. These structures are produced on a chip substrate. In the operation, a fluidic chamber is first constructed comprising this chip having the linear set of electrode elements. A sample that comprises particles such as cells is introduced into the chamber. The electrical signals of appropriate phases, voltages and frequencies are applied to the electrode elements to produce an electrical field that exert dielectrophoretic and traveling-wave dielectrophoretic forces that can direct or focus or move the particles to the end of the linear set of the electrodes (the end where an ion-channel measuring means is located). Those are skilled in dielectrophoresis and traveling-wave dielectrophoresis can readily choose the operation conditions for such linear parallel electrode structures. The ion channel measuring means, for example, may comprise a hole at the end of the linear set of the electrodes. After the particles are moved or focused to the center of the spiral electrodes and over the hole at the end of the linear electrode elements, appropriate electrophysiology measurements are performed on the particles to determine the electrical functions and properties of the ion channels (or ion transporters or other proteins or non-peptide entity that permit the passage of the ions) on the surface of the particles.

Particle Switch Structures

Particle switching structures generally refer to an electrode structure that can transport, switch, and move the particles in certain directions defined by the traveling wave electric fields generated by such particle switching electrodes when electrical signals of appropriate phase. A number of example for the particle switching structures are provided in the co-pending U.S. patent application Ser. No. 09/678,263, titled "AN APPARATUS FOR SWITCHING AND MANIPULATING PARTICLES AND METHOD OF USE THEREOF" by Wang et al., filed on Oct. 3, 2000. The U.S. patent application Ser. No. 09/678,263 also disclosed methods for manipulation, transportation, separation and positioning of particles such as cells by applying appropriate electrical signals. An ion-channel measuring means (or a means to measure electrical responses of ion channels, ion transporters and any other molecules or entities that permit ion passage across an enclosed membrane envelope or across a spread-out membrane area) is located at appropriate locations in respect to the particle switching structures. For example, it is preferred that the ion channel measuring means are located at the regions where the particles can be manipulated into when appropriate electrical signals are applied.

In operation, a fluidic chamber is first constructed including a biochip having particle-switch electrode structures. A sample that includes particles such as cells is introduced into the chamber. The electrical signals of appropriate phase, voltage and frequencies are applied to the particle switch structures to produce an electrical field that exert dielectrophoretic and traveling-wave dielectrophoretic forces that can direct or focus or move the particles to certain locations of the particle switching electrode structures where the ion-channel measuring means is located. The co-pending U.S. patent application Ser. No. 09/678,263, entitled "AN APPARATUS FOR SWITCHING AND MANIPULATING PARTICLES AND METHOD OF USE THEREOF" by Wang et al., filed on Oct. 3, 2000, disclosed details of the choice of appropriate electrical conditions for moving and transporting particles. The ion channel measuring means, for example, may comprise a hole located at appropriate positions with respect to the particle switching electrode structures. After the particles are moved or focused to the regions of ion channel measuring means and over the hole, appropriate electrophysiology measurements are performed on the particles to determine the electrical functions and properties of the ion channels (or ion transporters or other proteins or non-peptide entity that permit the passage of the ions) on the surface of the particles.

Electromagnetic Strucutres

Magnetic particles that are capable of being translocated in response to magnetic field and to electromagnetic forces can comprise any magnetic material (such as $\gamma Fe_2O_3$ and $Fe_3O_4$, $\gamma Fe_2O_3$ is the $\gamma$-phase of $Fe_2O_3$). Paramagnetic particles are preferred whose dipoles are induced by externally applied magnetic fields and return to zero when the external field is turned off. Suitable paramagnetic materials include, for example, iron compounds. Magnetic materials can be combined with other materials, such as polymers, in or on magnetic particles. Surfaces of magnetic particles of the present embodiment can optionally be coated with one or more compounds to facilitate attachment of specific binding members or to promote direct or indirect binding of particles such as cells or target cells. Magnetic particles that can be used in the present invention can be of any shape. Preferably magnetic particles are spherical or ellipsoid, but this is not a requirement of the present invention. The use of magnetic particles is well known in the biological and biochemical separation arts, and magnetic particles, including magnetic particles coupled to a variety of specific binding members are also commercially available (Dynal Biotech, Lake Success, N.Y.).

More than one preparation of magnetic particles can be used in the methods of the present invention. In embodiments using more than one preparation of magnetic particles, different magnetic particles can have different surface properties, such that they can bind different particles in a sample. In this way, more that one type of particles can be separated or positioned using the methods of the present invention. Different surface properties of magnetic particles can be conferred, for example, by coating the magnetic particles with different compounds, or by reversibly or irreversibly linking different specific binding members to the surfaces of the magnetic particles.

The particles to be manipulated or positioned can be coupled to the surface of the binding partner such as magnetic particles with any methods known in the art. For example, the particles such as cells can be coupled to the surface of the binding partner (e.g. magnetic particles) directly or via a linker. The particle can also be coupled to the surface of the binding partner (e.g. magnetic particles) via a covalent or a non-covalent linkage. Additionally, the particle can be coupled to the surface of the binding partner (e.g. magnetic particles) via a specific or a non-specific binding. The linkage between the particle and the surface of the binding partner (e.g. magnetic particles) can be a cleavable linkage, for example, a linkage that is cleavable by a chemical, physical or an enzymatic treatment.

Linkers can be any particle suitable to associate the particle (e.g., cells or cell fragments) and the binding partner (e.g. magnetic particles). Such linkers and linkages include, but are not limited to, amino acid or peptidic linkages, disulfide bonds, thioether bonds, hindered disulfide bonds, and covalent bonds between free reactive groups, such as amine and thiol groups. Other linkers include acid cleavable linkers, such as bismaleimideothoxy propane, acid labile-transferrin conjugates and adipic acid dihydrazide, that would be cleaved in more acidic intracellular compartments; cross linkers that are cleaved upon exposure to UV or visible light and linkers, such as the various domains, such as $C_H1$, $C_H2$, and $C_H3$, from the constant region of human $IgG_1$ (Batra et al., *Molecular Immunol.*, 30:379-386 ((1993)). In some embodiments, several linkers may be included in order to take advantage of desired properties of each linker. Other linkers, include trityl linkers, particularly, derivatized trityl groups to generate a genus of conjugates that provide for release of the particle at various degrees of acidity or alkalinity (U.S. Pat. No. 5,612, 474). Additional linking particles are described, for example, in Huston et al., *Proc. Natl. Acad. Sci. U.S.A.*, 85:5879-5883 (1988), Whitlow, et al., *Protein Engineering*, 6:989-995 (1993), Newton et al., *Biochemistry*, 35:545-553 (1996), Cumber et al., *Bioconj. Chem.*, 3:397-401 (1992), Ladurner et al., *J. Mol. Biol.*, 273:330-337 (1997) and in U.S. Pat. No. 4,894,443. In some cases, several linkers may be included in order to take advantage of desired properties of each linker. The preferred linkages used in the present methods are those effected through biotin-streptavidin interaction, antigen-antibody interaction, ligand-receptor interaction, or nucleic complementary sequence hybridization. Linkers for binding a particle to a binding partner such as a microparticle and methods of coupling linkers to microparticles are further described in U.S. patent application Ser. No. 09/636,104, entitled "Methods for Manipulating Moieties in Microfluidic Systems", naming Xiaobo Wang, Lei Wu, Jing Cheng, Weiping Yang, and Junquan Yu as inventors and on filed Aug. 10, 2000 and corresponding PCT Application Number PCT/US00/25381, entitled "Method for Manipulating Moieties in Microfluidic Systems", filed Sep. 15, 2000, and naming Xiaobo Wang, Lei Wu, Jing Cheng, Weiping Yang, and Junquan Yu as inventors, and herein incorporated by reference in its entirety.

There are two general purposes for using magnetic particles in the present invention. The first is to bind to a particle (e.g. a cell containing ion channels in its plasma membrane) or target particle (e.g. a target cells within a cell mixture) to a magnetic particle for the purpose of separating the particle or target particle from other particles, such as in a population of particles in a sample mixture. The separation can be achieved using magnetic or electromagnetic elements, structures or means on, within or outside of a chip. The second is to position particles (e.g. the cells that contain ion channels in their plasma membranes) bound with magnetic particles in proximity of ion transport detection structures of the present invention. The positioning can be achieved using magnetic or electromagnetic elements, structures or means on, within or outside of a chip. In certain instances, the magnetic particles can aid in engaging a particle with such an ion transport detection structure. In one aspect of the present invention, particles (e.g. cells) are selectively attached to magnetic microparticles, such as through specific binding members, such as antibodies. The particles (e.g., cells) labeled with magnetic microparticles are then separated using electromagnetic elements of the present invention and can be manipulated or positioned at or near an ion transport detection structure. The particle (e.g. a cell) is engaged with such ion transport detection structure and ion transport function or properties can be determined.

In one aspect of the present invention, particles, such as cells, can express or over-express an exogenous surface peptide or over-express an endogenous surface protein, such as a cell surface marker not endogenous to the cell. A specific binding member bound to a magnetic particle would specifically bind with that cell and allow for that cell to be separated from a sample including a mixture of cells using electromagnetic elements. The magnetic particle bound to a particle (e.g. a cell) would also facilitate manipulation of the particle and positioning at or near an ion transport determination structure such as a hole or capillary. Particles such as cells having such cell surface markers can be made by introducing an expression vector into the cells. The expression vector would include a regulatory element such as a promoter operable in the host cell being used operably linked to a nucleic acid sequence encoding the exogenous or endogenous cell surface protein. Methods of making such constructs, introducing the vector into the cells and expression are known in the art.

In another aspect of the present invention, particles such as cells can co-express two proteins, one the exogenous cell surface marker or over-expressed endogenous cell surface marker discussed above and the second an exogenous ion transport protein or over-expressed endogenous ion transport protein. These particles such as cells thus express a surface marker that can be specifically bound with another particle such as a magnetic particle. These bound particles can be separated, manipulated and positioned with appropriate particle manipulation devices, such as magnetic, electromagnetic devices. The particles that are positioned in this way include the ion transport protein which can then be interrogated using structures and methods of the present invention.

In some cases, after manipulating or separating the particle-binding partner, for example, cell-magnetic microparticle, the binding partners do not interfere with reactions or measurements the particles (e.g. cells) are to be subsequently involved in. Thus, it may not be necessary to decouple the particles (e.g. cells) from the magnetic particles. However, in other cases, it may be desirable or necessary to decouple the particles (e.g. cells) from the magnetic particles after the manipulating step. The nature of the decoupling step depends on the nature of the particle, the particular magnetic particle, the surface modification of the magnetic particle, in particular the specific binding partner, linker, or coupling agent that may be on the magnetic particle, and the manipulation step. In some cases, the condition of the decoupling step is the opposite of the conditions that favor the binding between the particle and the magnetic particle. For example, if a particle binds to the magnetic particle at a high salt concentration, the particle can be decoupled from the magnetic particle at a low salt concentration. Similarly, if a particle binds to the magnetic particle through a specific linkage or a linker, the particle can be decoupled from the magnetic particle by subjecting the linkage to a condition or agent that specifically cleaves the linker.

Paramagnetic particles are preferred whose magnetic dipoles are induced by externally applied magnetic fields and return to zero when external field is turned off. For such applications, commercially available paramagnetic or other magnetic particles may be used. Many of these magnetic particles are between below micron (for example, 50 nm-0.5 micron) and tens of microns. They may have different structures and compositions. One type of magnetic particles has ferromagnetic materials encapsulated in thin latex, for example, polystyrene, and shells. Another type of magnetic particles has ferromagnetic nanoparticles diffused in and mixed with latex for example polystyrene, surroundings. The surfaces of both these particle types are polystyrene in nature and may be modified to link to various types of molecules.

Separations, manipulations or positioning of particles such as target cells using magnetic particles are performed on electromagnetic chips, where the source of the electromagnetic force is in part separate from the chip and in part integral to the chip. An electrical current source is external to an electromagnetic chip of the present invention, allowing the operator to control the electromagnetic force, whereas the electromagnetic elements are fabricated onto the chip. The electromagnetic elements can produce magnetic fields and exert electromagnetic forces on magnetic particles. The electromagnetic elements can be of various structural geometries. For example, the electromagnetic elements can be a loop of conducting material, such as metal, that goes around a ferromagnetic body and that can be sputtered, electroplated, or deposited on a chip. An electromagnetic chip can have one or more electromagnetic units as described in the U.S. patent application Ser. No. 09/399,299, filed Sep. 16, 1999, naming Zhou et al. as inventors, and U.S. patent application Ser. No. 09/685,410, filed Oct. 10, 2000, entitled "Individually Addressable Micro-Electromagnetic Unit Array Chips in Horizontal Configurations" and naming Lei Wu, Xiaobo Wang, Jing Cheng, Weiping Yang, YuXiang Zhou, LiTian Liu, and JunQuan Xu as inventors, both herein incorporated by reference. For use of these electromagnetic chips for characterizing the ion channel responses in the method of the present invention, these electromagnetic chips may further comprise ion transport detection (or measuring) means. The ion transport detection structures are fabricated or made at appropriate locations with respect to the electromagnetic elements.

Other examples of such electromagnetic elements include, but not limited to, those described in the following articles such as Ahn, C., et al., *J. Microelectromechanical Systems.* Volume 5: 151-158 (1996); Ahn, C., et al., *IEEE Trans. Magnetics.* Volume 30: 73-79 (1994); Liakopoulos et al., in *Transducers 97*, pages 485-488, presented in 1997 International Conference on Solid-State Sensors and Actuators, Chicago, Jun. 16-19, 1997; U.S. Pat. No. 5,883,760 by Naoshi et al. The above publications are incorporated in the present application by reference. These publications, and the co-pending U.S. patent application Ser. No. 09/399,299, filed Sep. 16, 1999, and the and the U.S. Patent with docket number ART-00104.P.1.1, filed Oct. 10, 2000, entitled "Individually Addressable Micro-Electromagnetic Unit Array Chips in Horizontal Configurations" and naming Lei Wu, Xiaobo Wang, Jing Cheng, Weiping Yang, YuXiang Zhou, LiTian Liu, and JunXuan Xu, as inventors, both herein incorporated by reference, further disclose the materials, methods and protocols that may be used to fabricate the electromagnetic structures on a chip.

The electromagnetic chip can be fabricated on a number of materials such as ceramics, polymers, copolymers, plastics, rubber, silicon, or glass. An electromagnetic chip can be from about 1 mm$^2$ to about 0.25 m$^2$. Preferably, the size of the chips useable in the present methods is from about 4 mm$^2$ to about 25 cm$^2$. The shape of the chips useable in the present methods can be regular shapes such as square, rectangular, circular, or oval, or can be irregularly shaped. Chips useable in the methods of the present invention can have one or more wells or one or more channels that can be etched or bored into a chip or built onto the surface of a chip. For use of these electromagnetic chips for characterizing the ion channel responses in the method of the present invention, these electromagnetic chips may further comprise ion transport detection (or measuring) means. The ion transport detection structures are fabricated or made at appropriate locations with respect to the electromagnetic elements.

An electromagnetic chip can be a part of a chamber, where a chamber is structure capable of containing a fluid sample. A chamber can comprise any fluid-impermeable material, for example, silicon, glass, metal, ceramics, polymers, plastics, acrylic, glass, etc. Preferred materials for a chamber include materials that do not interfere with electromagnetic manipulation of particles in a sample. The chamber can also include an ion transport-measuring device or element.

A chamber that comprises an electromagnetic chip with an ion-transport detection means useable in the methods of the present invention can comprise one or more ports, or openings in the walls of a chamber. Preferably, a port is of a shape and size that allows a conduit to engage a port for the dispensing of a sample into the chamber. A conduit can be any tube that allows for the entry of a fluid sample into the chamber. Preferred conduits for use in the present invention include tubing, for example, rubber or polymeric tubing, e.g., tygon or teflon or PEEK tubing. Alternatively, a port can provide an opening in a wall of a chamber for the dispensing of sample into the chamber by, for example, pipetting or injection.

Conduits that engage one or more ports of the sample can introduce a sample by means of a pump (for example, a peristaltic pump or infusion pump), pressure source syringe, or gravity feed. One or more reagents, buffers, or solutions, including, but not limited to, a population of magnetic particles, can be added to the chamber before, after, or concurrently with the addition of a sample to a chamber. It is also within the scope of the invention to mix the sample with a reagent, buffer, or solution, before adding the sample to the chamber. Such mixing can optionally occur in one or more conduits leading to a chamber, or in one or more reservoirs connected to conduits.

The chamber can be of any size or dimensions, and preferably can contain a fluid sample of between 0.001 microliter and 50 milliliters, more preferably between about 1 microliters and about 20 milliliters, and most preferably between about 10 microliters and about 10 milliliters. A chamber can comprise any suitable material, for example, silicon, glass, metal, ceramics, polymers, plastics, etc. and can be of a rigid or flexible material.

It is necessary to point out that for chambers with large volumes (up to 50 mL), chips of special geometries and configurations may have be used. The chips may be fabricated on flexible materials so that the chips can be folded to form tube like chambers. Multiple chips may be configured into a same chamber. The electromagnetic elements may have to have certain configurations so that effective electromagnetic forces may be generated in the region of the interest in the chamber.

The manipulation and positioning of particles such as target cells on an electromagnetic chip requires the magnetic field distribution generated over microscopic scales. One approach for generating such magnetic fields is the use of microelectromagnetic units. Such units can induce or produce magnetic field when an electrical current is applied. The on/off status and the magnitudes of the electrical current applied to these units will determine the magnetic field distribution. The structure and dimension of the microelectromagnetic units may be designed according to the requirement of the magnetic field distribution. The examples of the electromagnetic units include, but not limited to, those described in the following articles such as Ahn, C., et al., *J. Microelectromechanical Systems.* Volume 5: 151-158 (1996); Ahn, C., et al., *IEEE Trans. Magnetics.* Volume 30: 73-79 (1994); Liakopoulos et al., in *Transducers* 97, pages 485-488, presented in 1997 International Conference on Solid-State Sensors and Actuators, Chicago, Jun. 16-19, 1997; U.S. Pat. No. 5,883,760 by Naoshi et al. Other examples of the electromagnetic units are provided in the co-pending U.S. patent application Ser. No. 09/399,299, filed Sep. 16, 1999, and the U.S. Patent 6,716,642, filed Oct. 10, 2000, entitled "Individually Addressable Micro-Electromagnetic Unit Array Chips in Horizontal Configurations" and naming Lei Wu, Xiaobo Wang, Weiping Yang, YuXiang Zhou, LiTian Liu, and JunXuan Xu as inventors, both herein incorporated by reference.

Manipulation and positioning of particles includes the directed movement, focusing and trapping of magnetic particles. The motion of magnetic particles in a magnetic field is termed "magnetophoresis". Theories and practice of magnetophoresis for cell separation and other applications may be found in various literatures (for example, Magnetic Microspheres in Cell Separation, by Kronick, P. L. in Methods of Cell Separation, Volume 3, edited by N. Catsimpoolas, 1980, pages 115-139; Use of magnetic techniques for the isolation of cells, by Safarik I. And Safarikova M., in J. of Chromatography, 1999, Volume 722(B), pages 33-53; A fully integrated micromachined magnetic particle separator, by Ahn C. H. et al., in J. of Microelectromechanical systems, 1996, Volume 5, pages 151-157). Use of are electromagnetic chip to separate, manipulate or position particles bound to magnetic particles is disclosed in U.S. patent application Ser. No. 09/399,299, filed Sep. 16, 1999, naming Zhou et al. as inventors, and U.S. patent application Ser. No. 09/685,410, filed Oct. 10, 2000, entitled "Individually Addressable Micro-Electromagnetic Unit Array Chips in Horizontal Configurations" and naming Lei Wu, Xiaobo Wang, Jing Chen, Weiping Yang, YuXiang Zhou, LiTian Liu, and JunXuan Xu as inventors, both herein incorporated by reference.

Micro-electromagnetic units are fabricated on substrate materials and generate individual magnetic fields when electric currents are applied. One example of the unit is a single loop of electrical conductor wrapped around a ferromagnetic body or core and connected to an electric current source through electronic switches. Such a loop may be a circle, ellipse, spiral, square, triangle or other shapes so long as a flow of electric current can be facilitated around the ferromagnetic body. If the loop is single, it should be complete or nearly complete. The loop may be in the form of a plurality of turns around the ferromagnetic body. The turns may be fabricated within a single layer of the microstructure, or, alternatively, each turn may represent a separate layer of the structure. The electric conductor may be a deposited conductive trace as in a electroplated, sputtered or deposited metallic structure, or the conductor can be formed within a semiconductor layer through selective doping. A preferred arrangement of array of a plurality of micro-electromagnetic units has a column and row structure of the form common in microelectronics. That is, the columns and rows are mutually perpendicular although the columns and rows can readily be offset at different angles (for example 80 degrees). For use of the electromagnetic chips for characterizing the ion channel responses in the methods of the present invention, the electromagnetic chips may further comprise ion transport detection (or measuring) means at appropriate locations with respect to the electromagnetic elements.

Other Structures

Quadropole Electrode Structures

Quadropole electrode structures refer to a structure that include four electrodes that are arranged around a locus such as a hole or capillary or a needle on or within a biochip or chamber. Appropriate electrical signals can be applied to such an electrode structure to produce dielectrophoretic forces on particles or the cells. For example, negative dielectrophoretic forces can be produced so that the particles are directed away from the electrode elements to the central regions between the electrode structures. An ion-channel measuring means (or a means to measure electrical responses of ion channels, ion transporters and any other molecules or entities that permit ion passage across an enclosed membrane envelope or across a spread-out membrane area) is located at appropriate locations in respect to the quadropole electrode structures. For example, it is preferred that the ion channel measuring means are located at the central regions between the quadropole electrode structures so that particles can be manipulated and positioned onto the central regions between the electrode structures. A number of quadropole electrode structures have been disclosed in the U.S. patent applications (Ser. No. 09/643,362), titled "APPARATUS AND METHOD FOR HIGH THROUGHPUT ELECTROROTATION ANALY- SIS", filed on Aug. 22, 2000, naming Jing Cheng et al. as inventors, which is incorporated by reference in its entirety. It is particularly important to know that an array of quadropole electrode structures, coupled with appropriate ion-channel measuring means can be fabricated and produced on a single chip so that a number of individual cells or particles, which are located in each quadropole electrode structure, can be assayed and analyzed simultaneously with ion-channel measuring means. All the electrode structures described in this applications such as spiral electrode structures, circular electrode structures, squared spiral electrode structures, traveling wave dielectrophoresis structures, particle switch structures, quadropole electrode structures, electrorotation structures, dielectric focusing structures and other electrode structures that are not described here but with the capabilities for moving and directing particles or cells to certain defined locations can be fabricated into an array format on a biochip. Each of these electrode structure units within the array has an associated ion-channel measuring means structure. Such a biochip can be utilized for assaying and analyzing the functions and properties of ion channels or other ion-passage proteins or non-peptide entities that are located on in a number of individual cells or other particles.

In operation, a fluidic chamber is first constructed including a biochip supporting a quadropole electrode structure. A sample that includes particles such as cells is introduced into the chamber. The electrical signals of appropriate phase, voltage and frequencies are applied to the quadropole electrode structures to produce an electrical field that exert dielectrophoretic forces that can direct or focus or move the particles to certain locations of the quadropole electrode structures where the ion-channel measuring means is located. For example, particles can be directed to the central regions between the quadropole electrode elements. The ion channel measuring means, for example, may comprise a hole located at the center between the quadropole electrode structures. After the particles are moved or focused to the center regions and over the hole, appropriate electrophysiology measurements are performed on the particles to determine the electrical functions and properties of the ion channels (or ion transporters or other proteins or non-peptide entity that permit the passage of the ions) on the surface of the particles.

Electrorotation Structures

Electrorotation structures refer to a structure that include four or more electrodes that are arranged around a locus such as a hole or capillary or a needle on or within a biochip or chamber. The electrorotation structure can produce a rotating electric field. Preferred electrorotation structures include a plurality of electrodes that are energized using phase-offset signals, such as 360/N degrees, where N represents the number of the electrodes in the electrorotation structure. A number of the electrorotation structures are disclosed in the U.S. patent application ( Ser. No. 09/643,362) entitled "APPARATUS AND METHOD FOR HIGH THROUGHPUT ELECTROROTATION ANALYSIS", filed on Aug. 22, 2000, naming Jing Cheng et al. as inventors. A rotating electrode structure can also produce dielectrophoretic forces for positioning the particles the certain locations, such as the center between the electrodes, under appropriate electrical signals or excitations. For example, when N=4 and electrorotation structure corresponds to a quadropole electrode structure. For producing rotating electric field, phase-offset signals are needed to apply to the electrodes. For producing dielectrophoretic forces for positioning particles such as cells, either phase-offset signals or regular AC electric signals can be applied to the electrodes. When negative dielectrophoretic forces are used for positioning particles, particles are positioned to the central region between the electrode structures. When positive dielectrophoretic forces are used for positioning the particles, particles are positioned to the electrode edges. Thus, depending on which type of dielectrophoretic forces are used to position particles, the structures within an ion-channel measuring means are located on either the regions between the electrode structures or close to the electrode edges. An array of electrorotation electrode structures, coupled with appropriate ion-channel measuring means can be fabricated and produced on a single chip so that a number of individual cells or particles, which are positioned into each electrorotation electrode structure, can be assayed and analyzed simultaneously with ion-channel measuring means. The U.S. patent application ( Ser. No. 09/643,362) entitled "APPARATUS AND METHOD FOR HIGH THROUGHPUT ELECTROROTATION ANALYSIS", filed on Aug. 22, 2000, naming Jing Cheng et al as inventors, disclosed a number of types of electrorotation electrode structure array.

In operation, a fluidic chamber is first constructed including a biochip supporting an electrorotation electrode structure. A sample that includes particles such as cells is introduced into the chamber. The electrical signals of appropriate phase, voltage and frequencies are applied to the electrorotation electrode structures to produce an electrical field that exert dielectrophoretic (and traveling-wave dielectrophoretic forces) that can direct or focus or move the particles to certain locations within the electrorotation electrode structures where the ion-channel measuring means is located. For example, particles can be directed to the central regions between the electrorotation electrode elements. The ion channel measuring means, for example, may comprise a hole located at the center between the electrorotation electrode structures. After the particles are moved or focused to the center regions and over the hole, appropriate electrophysiology measurements are performed on the particles to determine the electrical functions and properties of the ion channels (or ion transporters or other proteins or non-peptide entity that permit the passage of the ions) on the surface of the particles.

In some embodiments, it may be preferred that a number of concentric independent quadropole or electrorotation electrode structure unit can be used as the particle positioning means. In such a case, the particles will be positioned first by the outer quadropole electrode structure, moving to the central region between these outer electrode structures. The particles will then be further positioned with improved accuracy by other inner electrode structures. In an example of three concentric quadropole electrode structures, continuous positioning procedures can be undertaken, for example, first the outermost electrode structure, then by the second outermost electrode structure, and finally by the innermost electrode structure.

All the electrode structures described in this application (for example spiral electrode structures, circular electrode structures, squared spiral electrode structures, traveling wave dielectrophoresis structures, particle switch structures, quadropole electrode structures, electrorotation structures, dielectric focusing structures) and other electrode structures that are not described here can be utilized for cell separation purposes with appropriate electrical signals applied onto them. Various dielectrophoresis separation techniques can be employed. Thus one embodiment of the biochip may comprise the following elements, a dielectrophoresis separation electrode structure, a particle positioning means, and an ion channel measuring means. The dielectrophoresis separation electrode structures can be coupled to the particle positioning means so that the target particles, after being separated from an original mixture sample on a dielectrophoresis separation electrode structure, can be positioned and manipulated to specific desired locations for ion channel measurement (or ion transport assay or other assays that are for determining the electrical properties and functions of ion passage proteins or entities that are located on the particle surfaces). Non-limiting examples of integrating the dielectrophoresis separation electrode structures and a particle switching structure (for positioning and transporting particles) can be found in the co-pending U.S. patent application Ser. No. 09/678,263, entitled "AN APPARATUS FOR SWITCHING AND MANIPULATING PARTICLES AND METHOD OF USE THEREOF" by Wang et al., filed on Oct. 3, 2000. Those who are skilled in dielectrophoresis and traveling wave dielectrophoresis can readily design various electrode structures that can be used for as dielectrophoresis separation electrode structures and particle positioning means.

DC Electric Field Induced Fluid Motion Structures

DC electric field induced fluid motion structures. When a DC electric is applied to a solution, under certain conditions, a fluid motion can be induced. For example, a DC electric field across a thin channel can cause fluid motion within the channel if the channel wall has appropriate charge distributions. Such a fluid motion could be an electroosmosis effect or electrophoretic effect. In another example, DC electric field may result in certain electrohydrodynamic effects. These electrohydrodynamic effects may result in the interaction between the applied DC electric field and the volume charges within the fluid. Such DC electric field induced fluid motion can be used for moving, transporting and manipulating and positioning particles.

In one example, a DC electric field induced fluid motion structure can be used for enhancing the sealing between the particle surface and the ion transport measuring means. For simplicity, we discuss an example in which the particles that are being analyzed are mammalian cells. The ion transport measuring means in this example is a hole that is etched through the chip substrate, as exemplified in FIG. 1 and FIG. 2. An individual cell in the solution placed in chamber comprising the chip is positioned above the hole with various positioning means. For example, quadropole electrodes may be used to push the cell into the region between the four electrodes within the quadropole electrode structure.

After the cell positioning means moves the cell onto the hole, a DC electric field is produced in the hole so that a fluidic motion is produced in the hole. The fluidic flow is along the direction from the top to the bottom. Such a flow in the hole would result in a net pulling force on the cell so that the cell is pulled into the hole. During this process, a gradual sealing between the cell membrane and the hole on the chip occurs. Such a sealing will be monitored through the measurement of the total impedance between the solution over the chip and the solution below the chip. Depending on the specific electrophysiology measurement approach, certain impedance values may be required for achieving electronic sealing tight enough so that small electronic noises are produced. This process is similar to the electronic sealing procedure of the cell membrane onto a glass pipette tip that is widely used in electrophysiological ion channel recording.

After the appropriate electronic sealing is achieved, various measurement methods can be implemented to recording the ion channel responses. Specific measurement methods utilized will depend on the type of ion channels and depend on whether single- channel or whole-cell recording is used, and depend on what functions or properties the measurements are targeted for. Those who are skilled in ion channel recording may determine specific methods that may be used for specific ion channels. In the following, we describe several whole-cell recording approaches. In one example, the whole-cell recording is performed on the cell after the membrane patch that has been pulled into the hole on the chip is ruptured. There may be various methods for rupturing such membrane patches and the electronic sealing between the cell membrane and the holes is maintained during the rupturing process.

As an example, one method for rupturing such membrane patches may be the application of an electrical voltage pulse applied to the electrodes that are in contact with the solutions on the top surface of the chip and the electrodes that are in contact with the solutions on the bottom surface of the chip. Appropriate voltage-pulse amplitudes and durations are required for making such membrane ruptures. Such a rupturing method is similar to the electrical voltage pulse method for rupturing membrane patch in a glass capillary that is used to manually operated patch clamp methods. Those who are skilled in ion channel recording may determine the electronic pulse conditions in terms of the pulse amplitude and pulse duration.

As another example, a method may be the application of a negative pressure pulse applied from the bottom surface of the chip so that the pulse of pulling force is applied to the membrane patch inside the hole. Appropriate negative pressure-pulse amplitudes and durations are required for making such membrane ruptures. Such a rupturing method is similar to the negative pressure pulse method for rupturing membrane patch in a glass capillary that is used to manually operated patch clamp methods.

In another ion channel whole-cell recording method, the membrane is actually not ruptured. However, perforation agents such as nystatin or amphotericin B may be used to form pores or perforations on the membrane patch. These perforation agents may be introduced into the hole from the bottom surface side of the chip. The use of these perforation agents for making pores on the membrane patch in the hole of the chip is similar to the use of such agents for making pores on the membrane patch inside the glass capillary. Those who are skilled in ion channel recording may readily choose the concentrations of such agents for making perforations in the cell membranes.

In another ion channel whole-cell recording method, the membrane is actually not ruptured, nor perforated. In this case, the membrane patch remains intact. This technique is referred as the "attached membrane patch" recording.

Actual electronic recording of ion channel responses may depend on specific measurement protocols used. In one example, the resting membrane potential may be measured. In another example, a series of electronic voltage pulses may be applied to the membrane, and the current going through the ion channels located on the cell membranes is determined. This method is particularly useful for analyzing the electrophysiology properties of voltage-gated ion channels. In another example, the current going through the ion channels on the membranes is measured as a function of the concentrations of the specific chemical ligands or chemical molecules in the solution. The specific chemical ligands or molecules are in the solutions above the chip. Such a method is particularly useful for ion-channels that are extra-cellular ligand-gated ion channels. The specific chemical ligands or molecules are in the solutions below the chip and are in contact with intracellular space through the holes on the chip. Such a method is particularly useful for ion-channels that are intracellular ligand-gated ion channels. The above-mentioned methods can also be utilized for measuring the current or other electrical parameters for the ion transporters. It is important to know that if the ion transporter involves the use of energy sources such as ATP, then the ATP molecules should be added into the solutions. For non-energy associated ion transporters, appropriate solutions should also be utilized.

For other specific types of ion channels such as stretch-gated ion channels, appropriate mechanical stresses should be applied to the cell that has been patch clamped.

The electronic current or other electronic parameters may be measured as a function of the mechanical stresses that are applied or as a function of whether the stretch force is applied to the ion channels.

Electroosmosis Structures

Electroosmosis refers to the fluid motion induced by the application of a DC electric field, typically a uniform DC field. The electroosmosis can be exploited for moving, transporting and manipulating and positioning particles. Electroosmosis structures refer to the structures that can generate electroosmosis effects. For example, when the ion transport measuring means comprises a hole through the chip and comprises electrodes or microelectrodes that are on both side of the chip and are in contact with the solutions at the two sides of the chip, the electroosmosis can be generated in the hole and the electroosmosis structure comprises the hole and the electrodes.

In one example, electroosmosis structure can be used for enhancing the sealing between the particle surface and the ion transport measuring means. For simplicity, we discuss an example in which the particles that are being analyzed are mammalian cells. The ion transport measuring means in this example is a hole that is etched through the chip substrate, as exemplified in FIG. 1 and FIG. 2. An individual cell in the solution placed in chamber comprising the chip is positioned above the hole with various positioning means. For example, quadropole electrodes may be used to push the cell into the region between the four electrodes within the quadropole electrode structure.

After the cell positioning means moves the cell onto the hole, a DC electric field is produced in the hole so that an electroosmosis effects may be generated in the hole. The fluidic flow is along the direction from the top to the bottom. Such a flow in the hole would result in a net pulling force on the cell so that the cell is pulled into the hole. During this process, a gradual sealing between the cell membrane and the hole on the chip occurs. Such a sealing will be monitored through the measurement of the total impedance between the solution over the chip and the solution below the chip. Depending on the specific electrophysiology measurement approach, certain impedance values may be required for achieving electronic sealing tight enough so that small electronic noises are produced. This process is similar to the electronic sealing procedure of the cell membrane onto a glass pipette tip that is widely used in electrophysiological ion channel recording.

After the appropriate electronic sealing is achieved, various measurement methods can be implemented to recording the ion channel responses. All the methods described in the context of "DC electric field induced fluid motion structures" can be utilized.

Electrophoretic Structures

Electrophoresis refers to the motion of the charged particles (such as cells or cell fragments) under the application of a DC electric field, typically a uniform DC field. The electrophoresis can be exploited for moving, transporting and manipulating and positioning particles. Electrophoresis structures refer to the structures that can generate electrophoresis effects on charged particles. For example, when the ion transport measuring means comprises a hole through the chip and comprises electrodes or microelectrodes that are on both side of the chip and are in contact with the solutions at the two sides of the chip, the electrophoresis forces can be exerted on the charged particles near the hole or positioned over the hole and the electrophoresis structure comprises the hole and the electrodes.

In one example, electrophoresis structure can be used for positioning the particles and for enhancing the sealing between the particle surface and the ion transport measuring means. For simplicity, we discuss an example in which the particles that are being analyzed are mammalian cells. The ion transport measuring means in this example is a hole that is etched through the chip substrate, as exemplified in FIG. 1 and FIG. 2. An individual cell in the solution placed in chamber comprising the chip is positioned above the hole with various positioning means. For example, quadropole electrodes may be used to push the cell into the region between the four electrodes within the quadropole electrode structure.

After the cell positioning means moves the cell onto the hole, a DC electric voltage is applied between the electrodes that are located on the top surface and the bottom surface of the chip. A DC field is produced in the regions near the hole. Such DC field may exert the electrophoresis forces on the particles, driving the cells towards the hole. Furthermore, the electrophoretic forces on the cell would result in a net pulling force on the cell so that the cell is pulled into the hole. During this process, a gradual sealing between the cell membrane and the hole on the chip occurs. Such a sealing will be monitored through the measurement of the total impedance between the solution over the chip and the solution below the chip. Depending on the specific electrophysiology measurement approach, certain impedance values may be required for achieving electronic sealing tight enough so that small electronic noises are produced. This process is similar to the electronic sealing procedure of the cell membrane onto a glass pipette tip that is widely used in electrophysiological ion channel recording.

After the appropriate electronic sealing is achieved, various measurement methods can be implemented to recording the ion channel responses. Specific measurement methods utilized will depend on the type of ion channels and depend on whether single- channel or whole-cell recording is used, and depend on what functions or properties the measurements are targeted for. Those who are skilled in ion channel recording may determine specific methods that may be used for specific ion channels. In the following, we describe several whole-cell recording approaches. In one example, the whole-cell recording is performed on the cell after the membrane patch that has been pulled into the hole on the chip is ruptured. There may be various methods for rupturing such membrane patches and the electronic sealing between the cell membrane and the holes is maintained during the rupturing process.

As an example, one method for rupturing such membrane patches may be the application of an electrical voltage pulse applied to the electrodes that are in contact with the solutions on the top surface of the chip and the electrodes that are in contact with the solutions on the bottom surface of the chip. Appropriate voltage-pulse amplitudes and durations are required for making such membrane ruptures. Such a rupturing method is similar to the electrical voltage pulse method for rupturing membrane patch in a glass capillary that is used to manually operated patch clamp methods. Those who are skilled in ion channel recording may determine the electronic pulse conditions in terms of the pulse amplitude and pulse duration.

As another example, a method may be the application of a negative pressure pulse applied from the bottom surface of the chip so that the pulse of pulling force is applied to the membrane patch inside the hole. Appropriate negative pressure-pulse amplitudes and durations are required for making such membrane ruptures. Such a rupturing method is similar to the negative pressure pulse method for rupturing membrane patch in a glass capillary that is used to manually operated patch clamp methods.

In another ion channel whole-cell recording method, the membrane is actually not ruptured. However, perforation agents such as nystatin or amphotericin B may be used to form pores or perforations on the membrane patch. These perforation agents may be introduced into the hole from the bottom surface side of the chip. The use of these perforation agents for making pores on the membrane patch in the hole of the chip is similar to the use of such agents for making pores on the membrane patch inside the glass capillary. Those who are skilled in ion channel recording may readily choose the concentrations of such agents for making perforations in the cell membranes.

In another ion channel whole-cell recording method, the membrane is actually not ruptured, nor perforated. In this case, the membrane patch remains intact. This technique is referred as the "attached membrane patch" recording.

Actual electronic recording of ion channel responses may depend on specific measurement protocols used. In one example, the resting membrane potential may be measured. In another example, a series of electronic voltage pulses may be applied to the membrane, and the current going through the ion channels located on the cell membranes is determined. This method is particularly useful for analyzing the electrophysiology properties of voltage-gated ion channels. In another example, the current going through the ion channels on the membranes is measured as a function of the concentrations of the specific chemical ligands or chemical molecules in the solution. The specific chemical ligands or molecules are in the solutions above the chip. Such a method is particularly useful for ion-channels that are extra-cellular ligand-gated ion channels. The specific chemical ligands or molecules are in the solutions below the chip and are in contact with intracellular space through the holes on the chip. Such a method is particularly useful for ion-channels that are intracellular ligand-gated ion channels. The above-mentioned methods can also be utilized for measuring the current or other electrical parameters for the ion transporters. It is important to know that if the ion transporter involves the use of energy sources such as ATP, then the ATP molecules should be added into the solutions. For non-energy associated ion transporters, appropriate solutions should also be utilized.

For other specific types of ion channels such as stretch-gated ion channels, appropriate mechanical stresses should be applied to the cell that has been patch clamped. The electronic current or other electronic parameters may be measured as a function of the mechanical stresses that are applied or as a function of whether the stretch force is applied to the ion channels.

Acoustic Structures

Acoustic structures refer to the structures that can generate acoustic field and thus exert acoustic forces on the particles. For example, a biochip could be made from a piezoelectric material and when electrical field is applied across the biochip, the mechanical vibrations can be generated on a biochip and an acoustic field can be generated in the solutions that are in contact with such a biochip. In this case, the piezoelectric structures include the biochip with its piezoelectric material and the electrodes on the chip.

Figure 2:
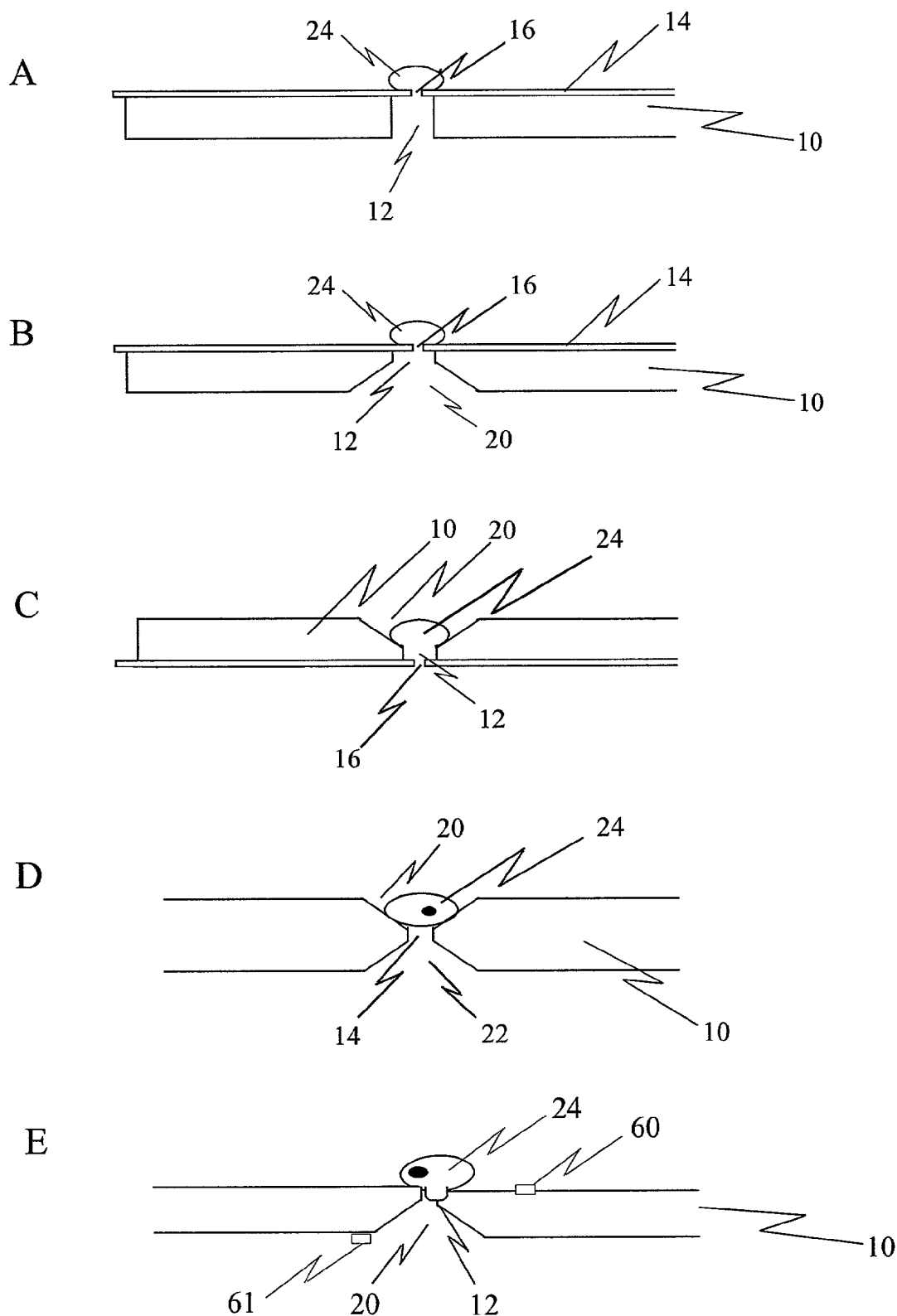
FIG. 2 depicts different configurations of substrates (10) and coatings (14) to form holes in the substrate (12) and holes in the coating (16).
Figure 3A:
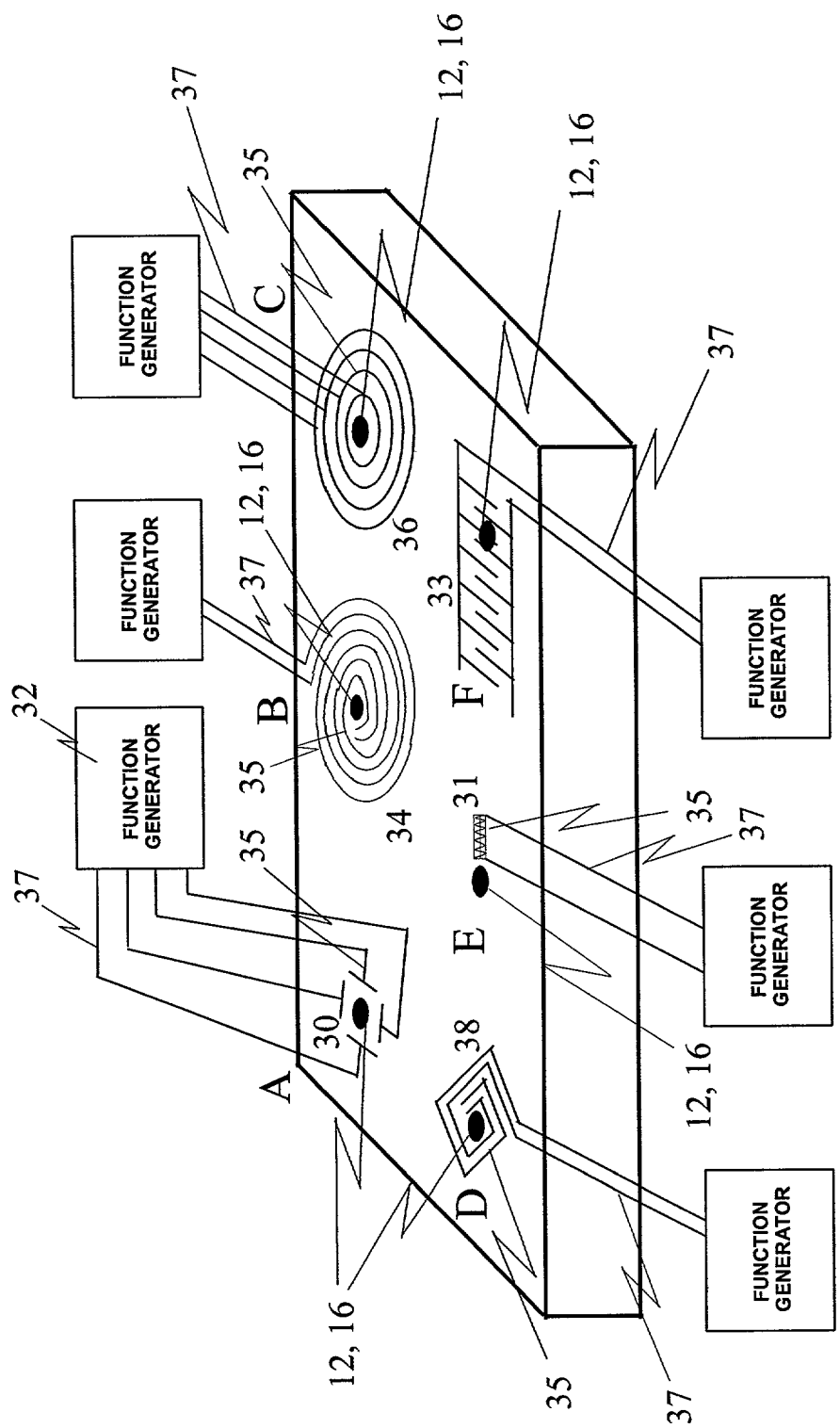
FIG. 3A depicts a quadrople electrode structure or electrorotation structure (30) useful for positioning particles (35) at or near a hole (12, 16) wherein the electrical connection leads (37) thereto are operably connected with an electrical signal source (32), such as a sine wave generator (which can also provide signals other than sine waves), to allow modulation of current at the electrode structures to allow positioning of particles (35).
Figure 3G:
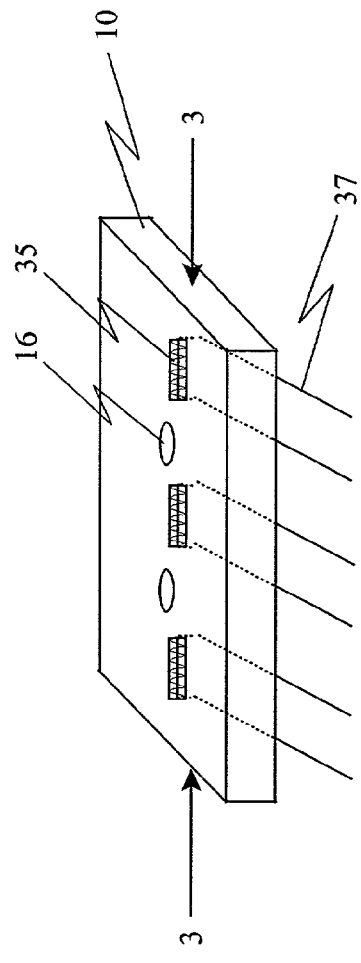
FIG. 3G depicts a biochip wherein electromagnetic structures (35) are provided on or within a biochip. Preferably, the electromagnetic structures are within the biochip.
Figure 3H:
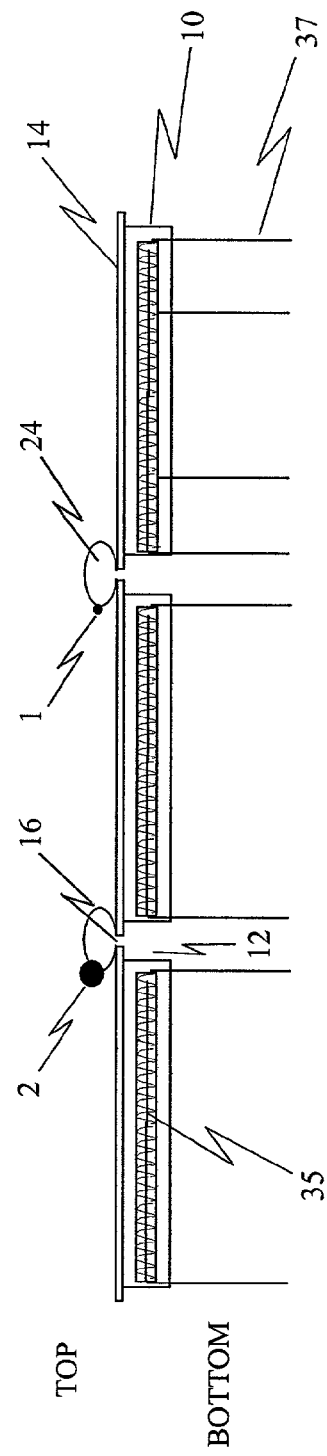
FIG. 3H is a cross section of the biochip of FIG. 3G along 3-3. Also shown are particles such as cells (24) engaged with the holes (16) that can be coupled or linked to a magnetic particle (1, 2) of small (1) or large (2) size.
Figure 4:
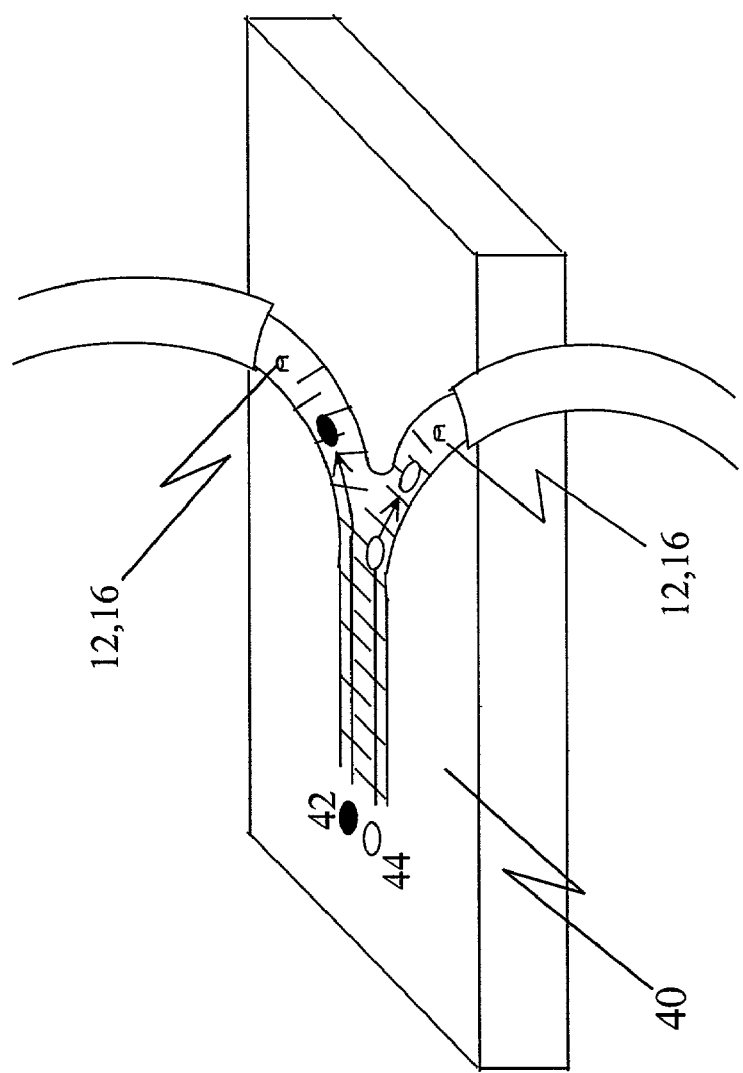
FIG. 4 depicts a particle switch (40) that can modulate the direction of travel of particles of different dielectric properties (42, 44) along a path and through a particle switch. The particle switch can include holes (12, 16) for use at least in part as ion transport measuring means. A sample can include a mixture of target particles and non-target particles. Target particles are preferably separated from or enriched from the non-target particles prior to measurements.

In one example, acoustic structure can be used for positioning the particles and for enhancing the sealing between the particle surface and the ion transport measuring means. For simplicity, we discuss an example in which the particles that are being analyzed are mammalian cells. The acoustic structure is a piezoelectric substrate with electrodes on both major surfaces and is located as the top plate of a chamber. The chamber bottom plate is a chip substrate for the ion transport measuring means, as illustrated in FIG. 1 and FIG. 2. In this example the ion transport measuring means is a hole that is etched through the chip substrate. An individual cell in the solution placed in chamber comprising the chip is positioned above the hole with various positioning means. For example, quadropole electrodes may be used to push the cell into the region between the four electrodes within the quadropole electrode structure.

After the cell positioning means moves the cell onto the hole, electric signals are applied between the electrodes that are located on the top surface and the bottom surface of the chip. Acoustic field is produced in the chamber. Standing wave acoustic fields or traveling wave acoustic fields could be produced. These acoustic fields may exert an acoustic force on the cell, driving it towards the hole. Furthermore, the acoustic force on the cell would result in a net pushing force on the cell so that the cell is pushed into the hole. During this process, a gradual sealing between the cell membrane and the hole on the chip occurs. Such a sealing will be monitored through the measurement of the total impedance between the solution over the chip and the solution below the chip. Depending on the specific electrophysiology measurement approach, certain impedance values may be required for achieving electronic sealing tight enough so that small electronic noises are produced. This gradual sealing is similar to the electronic sealing of the cell membrane onto a glass pipette tip that is widely used in electrophysiological ion channel recording.

The acoustic structure could also be attached onto the bottom plate of the chamber. The acoustic waves from such structures can be coupled through the chamber plate and into the solutions above the chamber plate. The acoustic wave or acoustic field in the solution could also be exploited for moving the particles and enhancing electronic sealing between the particle surface and the chip surfaces.

After the appropriate electronic sealing is achieved, various measurement methods can be implemented to recording the ion channel responses. Specific measurement methods utilized will depend on the type of ion channels and depend on whether single- channel or whole-cell recording is used, and depend on what functions or properties the measurements are targeted for. Those who are skilled in ion channel recording may determine specific methods that may be used for specific ion channels. In the following, we describe several whole-cell recording approaches. In one example, the whole-cell recording is performed on the cell after the membrane patch that has been pulled into the hole on the chip is ruptured. There may be various methods for rupturing such membrane patches and the electronic sealing between the cell membrane and the holes is maintained during the rupturing process.

As an example, one method for rupturing such membrane patches may be the application of an electrical voltage pulse applied to the electrodes that are in contact with the solutions on the top surface of the chip and the electrodes that are in contact with the solutions on the bottom surface of the chip. Appropriate voltage-pulse amplitudes and durations are required for making such membrane ruptures. Such a rupturing method is similar to the electrical voltage pulse method for rupturing membrane patch in a glass capillary that is used to manually operated patch clamp methods. Those who are skilled in ion channel recording may determine the electronic pulse conditions in terms of the pulse amplitude and pulse duration.

As another example, a method may be the application of a negative pressure pulse applied from the bottom surface of the chip so that the pulse of pulling force is applied to the membrane patch inside the hole. Appropriate negative pressure-pulse amplitudes and durations are required for making such membrane ruptures. Such a rupturing method is similar to the negative pressure pulse method for rupturing membrane patch in a glass capillary that is used to manually operated patch clamp methods.

In another ion channel whole-cell recording method, the membrane is actually not ruptured. However, perforation agents such as nystatin or amphotericin B may be used to form pores or perforations on the membrane patch. These perforation agents may be introduced into the hole from the bottom surface side of the chip. The use of these perforation agents for making pores on the membrane patch in the hole of the chip is similar to the use of such agents for making pores on the membrane patch inside the glass capillary. Those who are skilled in ion channel recording may readily choose the concentrations of such agents for making perforations in the cell membranes.

In another ion channel whole-cell recording method, the membrane is actually not ruptured, nor perforated. In this case, the membrane patch remains intact. This technique is referred as the "attached membrane patch" recording. Actual electronic recording of ion channel responses may depend on specific measurement protocols used. In one example, the resting membrane potential may be measured.

In another example, a series of electronic voltage pulses may be applied to the membrane, and the current going through the ion channels located on the cell membranes is determined. This method is particularly useful for analyzing the electrophysiology properties of voltage-gated ion channels. In another example, the current going through the ion channels on the membranes is measured as a function of the concentrations of the specific chemical ligands or chemical molecules in the solution. The specific chemical ligands or molecules are in the solutions above the chip. Such a method is particularly useful for ion-channels that are extra-cellular ligand-gated ion channels. The specific chemical ligands or molecules are in the solutions below the chip and are in contact with intracellular space through the holes on the chip. Such a method is particularly useful for ion-channels that are intracellular ligand-gated ion channels. The above-mentioned methods can also be utilized for measuring the current or other electrical parameters for the ion transporters. It is important to know that if the ion transporter involves the use of energy sources such as ATP, then the ATP molecules should be added into the solutions. For non-energy associated ion transporters, appropriate solutions should also be utilized. For other specific types of ion channels such as stretch-gated ion channels, appropriate mechanical stresses should be applied to the cell that has been patch clamped. The electronic current or other electronic parameters may be measured as a function of the mechanical stresses that are applied or as a function of whether the stretch force is applied to the ion channels.

Negative Pressure Structures

Negative pressure structures refer to the structures that can generate negative pressures onto the cells or other particles and thus exert pressure forces on the particles. For example, fluidic pumps can be used for generating such negative pressures on the cells that are over a hole etched through a chip.

In one example, negative pressure structures can be used for positioning the particles and for enhancing the sealing between the particle surface and the ion transport measuring means. For simplicity, we discuss an example in which the particles that are being analyzed are mammalian cells. The negative pressure structure is a fluidic pump that is connected to the fluid in a chamber for ion channel measurement. The chamber bottom plate is a chip substrate for the ion transport measuring means, as illustrated in FIG. 1 and FIG. 2. In this example the ion transport measuring means is a hole that is etched through the chip substrate. An individual cell in the solution placed in chamber comprising the chip is positioned above the hole with various positioning means. For example, quadropole electrodes may be used to push the cell into the region between the four electrodes within the quadropole electrode structure. The fluidic pump is connected to the fluid below the ion channel measurement chip in a sealed fluidic circuit.

After the cell positioning means moves the cell onto the hole, fluidic pumps is set to certain flow rate to pull the fluid from the chamber to the pump for certain length time for achieving an electronic seal between the cell membrane and the surface of the hole. Such a fluidic withdrawal from the chamber may result in a pulling force on the cell (for example a negative pressure on the cell), driving the cell into the hole. During this process, a gradual sealing between the cell membrane and the hole on the chip occurs. Such a sealing will be monitored through the measurement of the total impedance between the solution over the chip and the solution below the chip. Depending on the specific electrophysiology measurement approach, certain impedance values may be required for achieving electronic sealing tight enough so that small electronic noises are produced. This gradual sealing is similar to the electronic sealing of the cell membrane onto a glass pipette tip that is widely used in electrophysiological ion channel recording.

After the appropriate electronic sealing is achieved, various measurement methods can be implemented to recording the ion channel responses. Specific measurement methods utilized will depend on the type of ion channels and depend on whether single- channel or whole-cell recording is used, and depend on what functions or properties the measurements are targeted for. Those who are skilled in ion channel recording may determine specific methods that may be used for specific ion channels. In the following, we describe several whole-cell recording approaches. In one example, the whole-cell recording is performed on the cell after the membrane patch that has been pulled into the hole on the chip is ruptured. There may be various methods for rupturing such membrane patches and the electronic sealing between the cell membrane and the holes is maintained during the rupturing process.

As an example, one method for rupturing such membrane patches may be the application of an electrical voltage pulse applied to the electrodes that are in contact with the solutions on the top surface of the chip and the electrodes that are in contact with the solutions on the bottom surface of the chip. Appropriate voltage-pulse amplitudes and durations are required for making such membrane ruptures. Such a rupturing method is similar to the electrical voltage pulse method for rupturing membrane patch in a glass capillary that is used to manually operated patch clamp methods. Those who are skilled in ion channel recording may determine the electronic pulse conditions in terms of the pulse amplitude and pulse duration.

As another example, a method may be the application of a negative pressure pulse applied from the bottom surface of the chip so that the pulse of pulling force is applied to the membrane patch inside the hole. Appropriate negative pressure-pulse amplitudes and durations are required for making such membrane ruptures. Such a rupturing method is similar to the negative pressure pulse method for rupturing membrane patch in a glass capillary that is used to manually operated patch clamp methods.

In another ion channel whole-cell recording method, the membrane is actually not ruptured. However, perforation agents such as nystatin or amphotericin B may be used to form pores or perforations on the membrane patch. These perforation agents may be introduced into the hole from the bottom surface side of the chip. The use of these perforation agents for making pores on the membrane patch in the hole of the chip is similar to the use of such agents for making pores on the membrane patch inside the glass capillary. Those who are skilled in ion channel recording may readily choose the concentrations of such agents for making perforations in the cell membranes.

In another ion channel whole-cell recording method, the membrane is actually not ruptured, nor perforated. In this case, the membrane patch remains intact and is sealed against the ion transport detection structures. If the ion transportation detection structure is a hole on an ion-channel chip, the membrane patch is made in contact with the surfaces of the hole having a very large sealing resistance (e.g., Giga-Ohm) between the solutions at the two ends of the hole. In this way, the whole cell remains relatively intact. This technique is referred as the "attached membrane patch" whole-cell recording. Thus, the electrical voltages applied between the electrodes that are in contact with the solutions at the two ends of the hole are applied to the membrane patch in the hole and to the large-area membrane surface, which are the areas other than the membrane patch. Recording data needs to be carefully analyzed to take into account such recording mode.

In another ion channel recording method, we would be recording the ion channel activities for the ion channels that are located in the membrane patch. In this case, the membrane is actually not ruptured, nor perforated. Indeed, the membrane patch remains intact while other parts of the cells are ruptured or removed from the attached membrane patch. In this way, the "inner surface" of the attached membrane patch that is in contact with the cytoplasm before the removal of other parts of the cells is now made in contact with external cell bathing medium. Again, the membrane patch needs to have a very high resistance sealing (e.g. giga ohm sealing) against the measurement structures. Thus, the measured current response from the membrane patch corresponds to the ion channel activities from single or multiple ion- channels or ion transporters that are located in the membrane patch. This is a "single-channel recording" technique.

Actual electronic recording of ion channel responses may depend on specific measurement protocols used. In one example, the resting membrane potential may be measured. In another example, a series of commanding electronic voltage pulses may be applied to the membrane, and the current going through the ion channels located on the cell membranes is determined. This method is particularly useful for analyzing the electrophysiology properties of voltage-gated ion channels. In another example, the current going through the ion channels on the membranes is measured as a function of the concentrations of the specific chemical ligands or chemical molecules in the solution. The specific chemical ligands or molecules are in the solutions above the chip. Such a method is particularly useful for ion-channels that are extra-cellular ligand-gated ion channels. The specific chemical ligands or molecules are in the solutions below the chip and are in contact with intracellular space through the holes on the chip. Such a method is particularly useful for ion-channels that are intracellular ligand-gated ion channels. The above-mentioned methods can also be utilized for measuring the current or other electrical parameters for the ion transporters. It is important to know that if the ion transporter involves the use of energy sources such as ATP, then the ATP molecules should be added into the solutions. For non-energy associated ion transporters, appropriate solutions should also be utilized.

For other specific types of ion channels such as stretch-gated ion channels, appropriate mechanical stresses should be applied to the cell that has been patch clamped. The electronic current or other electronic parameters may be measured as a function of the mechanical stresses that are applied or as a function of whether the stretch force is applied to the ion channels.

Horizontal Positioning Means and Vertical Positioning Means

The particle positioning means can be horizontal positioning means or vertical positioning means. Horizontal positioning means allow a particle to be moved over the surface of a chip, such as at least in the X-Y axis where gravity is in the Z-axis. Horizontal positioning means are exemplified but not limited to traveling wave dielectrophoresis structures, dielectric focusing structures, spiral electrodes, concentric electrodes and particle switch structures that can guide the path of a particle to an ion transport measuring means. Vertical positioning means allow a particle to be drawn towards a ion transport measuring means, such as a hole, such as at least in the Z-axis where gravity is also in the Z-axis. Vertical positioning means are exemplified but not limited to acoustic structures, electroosmotic structures, electrophoretic structures and negative pressure structures.

In general, a chip can have a major surface, onto which a sample that can include particles such as cells is introduced. The chip preferably has one or more particle positioning means provided integral to the chip. The forces acting on the particles in any direction within a plane parallel to the major surface are horizontal forces whereas the forces acting on cells in a direction approximately normal to the major surface are vertical forces.

The particles such as cells to be analyzed may initially be randomly distributed above the surface of a chip, such as in a fluidic chamber above the chip. Thus, it can be desirable if forces generating means could produce forces in the horizontal plan, the vertical plane or both. In this way, these forces can be used for rapid, efficient and effective positioning of the particles. In one preferred aspect of the present invention, both horizontal positioning means and vertical positioning means are included in whole or in part within or on a chip or can be provided in whole or in art on or within ancillary structures, such as a fluidic chamber or housing.

These force-generating means can be integral, such as a single type of structure element can be used for generating both a horizontal force and a vertical force, but that need not be the case and separate structures can be used. For example, the force generating means can be separate, for example, one structure can be used for producing one or more vertical forces and the other type for producing one or more horizontal forces. The force generating means can include two or more structures, each of the structures optionally capable of producing both horizontal and vertical forces on the particles to be positioned. In the alternative, at least one of the structures is capable of producing at least one horizontal force and at least one vertical force. Such structures can be used in combination with other structures.

In general, certain forces generated by force generating means can have both horizontal and vertical force components. The forces with both vertical and horizontal components can be generated by a single type of force generating structure or by multiple structures. Such force generating structures can have a single or multiple types of signal application modes. In one aspect of the present invention, the horizontal force is generated, preferably primarily generated, by one structural element and the vertical force is generated, preferably primarily generated, by a second type of structural element, but that need not be the case. In one aspect of the present invention, the horizontal and vertical forces can be generated by two or more force generating structures, each of which is capable of generating the forces in both horizontal and vertical directions. In the alternative, a combination of force generating structures can be used to produce forces in both the horizontal and vertical directions.

Ion Transport Measuring Means

Ion transport measuring means can be a structure that can be used to detect or measure ion transport function or property. Preferred ion transport measuring means include patch clamp detection structures. Such patch clamp detection structures preferably include a hole or capillary that can contact a particle such as a cell or a portion thereof such as to form a seal between the membrane of the cell or portion thereof and the detection structure. This hole or capillary is preferably part of a patch clamp detection structure. Preferably a tight seal between the particle and the hole is obtained, preferably with mega ohm characteristics and more preferably with giga ohm characteristics. At least one electrode such as a recording electrode is also preferred, as is a detection device, such as device that can detect, monitor and preferably record a variety of electric parameters, such as electric current, voltage, resistance and capacitance of the membrane being patched, including cellular membrane, artificial membrane and the like. In one aspect of the present invention, the ion transport measuring means includes a wire that can be used in the ion transport detection methods. The ion transport detection means can detect ion transport function or property in whole cells or in portions thereof, such as in vesicles, blebs or patches of membranes.

As shown in FIG. 1, the ion transport detection means preferably includes holes that are provided in a substrate and optionally with a coating to provide well-defined holes. The holes can be provided in any appropriate configuration, but are preferably provided as an array. The holes can be of any shape, but are preferably generally circular when viewed from the top or bottom. The holes can be of any shape when viewed from the side, but are preferably generally cylindrical or generally funnel shaped when viewed from that angle. The funnel shape can be preferred because this type of shape can be the result of etching procedures, particularly Deep Reactive Ion Etching (DRIE) of silicon.

The holes in the substrate can be of any appropriate size, but the opening that is to directly or indirectly contact the particle are generally between about 0.1 micrometers and about 100 micrometers in diameter and more preferably between about 0.5 micrometers and about 10 micrometers in diameter. In the aspect of the invention where funnel shaped holes are used, the widest diameter is preferably between about 0.2 micrometers and about 200 micrometers in diameter and more preferably between about 0.5 micrometer and about 20 micrometers in diameter.

Holes in the coating can generally be made more accurately and precisely due to the characteristics of the material and the thickness of the coating. These holes can be of any shape, but are preferably generally circular when viewed from the top or bottom. These holes are generally between about 0.1 micrometer and about 100 micrometers in diameter and more preferably between about 0.5 micrometers and about 10 micrometers in diameter.

The holes in the substrate or coating can be made using any appropriate method for the material that makes up the substrate. Micromachining, laser ablation, molding, dry or wet etching or masking are methods that are preferable. In one aspect of the present invention, the holes in the substrate are made by first etching the substrate using chemicals, such as acid etching of glass or DRIE of silicon materials. Such etching can form the funnel structures (20, 22) as generally set forth in FIG. 2B, FIG. 2C and FIG. 2D.

Figure 5:
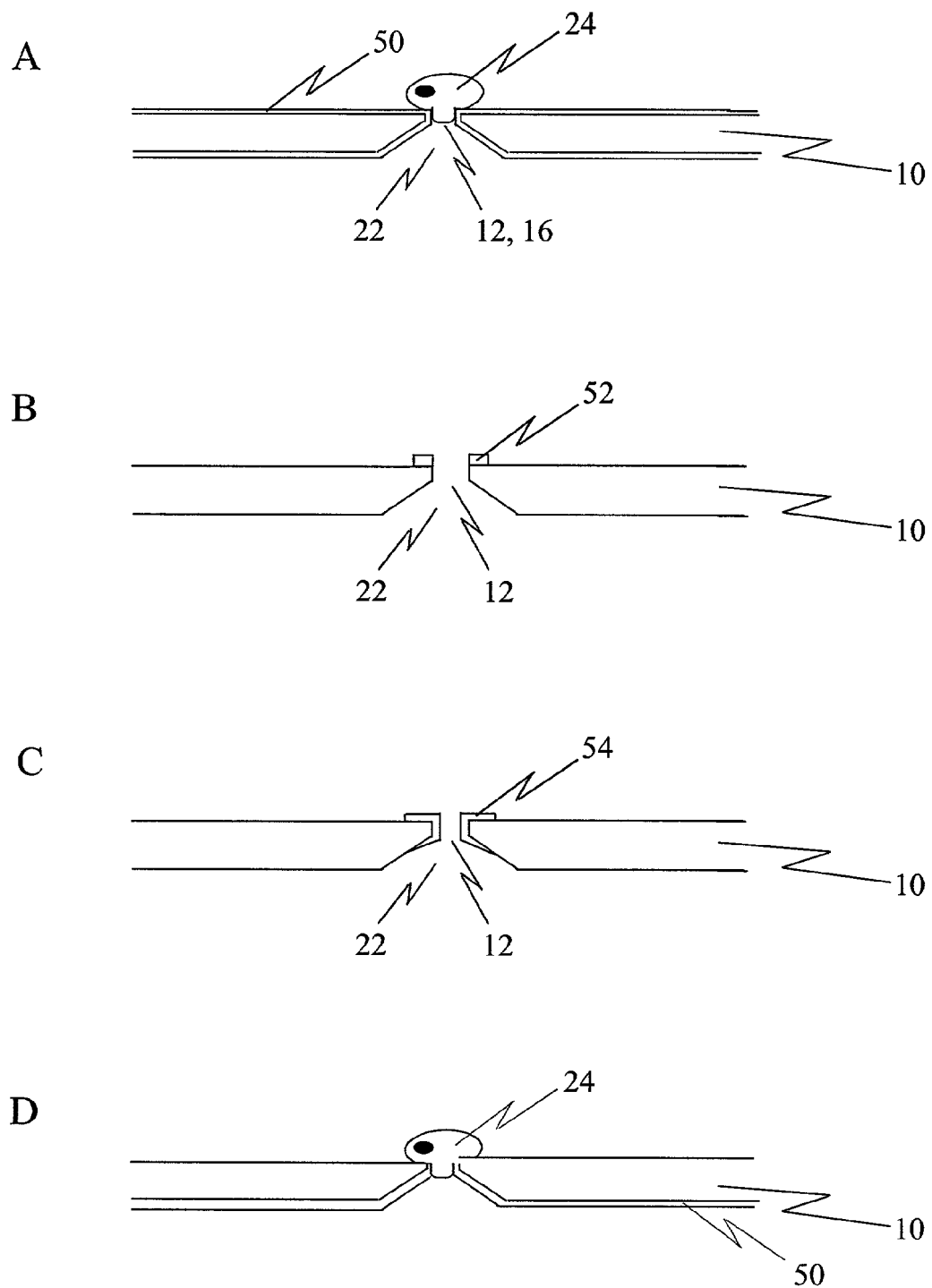
FIG. 5 depicts a structure such as depicted in FIG. 2B including a substrate (10) that defines a hole (12) with a funnel structure (22).

As shown in FIG. 5, the holes can include additional coatings, such as particularly set forth in FIG. 5A, FIG. 5B and FIG. 5C. The depicted coatings can be made of a variety of materials and are intended to increase the "strength" or "tightness" of the seal between the particle and the hole. In one aspect of the present invention, the coating (50, 52, 54) can be made of a polymer that expands or contracts as temperature changes, such as expanding when temperature increases. In that way, a particle can be contacted with a hole at a low temperature the temperature changed so that the coating expands, and the seal between the cell and the hole becomes "tighter." For patch clamp methods, the seal should have characteristics in the mega ohm range, and more preferably in the giga ohm range. Coating can be applied using methods known in the art, such as spraying, thermal oxidation, sputtering or spin casting. Preferred coating materials include plastics, polymers, molecular layers or metal oxides. In one alternative, hypertonic conditions can be used when a particle such as a cell is engaging a structure such as a hole, which causes the particle to shrink or crenate. A tight seal can be made by returning to normal osmolarity or by making the environment hypotonic, causing the particles to expand. Preferred coatings include polyimide, polyethyleneimine, PDMS, paralyne, PMMA SU8 and the like. Some of these polymers can be elastic after being incorporated onto or within a chip. In this instance, when particles such as cells are being driven or aligned into or onto the aperture, the elastic property of the polymers can help forming a tight electric sealing between the particle and the polymer coating. These polymer coatings can help to reduce the noise coupling from the solution to the measurement electrodes and from the electrode to the air. The polymer coating or other coating can also reduce the electronic capacitance coupling between the solution baths on the top and bottom of the aperture or in certain instances sideways perfusion chambers to the measurement electrodes.

Alternatively, the coating can include specific binding members, such as ligands, receptors, antibodies or active fragments thereof. This is particularly true for the configurations set forth in FIG. 5B and FIG. 5C. The specific binding members can be specific or non-specific for a particle, such as a cell. For example, the specific binding members can be antibodies that recognize cell surface antigens or receptor for a population of cells. In the alternative, the specific binding member can be specific for an antigen that is engineered into the cell such that the cell would not normally express the antigen, preferably a cell surface antigen. In this way, particles, particularly cells or fragments thereof, would be localized at or near a hole based on the binding of particles to specific binding members that have been localized on the biochip. In the alternative, specific binding members that bind with non-specific cell surface antigens such as, for example, cell adhesion molecules including basement membrane proteins, fibronectin, integrins or RGD-containing peptides or proteins or active fragments or portions thereof, can also be used. Furthermore, the specific binding members localized at or near the edges of the hole would tend to increase the "tightness" of the seal between the cell and the hole to form a tight patch clamp.

Figure 6:
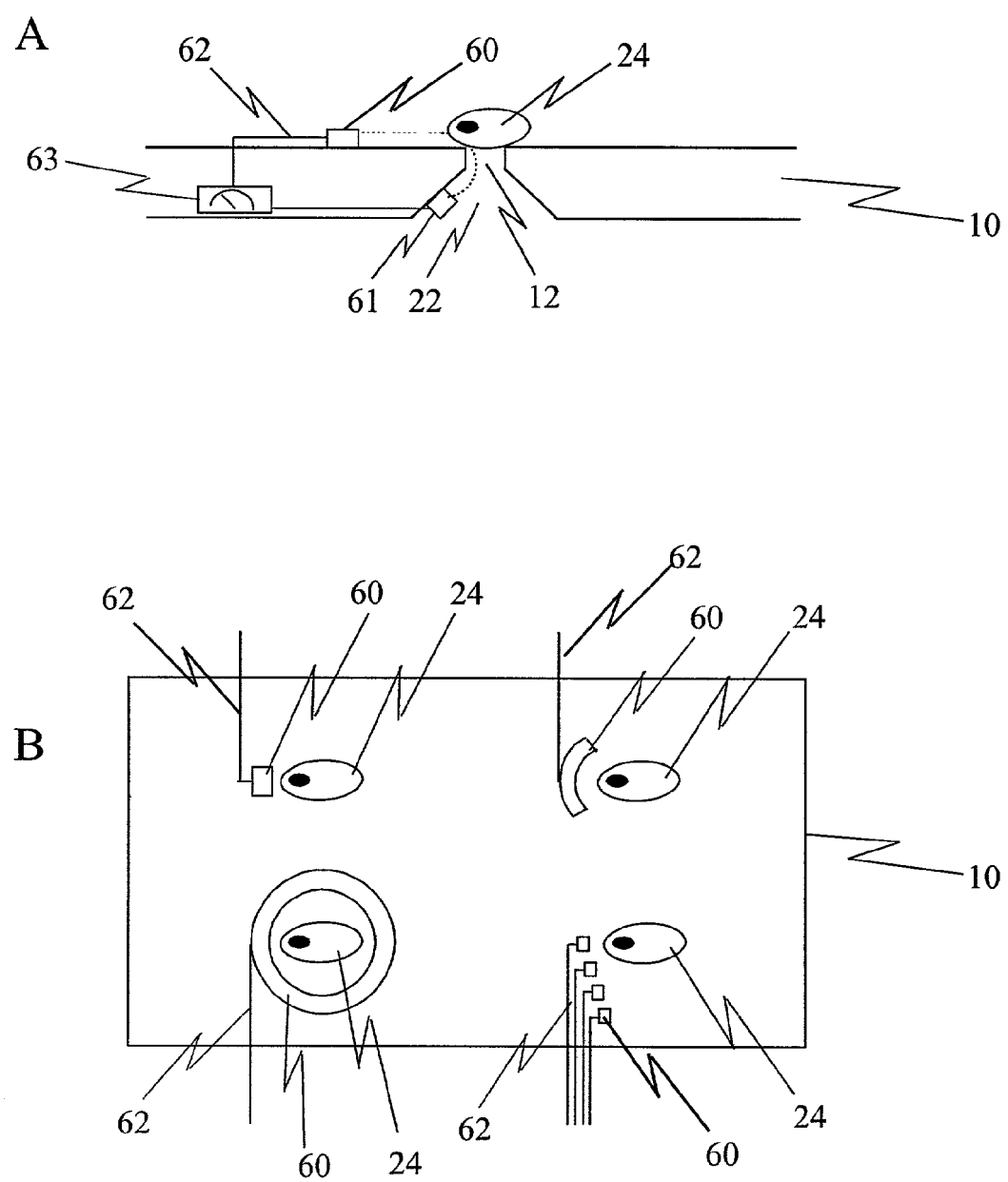
FIG. 6A depicts electrode structures (60, 61) present on either side of a hole (12, 16) defined by a substrate (12) and depicted as including a funnel structure (24). The electrodes are positioned as to be on either side of particle, such as a cell (24). Electrical connection leads (62) connect the electrodes (60, 61) to a measuring device (63) that can measure and optionally record the electrical properties of the particle depicted by the dashed line, such as, for examples, electric current through the ion transports in the particle membrane under applied voltage conditions or the cell membrane potential under fixed current flow through the ion transports in the membrane. Measuring device (63) can be conventional electrophysiology measurement apparatus, such as described by Axon Corporation.
FIG. 6B depicts a variety of electrode structures as viewed from the top of FIG. 6A. In one aspect of the present invention, the electrode (60) can have any appropriate shape, such as square, circular or semi-circular. The electrode is preferably operably linked to at least one electrical connection lead (62). In one aspect of the present invention, there can be several electrodes, preferably independently attached to separate electrical connection leads so as to be independently addressable, that have different distances from a hole (12, 16). Depending on the conditions of a particular method or the electrical parameter being measured, such as voltage or current, electrodes of different shapes, sizes or geometries can be utilized. Although

The ion transport measuring means can also include an electrode. As depicted in FIG. 6, for example, electrode structures can be provided on either side of a particle such as a cell when engaged with a hole. The electrode structures are preferably made using conductive material such as metal, such as gold, and can be of any shape or size appropriate for the configuration of an ion transport measuring means, such as a patch clamp structure. The electrodes can be made using appropriate methods, such as masking, sputtering and the like. The proximity of the electrodes to each other and to the particle when engaged, preferably between about 10 micrometers and about 100,000 micrometers and can be optimized using routine experimentation. This range is not a limiting factor of the present invention and the range can be smaller or larger. The electrodes are preferably connected with electrical connection leads, which are preferably made of conductive materials and fabricated upon or within the biochip. Such fabrications are known in the art, such as in the fabrication of electronic chips. The electrical connection leads preferably directly or indirectly connect to a measuring device that can measure and optionally record a variety of electric measurements, such as current, voltage, resistance or capacitance.

In one aspect of the present invention, a chip can include application specific integrated circuits (ASIC). Typically, a patch clamp recorded ionic current is of a mall magnitude, such as in the pico Amp, nano Amp or micro Amp range. For accurate and precise measurement and recording of currents in these ranges, it is preferred to have the ASIC located within the closest distance from the particles such as cells that are being measured. This, it is preferred to have ASICs that can be incorporated at least in part onto or within a chip of the present invention. The ASIC can optionally include the same functions as a head-stage that is commonly used in traditional patch clamp recording systems, as they are known in the art.

ASIC can have one or more features, such as high input impedance and relatively small output impedance. In one aspect of the present invention, an ASIC can convert the electronic current to electronic voltage. There are certain advantages of having an ASIC integral at least in part to a chip or provided in the vicinity of a chip. One advantage is that the small distance from the source of the ionic current to the measurement circuit can reduce electronic noise which results in reduced signal loss. Another advantage is the reduction of stray capacitance effect, which is related to potentially long signal connection wires can be minimized. Also, the weak current signal can be converted to a voltage signal that can be connected to an appropriate signal amplifier.

In one embodiment of the present invention, an ASIC can convert an electronic current to an electronic voltage. In general, operational amplifiers are used for achieving such purposes. As known in the art of microelectronics, operational amplifiers typically have high input impedance; very large open-loop gains and can drive different kinds of impedance loads. Two modes of operational amplifiers can be designed to achieve conversion of electronic current to voltage, for example, resistive feedback and capacitive feedback. In the resistive feedback mode, the current is passed through "feedback resistor" and generates a voltage across the feedback resistor. This voltage can be monitored and recorded. In the capacitive feedback mode, the current is passed through the "feedback capacitor" to charge up the capacitor. Thus the voltage across the feedback capacitor will ramp up with time as a result of the current charging up the capacitor. Capacitive feedback mode has advantages including low electronic-noise but has disadvantages that the voltage across the capacitor cannot ramp forever in one direction so that a reset of this charging-voltage is needed once a while. Resistive feedback mode has the advantage that it does not require reset but it can have a relative large thermal noise component.

Those who are skilled in the art of microelectronics can readily design circuits for achieving the operational amplifiers with either resistive or capacitive feedback configurations or both, and can then realize and implement these circuit designs into Integrated Circuits.

A number of functions or features can be included into the ASIC. These may include:

(1) Potential-offset. In some applications, the electrolyte solution that is for bathing cells may be different from the electrolyte that is connected with the intracellular compartments. In one exemplary configuration, the ion-channel measuring means comprises an aperture etched through the chips. The cells are positioned over the aperture before seals are formed and the measurements are conducted for determining the voltage-current relationships between the electrodes located on the two sides of on the chips when a cell is positioned on the aperture with or without membrane patch being ruptured. In such a case, the electrolyte solutions on the topside of the chip may be different from those on the bottom side of the chip, thus producing an electrical-potential difference between the top-solutions and the bottom solutions. The potential-offset circuits will be able to offset this potential difference account the voltage or current clamp mode. Because different application setting may use different electrolyte solutions and may result in un-identical "potential-difference", the potential-offset circuit should be able to compensate these different values. The exact potential-offset values may be controlled externally or by applying external signals to the potential-offset circuits. Those who are skilled in the art of microelectronics and understanding the patch-clamp processes can readily design the circuitry for such potential-offset.

(2) Series resistance compensation. The solution resistances for the solution suspending and for the solution in the recording-aperture (again, we use the chips with apertures as examples only) present themselves as series resistors to the ion-channels that are being recorded for their activities. In order to have a fast amplifier response to achieve better temporal resolutions, these serial resistors should be compensated by certain ASIC. The ASIC may have separate circuits for compensating not only the bulk solution resistances but also the resistances in the aperture. In addition, the compensation values may be adjusted in both large-magnitude and small magnitude variations. Those who are skilled in the art of microelectronics and understanding the patch-clamp processes can readily design the circuitry for such series-resistor compensation.

(3) Membrane patch ZAP control. In one of the whole cell recording modes, the membrane patch within the recording-aperture (again, we are using the chips with apertures as an example only) is ruptured. One way to make this rupture is to apply a brief high voltage pulse in the range between 100 mV to 10,000 volts to the membrane via the recording electrodes. The ASIC may comprise a separate circuit that can deliver variable magnitude and variable duration of electric-potential pulses. The magnitude and temporal duration of the pulses can be changed by external means or by applying certain control signals externally. Those who are skilled in the art of microelectronics and understanding the patch-clamp processes can readily design the circuitry for such membrane-patch ZAP control circuits.

(4) Whole cell capacitance neutralization. The whole cell capacitance is acting in parallel to the ion-channels that are being measured. Such capacitances should be neutralized or compensated to achieve better temporal control and accurate measurement of the ionic current. The exact values of the neutralized capacitances may be different for different experiments. Thus, the ASIC may incorporate specific circuits for neutralizing or compensating such whole cell capacitance. The magnitude of the compensation capacitances can be changed by external means or by applying certain control signals externally. Those who are skilled in the art of microelectronics and understanding the patch-clamp processes can readily design the circuitry for such whole cell capacitance neutralization. In designing such circuits, the neutralization should be able to "be turned off" when the experiments were for evaluating or measuring the whole cell capacitances.

(5) The chip-capacitance compensation. The chip-capacitance is acting in parallel to the ion-channels that are being measured. (again, we use the chip with recording apertures as examples). Such capacitances should be compensated to achieve better temporal resolution to observe fast kinetic responses of the ion channels. The exact values of the compensated capacitances may be different from different experiments. Thus, the ASIC may incorporate specific circuits for compensating such chip-capacitances. The magnitude of the compensation capacitances can be changed by external means or by applying certain control signals externally. Those who are skilled in the art of microelectronics and understanding the patch-clamp processes can readily design the circuitry for such chip-capacitance compensation.

(6) High-quality low-pass filters. The recorded electrical signals tend to be noisy. Thus, appropriate electronic filters may be applied to filter out the high-frequency noises to obtain cleaner signals. For example, multiple-pole (e.g. 4-pole) Bessel filter may be used. The ASIC may comprise specific filter circuits. Those who are skilled in the art of microelectronics and understanding the patch-clamp processes can readily design such filters to remove/filter out the noises.

(7) Seal-Test. The patch-clamping recording requires high-resistance sealing between the cell membrane and the apertures in the chips (again, we are using the chips with apertures structures as examples only). It is desirable to have a specific circuit that can be operated to test whether a high resistance seal is formed. In the voltage-clamp mode, a small voltage (<10 mV, or ~10 mV) may be applied and then current responses are monitored. Before sealing, there may be relatively large current responses during to the current leaking through the hole. Yet after a high-resistance seal is achieved, the current will be quite small. The magnitude of the current is inversely proportional to the seal resistance. A current-pulse may also be applied in the current-clamp mode. In such a case, the voltage responses should be monitored. The ASIC may comprise specific circuits for such Seal-Test. Those who are skilled in the art of microelectronics and understanding the patch-clamp processes can readily design such pulse-generating and voltage/current monitoring circuits.

(8) Independent holding command. In some experiments, it may be desirable to have the ability to independently hold the voltage in the voltage-clamp mode or hold the current in the current-clamp mode. The ASIC may comprise a separate circuit for generating such independently controlled voltages or currents. Those who are skilled in the art of microelectronics and understanding the patch-clamp processes can readily design circuits for generating independently held voltage or current.

(9) Leak-subtraction. Since a perfect sealing between the membrane and the chip-recording apertures (again, we are using the chips with apertures as examples only) is nearly impossible, the leak current exists in many real recording setting. Such leak current is of linear voltage-current response in nature, thus a subtraction of such current may be desirable. The ASIC may comprise a specific circuit that can subtract such linear leak current components. Those who are skilled in the art of microelectronics and understanding the patch-clamp processes can readily design circuits for subtracting the leak currents.

Other Strucutres

The biochip of the present invention can also include additional structures. For example, a biochip can include a chamber that can include ports for the introduction and/or removal of materials. One aspect of such a chamber is provided in FIG. 14. In this figure, the biochip with holes is provided in a chamber such that fluidic space is provided above and below the chip so that fluid communication between the top chamber and bottom chamber when holes are not engaged with particles is possible. Particles such as cells are introduced into the upper chamber using an induction means. Induction means include pumps, microfluidic structures such as piezo dispenser, ink jet dispensers, solenoids and the like and can be the same or different from perfusion means. Induction means are used to introduce a sample to a chip or chamber, whereas perfusion means are used to introduce test chemicals or other moieties to a chip or chamber.

The particles are directed to ion transport measuring means using particle positioning means. The particle, such as a cell is then engaged with the structures of ion transport measuring means, such as a hole, using particle-manipulating means. The particle positioning means can also act to aid in forming a tight seal between the particle and the hole. For example, acoustic means, such as acoustic chips, can provide positive downward pressure on particles. In the alternative, electroosmotic force or electrophoretic force, such as electrodes operably engaged with an electric modulating device such as a reostat can be used to provide negative pressure on the particles. Furthermore, a fluidic means, such as a pump or microfluidics device can be used to provide negative pressure on the particle.

In operation, the particle manipulating means or fluidic means can be used to create a pulse such as an electric pulse or pressure pulse that rupture the membrane of a particle such as a cell to allow whole cell patch clamp recording.

In one aspect of the present invention, the perfusion means can be used to inject a sample into the chamber. The sample preferably includes a test compounds whose ion transport modulating activity is known or unknown. Changes in ion transport function or property measured by ion transport measuring means with engaged particles is indicative of the ability of a test compound to modulate ion transport function or property.

Figure 13:
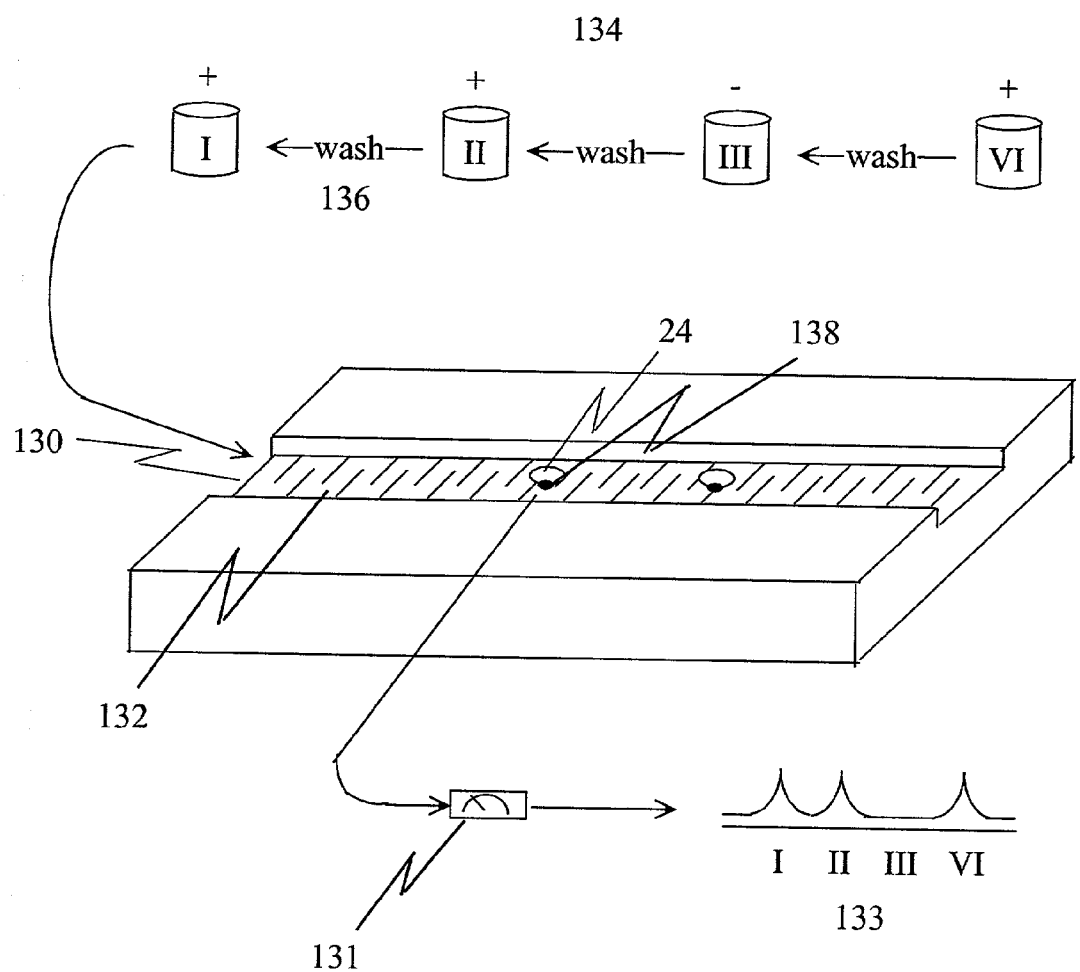
FIG. 13 depicts one preferred aspect of a flow through method for engaging particles such as cells (24) with ion transport measuring means (138). The depicted structure includes a channel (130), but the method depicted in FIG. 13 can be utilized on a biochip that does not include such channels (130). Particles such as cells (24) are positioned at or near ion transport measuring means (138) using particle positioning means (132) depicted here as traveling wave dielectrophoresis structures. The cells (24) engage the ion transport measuring means (138) and allow for detection on ion transport function or property via measuring devices (131) that can provide a readout (133). Samples (134) can be sequentially added to the biochip, such as through the channel (130) with or without dye solutions, reagent solutions including that of substrates, enzymes, or cells and the like, or washing solutions (136) in between the samples. The samples are sequentially contacted with the cells (24). The same cells can be tested with a given set of compounds. The modulation of ion transport function or property in response to these compounds is interrogated using ion transport measuring means (138), and the responses measured (131) and/or reported (133). Here, compounds I, II and IV increased ion transport function or property whereas compound III did not.

In one aspect of the present invention depicted in FIG. 13, a channel is formed that can include particle positioning means and ion transport measuring means. Particles engaged with the ion transport measuring means form patch clamps as discussed above. Test samples can be sequentially added to the channel in a flow-through manner, optionally with wash solutions in between. The responsiveness of the patch clamped particles to the test samples is measured. In this way, the same patch clamps are used to measure a plurality of samples.

Figure 14:
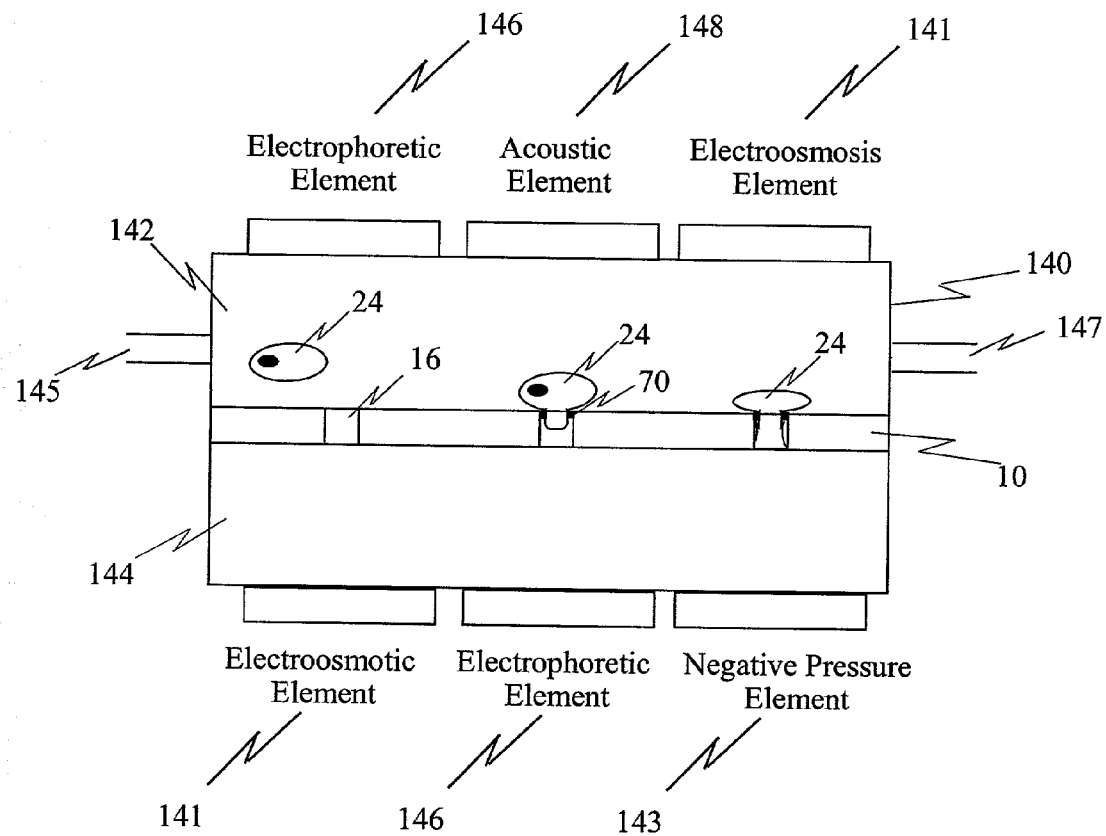
FIG. 14 depicts one aspect of the present invention wherein a substrate (10) with holes (16) is provided in a chamber (140) with an upper compartment (142) and a lower compartment (144) separated by a substrate layer with the holes. The holes (16) can be part of an ion transport detection structure. Capillaries or needles of the present invention can also be present or be substituted for the holes (16). The substrate (10) can include a variety of particle positioning means, particularly horizontal positioning means, such as but not limited to electromagnetic devices and dielectrophoretic devices (not depicted). The chamber (140) can include various particle positioning means, particularly vertical particle positioning structures, such as electrophoretic elements (146), acoustic elements (148), electroosmosis elements (141) and negative pressure elements (143). In operation, a sample that includes a particle such as a cell can be introduced into the chamber (140) by way of a conduit (145). The particle is positioned at or near the hole (16) by way of horizontal positioning structures. The particle is then aligned with the hole (16) using vertical positioning structures. The electric seal (70) between the particle and the hole can be enhanced using coatings, such as coatings including specific binding members or particle adhesion moieties, such a cell surface adhesion proteins, such as integrins or basement membrane proteins such as fibronectin. The particle can then be optionally ruptured, such as by the vertical positioning means such as pressure pulses. Preferably, the negative pressure element (143) performs this function, but that need not be the case. Alternatively ion-conducting holes can be made in the membrane by perforating agents such as but not limited to amphotericin B. At this point in time, ion transport functions or properties of the particle can be determined using methods of the present invention. In one aspect of the present invention, test compounds can be introduced via the inlet port (145) and effluent can be removed via the effluent port (147).

In another aspect of the present invention depicted in FIG. 14, a substrate (10) with holes (16) is provided in a chamber (140) with an upper compartment (142) and a lower compartment (144). The holes (16) can be part of an ion transport detection structure and capillaries or needles of the present invention can also be present or be substituted for the holes. (16) The substrate (10) can include a variety of particle positioning means, particularly horizontal positioning means, such as but not limited to electromagnetic devices and dielectrophoretic devices (not depicted). The chamber (140) can include various particle positioning means, particularly vertical particle positioning structures, such as electrophoretic elements (146), acoustic elements (148), electroosmosis elements (141) and negative pressure elements (143). In operation, a sample that includes a particle such as a cell can be introduced into the chamber (140) by way of a conduit (145). The particle is positioned at or near the hole (16) by way of horizontal positioning structures. The particle is then aligned with the hole (16) using vertical positioning structures. The electric seal (70) between the particle and the hole can be enhanced using coatings, such as coatings including specific binding members or particle adhesion moieties, such a cell surface adhesion proteins, such as integrins or basement membrane proteins such a fibronectin. The particle can then be optionally ruptured, such as by the vertical positioning structures such as by pressure pulses. Preferably, the negative pressure element (143) performs this function, but that need not be the case. At this point in time, ion transport function or properties of the particle can be determined using methods of the present invention. In one aspect of the present invention, test compounds can be introduced via the inlet port (145) and effluent can be removed via the effluent port (147).

In addition to particle positioning means such as those described herein, other particle manipulating means and structures can be incorporated in whole or in part or on a surface or in proximity with a surface of a chip. In one aspect of the present invention, mixtures of particles such as cells can be separated in accordance to certain forces such as those described herein, such as but not limited to pressure, dielectrophoresis or electromagnetic forces. Pressure systems that can be used in the present invention can include gating systems such as they are used in the art of fluorescence activated cell sorting (FACS). The separated particles can then be used for ion channel recording using appropriate structures provided on chips of the present invention. This type of format is particularly useful for handling mixtures of cells, such as cells provided from an organism including mammals and humans, particularly but not limited to primary cells, in which there are multiple cell types can be separated using structures of the present invention at least in part based on the physical properties of such cells. Such separation allows target cells to be separated or enriched prior to being engaged on an ion channel measuring structures such as those of the present invention and being interrogated using appropriate methods, such as those of the present invention. Alternatively, a population of cells can be directed to ion channel measuring structures such as those of the present invention and then engaged and interrogated as appropriate. In one aspect of the present invention, separated or enriched particles can be directed to different loci on a chip of the present invention using the positioning means of the present invention. Different physical properties of particles can be directed to such loci. At such loci, ion channel measuring structures can be present and the particles can be engaged and interrogated as appropriate. Thus, a single chip can be used to investigate members or subsets of a population of particles, such as a population of cells.

Furthermore, additional manipulation means can be incorporated at least in part within a chip, on a chip or in proximity to a chip of the present invention. These structures can be used for high-information content analysis of particles including cells. For example, on-chip, within-chip, partially within chip or off-chip means can be incorporated into a structure of the present invention to measure cellular responses by way of fluorescence or other readouts, particularly optically based readouts. In one aspect of the present invention, either before, during or after patch clamp recording, other cellular events can be monitored, preferably using optical methods such as fluorescence. For example, a variety of intracellular phenomenon are linked to ion channel activity. One such phenomenon is the modulation of calcium ion levels, in particular free calcium ion levels, within the cell. A variety of fluorescent markers are available that have differential fluorescence when bound with calcium. Examples include Fura1 and Fura2. Other ions can be investigated as well. Thus, particles such as cells can be loaded with such fluorescent markers and the particles can be interrogated with electromagnetic radiation, such as light, of appropriate character to allow the fluorescent markers to be activated. Appropriate light detecting means, such as CCDs optionally coupled with wave-guides, can be used to collect the emission of such fluorescent markers to provide readouts of such markers. In that way, multiple phenomena can be measured using methods of the present invention. Such measurements can be simultaneous with the ion channel detection of the present invention or can be separated in space and/or time. Other methods, such as the use of FRET based systems to measure polarization of membranes can also be used (see, for example, U.S. Pat. No. 5,661,035 issued Aug. 26, 1997 to Tsien and Gonzalez and U.S. Pat. No. 6,107,066 issued Aug. 22, 2000 to Tsien and Gonzalez.)

Other cellular events, such as membrane trafficking, protein-protein interactions, protein translocation, diffusion of second messenger molecules inside the particle such as a cell or sub-compartments of the particle such as a cell can be monitored by way of fluorescence based detection technologies such as fluorescent resonance energy transfer (FRET), fluorescence polarization (FP) and fluorescence lifetime methods. Appropriate detection structures can be used to detect, measure and analyze the information generated by such methods.

A number of targets or phenomenon can be analyzed using such fluorescence based screening. These include but are not limited to morphology changes, viability, apoptosis, cellular differentiation, cytoskeletal changes, cell-cell interactions, chemotaxis, spatial distribution changes such as receptor trafficking, receptor internalization or processing, capping or complex formation.

Furthermore, other measurements of particles can be measured using appropriate methods, preferably optical and optionally fluorescence-based methods. For example, the motion or change of morphology of particles such as cells can be measured using appropriate methods. Preferred measurements include but not limited to, cell motility and neurite extension.

In one aspect of the present invention, ion channel recoding of a particle can be coupled with fluorescence imaging, such as high-resolution fluorescence imaging, of a single or multiple targets in the context of particles, particularly intact particles such as intact cells. Such multiple determinations allow for high information content screening of cellular and sub-cellular events as well as high throughput screening. In this aspect of the present invention, increasing the number of assays being performed on a sample, particularly those that are performed substantially in multiple sub-cellular localizations at the same time, generate a wealth of information beyond the traditional single assay used in high throughput screening methods known in the art.

Multiple, functional screenings can be performed simultaneously, near-simultaneously or separated by time and space on the same particles such as cells. In one aspect of the present invention, a system can be used to perform such assays. Such systems would include the appropriate chip, ancillary reagents, fluidic capabilities, readers, data collection structures and data processing structures, such as those including one or more Central Processing Units (CPUs) and appropriate hardware and software. Preferably, the individual cell based, multiplexed optical cellular measurements allow for locating and eliminating fluorescent or optical artifacts and backgrounds, allows for measuring of biological variability of individual cells rather than investigating populations of cells and the isolation and measurement of sub-populations of particles such as populations and sub-populations of cells.

In one aspect of the present invention, particles such as cells that have been interrogated and the results recorded for ion channel currents can be further analyzed by a variety of methods. For example, a single-particle such as single-cell PCR can be used to determine genetic (DNA or RNA) information of the particle, or by a single-particle or single-cell gene expression assay or protein detection assay. These types of analysis and/or gene expression analysis can be performed on the same chip as the ion channel chip or another chip or alternative structure, such as a chip or other structure in communication with the ion channel chip, such as via fluid communication by way of appropriate conduits, such as channels, tubes, troughs or the like can be used. These types of analysis can be performed using methods known in the art or adaptable to the chip environment and structure.

If such analyses are performed on a chip, then appropriate structures and reagents can be utilized. For example, manipulation means such as particle transportation, lyses, molecular extraction, molecular separation can be used. One expel is that after on-chip ion channel recording is performed, an on chip PCR or RT-PCR method can be performed in situ. Preferably, specific genetics information of the particle such as the cell, determined by appropriate methods such as the use of primers to be used in the PCR reactions, is amplified. After this step, the PCR product, such as amplified nucleic acids such as DNA, can be optionally transported to a detection unit and/or optionally analysis unit on the same chip, a different chip or another structure. (FIG. 21) The genetic information provided within the nucleic acid molecule can then be decoded and analyzed using methods known in the art. Transportation of moieties can be accomplished by any appropriate structure and method that can be utilized to transport samples such as fluids. Preferred methods include microfluidics such as the transfer of materials via channels, conduits, troughs, tubing and the like.

Microfluidics can be provided on, within or partially within a chip of the present invention. Such microfluidics can be utilized in order to facilitate the automation and throughput of assays that utilize a chip of the present invention. For effective delivery of sample and reagents, such as a particle sample such as a sample including a cell or cells, perfusion buffer or test compounds, into a chip of the present invention, or a chip-chamber combination, a variety of microfluidic structures can be used. Preferred microfluidic structures are channels, troughs or tubing. Such structures can be made using methods known in the art, such as etching, machining or in one alternative to such methods, by selected polymerization (see, for example, U.S. Provisional Patent Application No. 60/258,281 filed Dec. 26, 2000). As set forth in FIG. 17 and FIG. 18, channels are one preferred microfluidic structure of the present invention, particularly the structural configuration set forth in FIG. 18 where microfluidic channels are incorporated onto or within, at least in part, a chip. These channels can be fabricated onto or at least in part within the substrate of a chip of the present invention. Alternatively, such structures can be added onto the chip of the present invention. The channels can be made of various materials, such as but not limited to plastics, rubbers, PDMS, polyimide, paralyne, SU8, glass, $Al_2O_3$ and the like. The flow of fluid within these channels can be driven by a variety of forces, including capillary flow, positive pressure, negative pressure, electroosmosis, electrophoresis or electrohydrodynamics forces. Appropriate structures can provide the forces, such as pumps, syringes, piezo injectors or dispensers, electric fields, impellers or other structures known in the art, particularly the art of microfluidic circuits.

In one preferred aspect of the present invention, various structural elements useful for microfluidics can be incorporated in whole or in part on or within a chip or provided off-chip. Such elements include but are not limited to pumping mechanisms; electrodes to drive electric-filed induced fluid flow, valves and the like. Such structures can be manufactured using methods known in the art, particularly by MEMS technologies, machining or etching.

Figure 17:
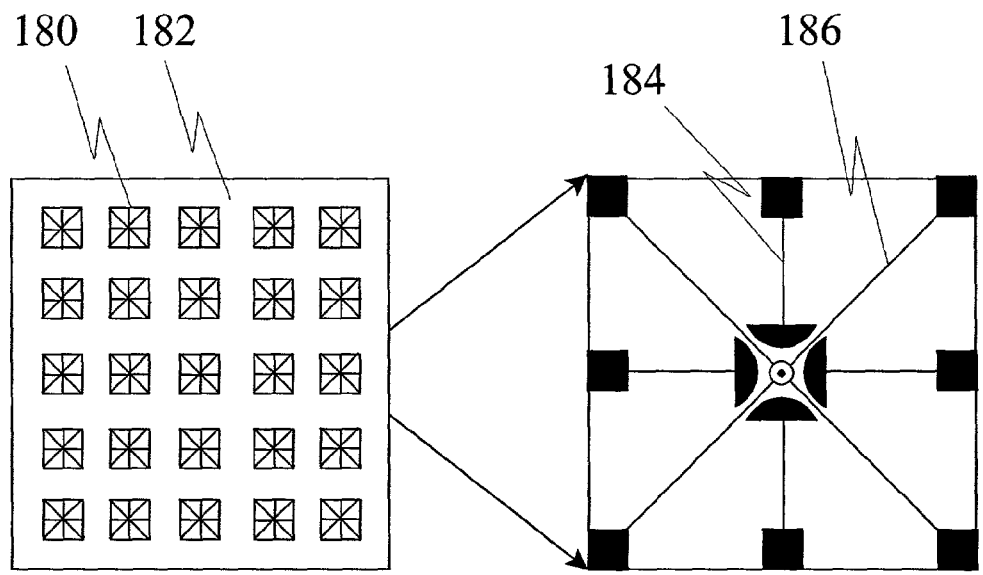
FIG. 17 depicts a chip (180) of the present invention that includes an array (182) of long-range (184) and short-range (186) particle positioning means around a hole on a chip optionally within a chamber (188). Each depicted unit in the array is a measurement unit. Short-range particle positioning means are most effective at a range of less than about 100 micrometers, more typically less than about 40 micrometers. Long-range particle positioning means are most effective at a distance of between greater than about 20 micrometers and less than about 10 centimeters, typically between greater than about 50 micrometers and less than about 1 centimeter or about 5 millimeters. In operation, the long-range (184) particle positioning means are used to localize a particle such that the short-range (186) particle positioning means can localize the particle within a range (181) at the hole (183) such that ion channel determinations can be made. In the instance depicted, the long-range (184) and short-range (186) particle positioning means operate on dielectrophoresis principles. In certain aspects of the present invention, the top chamber can be a single chamber for all of the measurement units, or the top chamber can be multiple discrete units. Such multiple discrete units can engage one or several particles, depending on the number of holes and ion transport detection structures provided. In the aspect where there are individual cells in a measurement unit, then the bottom chamber should be separate and discrete for each measurement unit so that microfluidics using pumps, tubing and the like can be individually monitored and manipulated, and individual recording electrodes and electrical connection leads can be provided. Although the long-range and short-range particle positioning means are depicted as the same configuration in this figure, different configurations can be utilized and can be designed depending on the conditions, target particles and assays to be performed.
Figure 17:
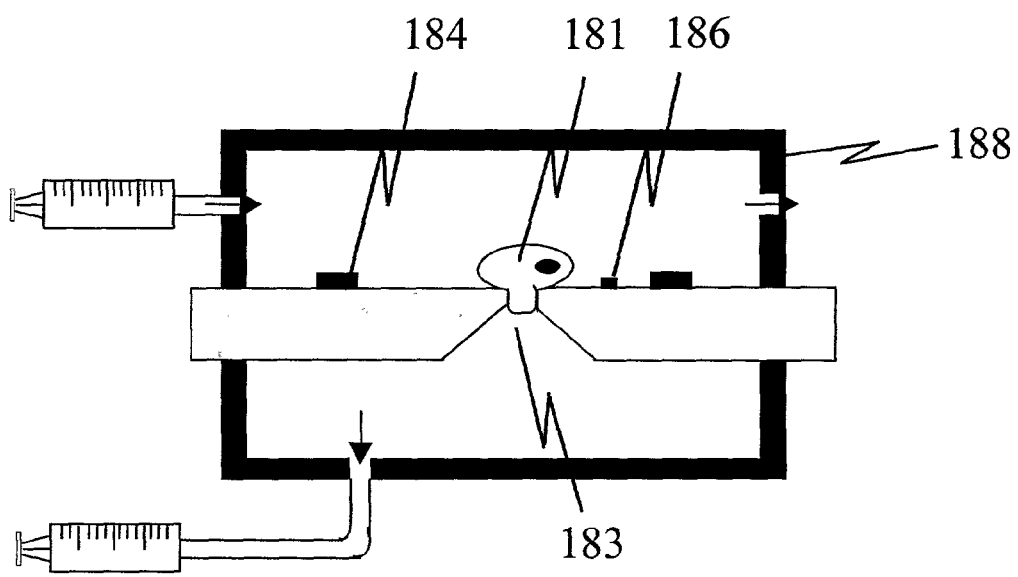

One aspect of the present invention is depicted in FIG. 17. This figure depicts a chip-based cartridge where an individual chip includes multiple, addressable units. Each unit includes a cell positioning structure that can exert physical forces to position particles such as cells into the center or pre-designated location of an individual unit. At the center of the pre-designated location of the unit is located an ion channel measuring structure such as an aperture. The particles that have been positioned onto the aperture are then measured or assayed for their ion channel activities. Each unit preferably has separate fluidic control circuits that are optionally interfaced with the environment outside of the chamber.

Figure 18:
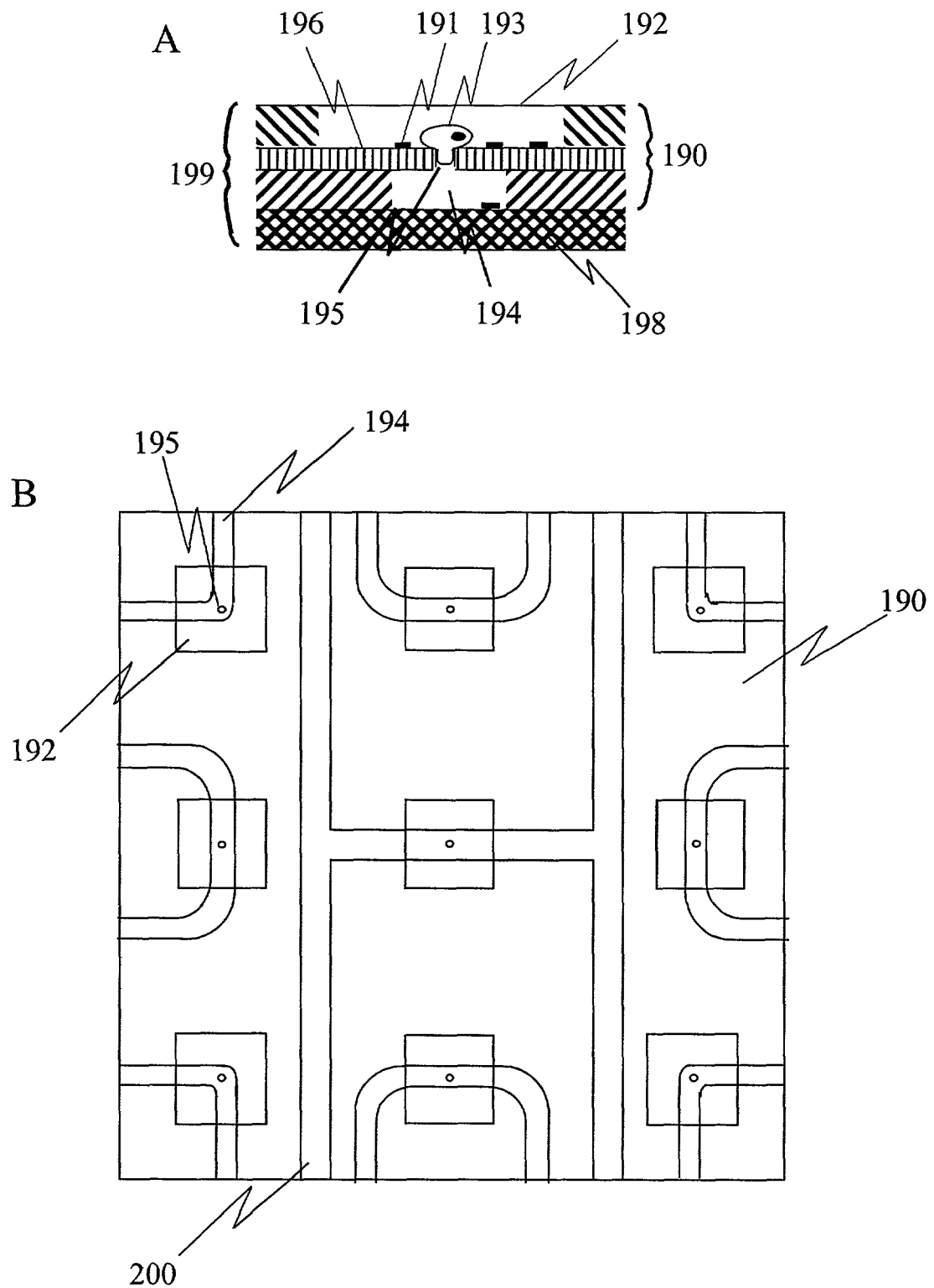
FIG. 18 depicts a modified configuration from that depicted in FIG. 17.

A modification of the chip depicted in FIG. 17 is depicted in FIG. 18. In FIG. 18, duel channels for the chambers. This configuration is more flexible than that depicted in FIG. 17 because a variety of microfluidic circuits can be provided on a chip and channels can optionally link the individual units. FIG. 18 depicts an alternative configuration depicted in FIG. 17. FIG. 18 depicts chambers (190) being formed by a top channel (192) and a bottom channel (194) that can be made using appropriate methods such as etching, machining or polymerization. The channels are preferably closed, but can also be in an open configuration, in particular the top channel (192). The channels are separated by a barrier (196) and are preferably provided on a substrate (198). Particle positioning means (191) can be present to guide a particle, such as a cell (193), to an ion channel detecting structure, such as an aperture (195). A plurality of units (199) can be combined to make an array of units (200) on a chip. Microfluidic connections, such as tubing such as TEFLON™ tubing, can be used to connect the top channel and/or lower channel to the environment external to the chip.

As discussed herein, chip configurations can have an upper chamber and a lower chamber, wherein the chamber can take the form of a channel. The chambers can be open, such as in the form of a trough, or closed such as in the configuration of a tube or pipe. In the alternative, the chambers can form open or closed wells which are larger in size and volume than channels (see, for example, distinction between FIG. 17 and FIG. 18). In one aspect of the present invention, a chip can include a top well that is an open chamber, a bottom chamber that is sealed with a connection such as tubing that connects to a pressure source. Another aspect of the present invention includes a chip, a top sealed chamber that is connected to external fluidic sources by tubing and a bottom sealed chamber that is connected to an external pressure source. Other combinations of open or closed chambers or channels, connection to outside fluidic control devices and fluidic control devices can be used and are apparent to one skilled in the art. Different configurations can be used for different application.

For research instrument and apparatus uses and configurations, a chip that includes an open top chamber, sealed bottom chamber connected to a negative pressure source is preferred. Optionally, other components can be includes, such as a pressure source and electronic apparatus, such as headstage, amplifier and the like.

For safety screening such as cardiac safety screening uses and configurations, a chip with a preferably closed top chamber with tubing inlets, bottom chambers with tubing connected to negative pressure sources and cultured cells as the source for the safety screening test along with a library of the safety testing compounds is preferred. The tubing inlet can be handled to connect to the source of the cultured cells and also to storage structures, such as microplates, microtiter plates or tubes can be directly or directly made. Safety testing refers to the realization that many drugs on the market can unexpectedly modulate ion channel activity non-specifically and can unexpectedly interfere with ion channel activity in non-target tissues such as cardiac tissues. Examples include the popular drugs Seldane™ and cyclosporin that have exhibited unintended modulation of ion channel activity, particularly in cardiac tissues. This phenomenon is of particular concern when the drug does not target ion channel activity as its intended target. Preferred ion channels to investigate for safety screens are HERG and MIRP, which are present in hart and brain tissues and interact together to form active ion channels. Other ion channels include KvLQT and Mink, Kv1.5, Kv2.1 and Kv6.2, and Kv4.3 etc.

For primary screening and secondary screening applications such as for screening for drug candidates, a chip that includes a top chamber, preferably closed but optionally open, can be fitted with a number of inlet tubing. The bottom chambers, preferably closed, can be fitted with multiple tubing connected to pressure sources such as negative pressure sources. The chambers can be connected to cultured cells provided in an appropriate vessel, such as a plate and a library of compounds provided in one or more appropriate containers, such as wells of plates such as microtiter plates or independent tubes. Primary screening refers to the initial testing of a large collection of chemical entities against an ion channel target for desired modulation using a specific assay format. Secondary screening refers to the testing of focused libraries of chemical entities constructed using the knowledge obtained from primary screening to find related compounds that have improved properties.

In one aspect of the present invention, a chip or a chip-chamber combination with or without ancillary structures can be provided in an anti-vibration chamber or structure. Such a chamber can be desirable to minimize shaking of a particle-aperture seal. Motion of a substrate such as a table that is in contact with a chip or ancillary structures can lead to decreased strength of such a seal and lead to increased noise in an ion transport assay. Anti-vibration cambers or structures can include heavy air tables such as those made of stone or metal that resist vibration associated with bumping or movement of buildings. Alternatively, an anti-vibration camber can include a camber filled with a fluid that can act to dampen vibrations, or combinations of such structures and methods.

In addition to particles such as cells or subcellular structures or vesicles, synthetic membranes can also be used in the present invention. For example, synthetic membranes such as lipid bilayers that include ion channels or other ion transporting molecules can be used in the present invention. Such lipid bilayers with and without such molecules can be made using methods known in the art.

In addition, noise reduction in an assay can be accomplished in the present invention based on electrode configuration, structure and materials. For example, ground electrodes in contact with a solution bath are called reference electrodes. In such a case, these types of electrodes are preferably Ag/AgCl or other materials suitable for such reference electrodes. Ag/AgCl can be readily fabricated by way of fabrication methods known in the art. For example, we could use photolithography method to pattern a thin silver film (deposited via various means such as evaporation, or sputtering) to form required electrode geometry. The silver electrode is then processed to become Ag/AgCl by electrochemically reacting the Ag electrodes in an appropriate solution containing chloride ions. Preferred reference electrodes can maintain a constant electrode/solution interface potential difference, or junction potential, relatively independent of the electric current driven through the reference electrodes.

Whereas the reference electrodes are preferably made with suitable materials such as Ag/AgCl for their desired electrochemical properties, the electrodes for injecting current or clamping voltages may also be made of these materials (e.g. Ag/AgCl).

In some embodiments, it is possible that the electrodes for positing the cells or particles via electrical forces (e.g. dielectrophoresis forces, traveling-wave dielectrophoresis forces, electrophoresis forces or electro-osmosis forces) are also used as the electrodes for recording the ion currents for the ion transports. But this does not have to be the case. In other embodiments, the electrodes for positioning of the cells or particles may be different from the electrodes for recording ion currents for the ion transports.

Many of the assays, structures and methods described herein relate to whole cell methods. As described further herein, single-cannel recording or other modes of recording are addressed by the present invention.

In one aspect of the present invention, the members of an array of measuring units can have a common or separate bath cambers and/or microfluidic channels. For example, as depicted in FIG. 17 and FIG. 18, one preferred aspect of the present invention allows units to be addressed by common or separate microfluidic channels by way of microfluidic circuitry.

In another aspect of the present invention, an array of biosensors can be made with synthetic or biological membranes in which ion transports or any ion-conducting pathways reside. Opening, closing or other functions and properties of the ion transports or ion-conducting pathways are linked to the detection of a target molecule, pathogen or other substance. Such detection can be of chemical, physical, biochemical or biophysical or the like in nature, such as the binding of a target molecular to a senor molecular device linked to ion transport detection microdevice described in this invention. Such device allows for highly sensitive single molecule detection of substance in a high throughput low noise manner.

Channel Structures in General

Figure 19:
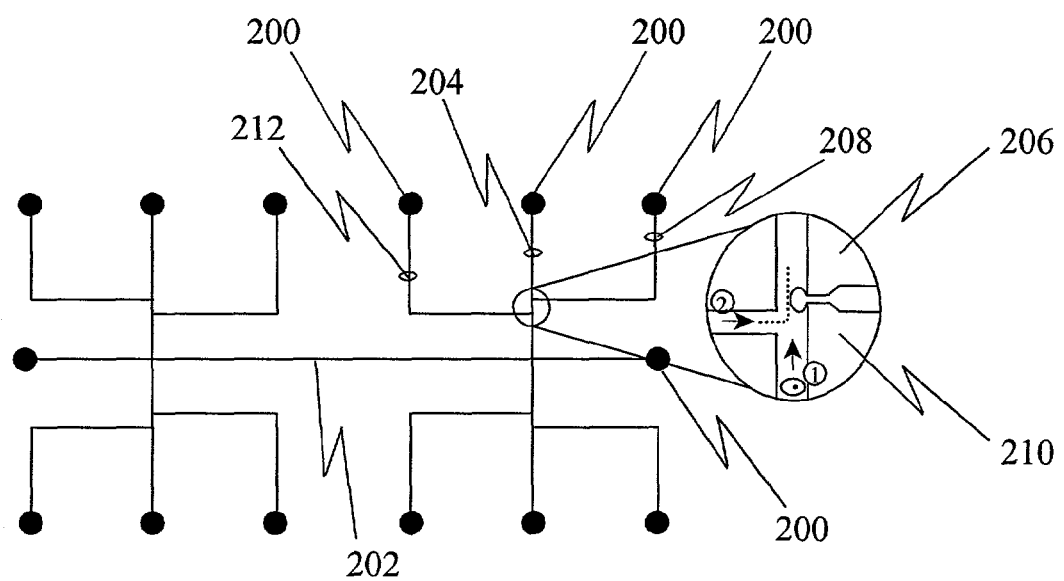
FIG. 19 depicts a top view of a chip of the present invention where the aperture or hole of an ion channel or ion transport detection structure is provided on the side of a channel rather than through the substrate. Additional particle positioning means besides the special confinement by the channels for this type of patch-clamp-in-a-channel technology can be provided near the aperture, but is optional.
Figure 20:
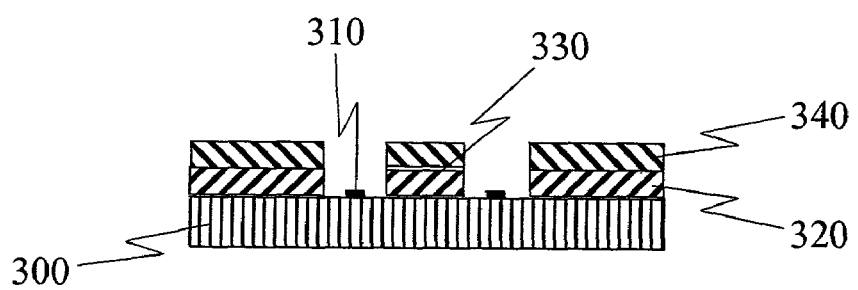
FIG. 20 depicts a cross section of one aspect of an ion transport recording chip depicted in FIG. 19 where the method of manufacture is diagrammatically shown. In one aspect of the present invention, a conduit is made using sacrificial layer methods. One preferred method is wire sacrificial methodologies such as they are known in the art, such as by the use of copper wire.

In one aspect of the present invention, microfluidic channels can be used to form at least one chamber of an ion transport function detection unit of the present invention. In this aspect of the present invention, open or closed channels can be made on chips using methods known in the art, such as machining, molding or polymerization. A closed channel can be made by overcoating a channel or providing a layer of material on top of an open channel, such as a layer of polymer or glass, such as a film of polymer or a thin sheet of glass, such as a coverslip. Subchannels can connect channels to form apertures for use in the methods of the present invention in any orientation, preferably parallel to the surface of the wafer. Alternatively, branch points in a matrix of channels can be used to trap particles such as cells in this type of configuration. FIG. 19 and FIG. 20 depict two configurations for such devices of the present invention.

Generally, particles are transported through main fluidic channels by forces such as positive or negative pressure, or acoustic or dielectrophoretic forces or other appropriate forces are used to draw cells into branch microfluidic channels where one or more recording sites, such as sites including apertures and ion channel detection structures are present. Cells can be stopped by dielectrophoretic, acoustic or other forces close to the recording site, which is preferably a hole in the side of a wall of a microfluidic channel. Pressure such as positive pressure or negative pressure or other appropriate forces can be used to seal the particle such as a cell to a hole or aperture to form Giga Ohm seals. Sealed membranes are then ruptured by electric zap and/or negative or positive pressure or other means such as chemical or enzymatic means to generate whole cell configurations. Patch clamp recording are then performed for each recording unit. Each branch microfluidic channel can have multiple recording sites. One main microfluidic channel can have many branch microfluidic channels. And one chip can have multiple main microfluidic channels.

The structures depicted in FIG. 19 and FIG. 20 can be manufactured using a variety of appropriate methods. For example, a substrate can be provided and prepared for further processing such as sputtering or etching. The electrodes, such as recording electrodes, DEP electrodes, acoustic electrodes or other appropriate electrodes can be fabricated by way of sputtering or other deposition of conductive materials such as metals, preferably gold. The first half of channel layer is fabricated using SU8, polyimide or other polymers or any etchable materials by masking. The sacrificial layer is then fabricated using masking and sputtering of appropriate removable materials. The second half of channel layer is then deposited using the methods used for the first channel layer. The sacrificial layer is then etched away using appropriate methods, such as chemical etching. The resulting structures can be linked by leads within, partially within or on the chip using appropriate connections as described herein or known in the art.

Channel Structures in Duel Vertical Configuration

One aspect of the present invention is a biochip that includes channels or chambers that can be connected in a vertical configuration by way of a hole that can function as an ion transport detection structure. For example, as set forth in FIG. 18A and FIG. 18B, chambers (190) are formed by a top channel (192) and a bottom channel (194). The channels can be made using appropriate methods such as etching, machining, subtractive etching or polymerization. The channels are preferably closed, but can also be in an open configuration, in particular the top channel (192). The channels are separated by a barrier (196) and are preferably provided on a substrate (198). Particle positioning means (191) can be present to guide a particle, such as a cell (193), to an ion channel detecting structure, such as an aperture (195).

Preferably, the structure depicted in FIG. 18A can be made using MEMS technologies in whole or in part. For example, the substrate can be provided and the electrode sputtered using appropriate metals, preferably a metal relatively resistant to sacrificial etching. The bottom channel can be formed by sputtering of subtractive material, such as copper and the lower layer can be provided by methods such as sputtering or masking. The lower layer can be made of any appropriate material, such as polymerized materials or resist. The middle layer is then provided by appropriate methods, such as sputtering, polymerizing or masking. The middle layer is preferably made of material resistant to subtractive etching. The hole is preferably left my masking but can also be made using machining or other appropriate methods. The hole allows etching materials, such as acids, reach into and create the bottom channel by way of subtractive etching. The top channel can be formed by providing an additional layer of material, such as polymerized materials or resist which can be deposited by appropriate methods such as sputtering or masking. The particle positioning means can be made by depositing appropriate materials, such as conductive materials or magnetic or magnetizable materials, using appropriate methods, such as sputtering. The particle positioning means can be coated with another material to prevent direct contact between a sample and these structures. Such material is preferably an insulating material and can be provided using appropriate methods, such as polymerizing, masking or sputtering. Optionally, the top channel can be covered with another structure to form a closed channel. The top channel can be covered with appropriate materials such as thin films of polymers or copolymers, such as cycloolefins or cycloolefin copolymers, or cover slips such as those made of glass or other appropriate materials.

As shown in FIG. 18B, the upper channel can take the configuration of a stand-alone well. In the alternative, the wells can be connected by way of channels that interconnect the wells, preferably through the upper layer of material (such interconnecting channels are not shown). Such interconnections are not necessary but can be desirable. In one aspect of the present invention, the interconnections are not present and the upper channels form wells, much like microtiter wells. These wells can have particle positioning structures such as but not limited to those depicted in FIG. 17. Dispensation methods known in the art, such as pipettes, syringes or other dispensing methods and structures can be used to dispense particles, cells, media, reagents compounds and the like into the well. Alternatively, these wells can be connected to one or more other wells which allows for a flow-through arrangement such that a variety of wells can be provided the same or different materials. In one aspect of the present invention, the wells are not formed and the upper and lower channels spatially intersect without the additional volume of the well structure. Thus, in FIG. 18B, the top channel structure is depicted as a well. Rather than a well, channel structures as depicted for the bottom channels can be provided. This type of configuration would reduce the assay volume of an assay and allow for flexibility in designing and performing assays using these structures.

The lower channels are depicted in configurations that allow for the introduction and removal of materials from the locus of the ion transport detection means. This flow-through allows for the exchange of materials and washing steps during the performance of an assay. The upper channels can be configured in the same or similar way.

Channel Structures in Horizontal Configurations

As depicted in FIG. 19 and FIG. 20, channel-channel intersections can be in a horizontal configuration. FIG. 19 depicts a top view of a chip of the present invention where the aperture or hole of an ion channel or ion transport detection structure is provided on the side of a channel rather than through the substrate. FIG. 20 depicts a cross section of one aspect of a chip depicted in FIG. 19 where the method of manufacture is diagrammatically shown. In one aspect of the present invention, a conduit is made using sacrificial layer methods. One preferred method is wire sacrificial methodologies such as they are known in the art, such as by the use of copper wire.

The structure depicted in FIG. 19 and in cross section in FIG. 20, is one preferred aspect of the present invention wherein the channels are provided side-by-side and are connected by conduits. These smaller channels are used to trap particles such as cells and act as a hole as part of an ion transport detection structure of the present invention. The channels and conduits can be made using any appropriate methods in the art and as discussed herein, preferably MEMS based methods. Preferably, the channels are made using sputtering, polymerizing or other methods. The conduits are preferably made using sacrificial methods, such as sacrificial wire methods.

The tree structure of FIG. 19 allows for a variety of assay formats. The ports (200) allow for materials to be provided to channels and manipulated. For example, reagents can be provided into the channels via ports and the flow of materials in the channels can be regulated by altering the pressure (positive, negative or neutral) applied to the port. Valves can be provided to regulate the flow and pressure at or near such ports (200). The central trunk (202) preferably includes cells that can be transported down the stems (204) to the reaction region (206). The reaction region can include a branch that allows particles to be engaged with a hole. Particles in the reaction region can be engaged with a conduit (210) by having negative pressure applied to the particle positioning channel (208). Reagents such as test compounds can be provided to the reaction region through a reagent channel (212). The channels that modulate the positioning of cells can include particle positioning means and particle separating means. For example, the central trunk (202) can be used to separate cells from a population based on their physical properties, such as dielectrophoretic characteristics. Cells at the branch points can be drawn down the stems (204) to the reaction regions (206) by pressure or other forces, such as electrophoresis. In the alternative, dielectrophoretic structures can guide cells to the reaction region (206). Once in the reaction region, particle positioning forces such as negative pressure by the particle positioning channel (208). One stem may have multiple recording sites each represented by the structure in the blown-up region of FIG. 19.

FIG. 20 is a cross section through FIG. 19 at Z-Z. This cross section is instructive as to methods of making these structures. First, a substrate (300) is provided. On the substrate electrodes for particle positioning means or ion transport detection structures (310) are provided, such as through sputtering. A first layer (320) is provided such as through sputtering, polymerizing, making or other appropriate methods. The sacrificial layer (330) is then provided, such as copper, which can be provided by sputtering or by a wire or similar structure. The second channel layer (340) is then provided, which can be the same or different from the first layer. The sacrificial layer can be digested, such as by acid washing for a sacrificial layer of copper, to form a conduit (210). Rather than being provided at the outset of this procedure, the electrodes (310) can be provided at this point in time, such as through sputtering or other appropriate methods. Optionally, a cover can be provided to make covered channels, but that is not a requirement of the present invention.

Alternatives to the horizontal-horizontal configuration and vertical-vertical configuration discussed above, vertical-horizontal configurations and other three-dimensional configurations can be made.

Channel Structures in Three-Dimensional Configurations

Rather than horizontal-horizontal or vertical-vertical configurations, channels can be made in three-dimensional matrices using appropriate methods. Conduits can be provided between the channels using sacrificial layers as discussed herein. Preferably, a network of channels can be created using sacrificial methods, such as wire subtractive methods. Such sacrificial methods can be combined with other manufacturing methods, such as machining, polymerizing or MEMS technologies. In this aspect of the invention, channels and conduits can be mapped out in three dimensional space using wires or other similar structures that are susceptible to subtractive methods, such as acid degradation. The wires can be imbedded in appropriate material, such as insulating material such as resist or polymerized materials. The imbedding material can be provided in one step, such as in a mold, or in layers. In the latter instance, channels and conduits can be formed using sputtering, masking and other methods.

Channel Structures in High Information Content Screening Configurations

Figure 21:
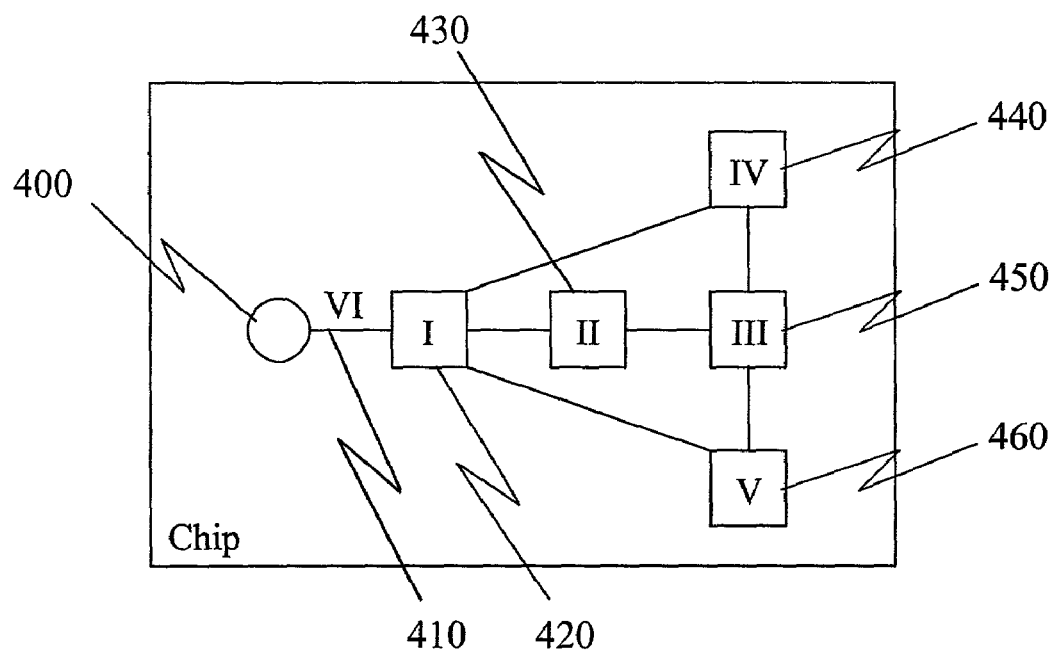
FIG. 21 depicts a multi-functional biochip useful for high information content screening. Samples are provided at port (400). Particles in the same are transported and optionally separated along a channel (410) that can include particle separating structures such as dielectrophoretic structures. Particles can be transferred from the port to the first chamber by particle manipulating means or structures, including pressure or gravity flow of fluids. A first chamber (or well) (420) is provided, which in the depicted configuration is a cell viability test, such as through optical detection methods of dye exclusion. Any appropriate test can take place in the first chamber, but the viability test is depicted for clarity. A second channel can connect the first chamber to other chambers where other tests can be performed. For example, the cells in the first chamber can be transported an ion transport detection unit (430) or other units, such as fluorescent units (450), genomics units (460) or proteomics units (440). The ion transport unit includes ion transport detection structures as described herein, in particular as depicted in FIG. 17, FIG. 18, FIG. 19 or FIG. 20. Optional particle separation units can be provided within, or after each chamber or units that performs detection functions.

FIG. 21 depicts a multi-functional biochip useful for high information content screening. Samples are provided at port (400). Particles in the same are transported and optionally separated along a channel (410) that can include particle separating structures such as dielectrophoretic structures. Particles can be transferred from the port to the first chamber by particle manipulating means or structures, including pressure or gravity flow of fluids. A first chamber (or well) (420) is provided, which in the depicted configuration is a cell viability test, such as through optical detection methods of dye exclusion. Any appropriate test can take place in the first chamber, but the viability test is depicted for clarity. A second channel can connect the first chamber to other chambers where other tests can be performed. For example, the cells in the first chamber can be transported an ion transport detection unit (430) or other units, such as fluorescent units (450), genomics units (460) or proteomics units (440). The ion transport unit includes ion transport detection structures as described herein, in particular as depicted in FIG. 17, FIG. 18, FIG. 19 or FIG. 20. Optional particle separation units can be provided within, or after each chamber or units that performs detection functions.

The different units can be connected to detection devices and structures appropriate for the readout of that unit. For example, for dye exclusion tests for viability, optical methods would be useful to detect the presence and location of dyes such as trypan blue within cells. In some units such as viability units, particles such as cells should remain intact. In other units, such as genomics units or proteomics units, particles such as cells should be lysed.

The fluorescence unit can be used to detect the fluorescence readout of several different tests as described herein, such as protein-protein interactions utilizing FRET applications, membrane potential readouts using FRET applications, ion sensitive fluorescent dyes such as fura2 or fura3, enzyme activity using fluorescent readouts and the like.

The proteomics unit can have a variety of tests, such as affinity reactions such as specific binding reactions, such as receptor ligand or antigen antibody reactions in order to detect the presence and optionally amount of a protein in a sample. Such systems can be based in silico as are known in the art. Particles such as cells can be interrogated as whole cells, or can be lysed to release contents such that the cytoplasmic and internal structures such as nuclei can be interrogated.

The genomics unit can include a variety of structures and methods. Whole particle, such as whole cell, applications include in situ hybridization, such as FISH. Alternative methods include ex vivo hybridization methods that have a particle such as cell being lysed prior to being interrogated. The nucleic acid molecules of a cell, including DNA, RNA and combinations thereof can be interrogated using a variety of methods as they are known in the art. Preferably, in silico methods, such as gene chips known in the art (see, Affimatrix patents and literature) can be used.

Thus, using High information content screening (HCS) of the present invention, a single sample can be provided and interrogated for a variety of particle properties and functions. The information generated by these systems can be collected, compared and utilized in bioinformatic applications, such as drug discovery, pharmacogenomics or pharmacokinetics.

Methods of Use

The present invention also includes a method of detecting ion transport function or property of a particle that includes: contacting a sample comprising at least one particle with the biochip of the present invention and positioning said at least one particle at or near said ion transport measuring means. Ion transport function or property of the sample is then measured using the ion transport measuring means. The sample can be any appropriate sample, but preferably includes a biological sample that includes particles, preferably a cell or population of cells.

A sample solution can optionally be added to a sample before a sample is deposited on a biochip of the present invention or in a chamber that includes a biochip of the present invention. When a sample solution is use, the sample and sample solution can be incubated together for any length of time before adding the sample solution-sample mixture to a chamber for separation, from less than one second to several hours or even days. Sample or sample-sample solution mixing can occur in a conduit that leads to the chamber. Alternatively, a sample can optionally be added to a chamber and a sample solution can be added to the chamber subsequently. It is also possible to add a sample solution to a chamber before adding the sample to a chamber.

A sample, an optional sample solution, and optionally, solutions, buffers, preparations, or reagents, can be added to a chamber by any convenient means, such as transfer with a pipette, injection with a syringe, gravity flow through a conduit, such as tygon, teflon, PEEK tubing, through a microfluidic channel etc. Preferably a sample and other reagents such as solutions, buffers, preparations, or reagents are added to a chamber in a continuous flow mode, in which a continuous stream of fluid is injected or pumped into at least one inlet port, and non-retained sample components and fluids exit the chamber via at least one outlet port.

The particles are directed towards holes on a biochip by particle positioning means. The particles then engage such holes and an electronic seal is formed. The function or property of ion transports are then determined using the structures and methods described herein. Such determinations are preferably made using patch clamp methods or whole cell methods, but other ion transport assay methods can be used.

Generally, the methods of the present invention provide the following characteristics, but not all such characteristics are required such that some characteristics can be removed and others optionally added: 1) the introduction of particles into a chamber that includes a biochip of the present invention, 2) positioning particles at or near an ion transport detection structure, 3) electronic sealing of the particle with the ion transport detection structure and 4) performing ion transport recording.

There a two general purposes for using magnetic particles or dielectric responsive particles in the present invention. The first is bind to a particle for the purposes of separating a particle from other particles, such as in a population of particles in a sample mixture. The second is to position particles in proximity of ion transport detection structures of the present invention. In certain instances, the magnetic particles or dielectric responsive particles can aid in engaging a particle with such an ion transport detection structure. In one aspect of the present invention, particles are selectively attached to magnetic microparticles or dielectric responsive particles, such as through specific binding members, such as antibodies. The particles labeled with magnetic microparticles or dielectric responsive particles are then separated using electromagnetic elements or dielectrophoretic or dielectric elements of the present invention and can be manipulated or positioned at or near an ion transport detection structure. The particle is engaged with such ion transport detection structure and ion transport function or properties can be determined.

In one aspect of the present invention, particles, such as cells, can express an exogenous surface peptide or over-express an endogenous surface protein, such as a cell surface marker not endogenous to the cell. A specific binding member bound to a magnetic particle would specifically bind with that cell and allow for that cell to be separated from a sample including a mixture of cells using magnetic or electromagnetic elements. The magnetic particle bound to a particle would also facilitate manipulation of the particle and positioning at or near an ion transport determination structure such as a hole or capillary. In the alternative, particles having dielectric properties such as latex or polymeric beads can be used instead of magnetic beads and dielectrophoretic or dielectric separating, manipulating and positioning structures can be used in place of the electromagnetic structures. Particles having such cell surface markers can be made by introducing a vector such as a plasmid into a cell. The vector would include a regulatory element such as a promoter operable in the host cell being used operably linked to a nucleic acid molecule encoding the exogenous cell surface protein. Methods of making such constructs, transfection and expression are known in the art.

In another aspect of the present invention, particles such as cells can co-express two proteins, one the exogenous cell surface marker or over-expressed endogenous cell surface marker discussed above and the second an exogenous ion transport protein or over-expressed endogenous ion transport protein. These particles thus have a marker that can be specifically bound with another particle such as a magnetic particle or dielectric responsive particle. These bound particles can be separated, manipulated and positioned with appropriate particle manipulation devices, such as magnetic, electromagnetic and/or dielectrophoretic devices. The particles that are positioned in this way include the ion transport protein which can then be interrogated using structures and methods of the present invention.

A number of patch-clamp recording modes, including whole cell recording, macro-patch recording (including without limitation inside-out, outside-in and cell attached configurations), single channel recording (including without limitation inside-out, outside-in and cell-attached configurations) can be performed on the chips of the present invention. In one preferred aspect of the present invention, the follow order of operations can be used for a whole cell recording using a chip configuration depicted in FIG. 17 or FIG. 18. Fluids are loaded into the bottom chamber such that the aperture or hole is filled. Cells are loaded onto the top chamber and the particles such as cells are positioned to the locations just over the aperture or hole using one or more of horizontal and vertical positioning. Electronic engagement of the particles with the aperture to form Giga Ohm sealing by way of negative pressure driven processes are used to form a tight seal between the particle, such as a cell membrane, and the aperture or hole. The membrane of the particle is ruptured by an electronic zap, a pulse of negative pressure or the addition of appropriate chemicals to digest or break of the membrane within a patch or combinations of such methods. Electronic recording of ion channel activity progresses and the top chamber is optionally perfused. In the cell-attached recording configuration, after the formation of a seal such as a Giga Ohm seal, there is no absolute need for rupturing of the membrane. Electronic recording is made directed on the attached whole cell rather than a patch or portion thereof.

Particularly for high throughput and high informational assays, software systems that can be coupled with a chip of the present invention are desirable. The software can also be coupled to image analysis of cellular phenomenon described herein, particularly optical imaging based on fluorescent based assays. The software is preferably configured to measure electrophysiology and/or patch clamp data information to look for readouts, such as curves, that are out of the ordinary. For example, an active ion channel or ion transport molecule in a membrane provides for a signature profile under a given set of conditions. One example of such a profile for whole-cell or multiple channel assays is a curve that exhibits an activation phase, an inactivation phase, a deactivation phase and optionally a desensitization phase. Parameters for measure include the peak amplitude, duration and time constants. For single channel application, the open duration, open probability, noise analysis, gating current, latency, open time, dwell time, burst length, time interval omission, close time or statistical analysis of distributions of one or more of the above can be measured. When an ion channel or ion transport molecule is contacted with a test chemical or test ligand or other environmental condition, the curves and/or parameters can change. Also, the fluorescent or other optical signal can change as well. The software systems of the present invention are capable of determining and storing reference profiles and compare them to experimental profiles. This comparison can be used to identify, preferably automatically, chemical or ligands or conditions that can alter ion channel or ion transport activity. As the amount of information within the software system grows, preferably in the form of an addressable database, the software system can become more powerful and approach artificial intelligence in power. For example, with a large database of structures and profile, a software system having artificial intelligence capabilities can be used to predict the activity of chemicals or ligands based on their structure based on historical performance of other chemicals or ligands.

Such software systems can also be used to classify channel responses. Different classes of ion channels or ion transport molecules have different signature responses or responses to certain ligands, chemical or environmental conditions. Families of ion channels or ion transport molecules can be categorized based on these profiles. Furthermore, based on historical or taught limits such as gating, hits and misses can be determined by such software systems based on deviation from standard profiles or historical data.

In one aspect of the present invention, chips of the present invention can be used to measure endocytosis, exocytosis, mitosis or blebbing of membranes, particularly using whole particle or whole cell configurations of the present invention. These biological phenomena result in the change of the surface area of a particle or cell. As the surface area of a particle or cell attached to a whole cell patch configuration of the present invention change, the measured capacitance also changes. Because there is no readily available, simple or readily automatable methods for measuring these biological phenomenon, the present invention provides methods for readily measuring these phenomenon that are related to normal cellular functions and tissue specific functions such as neurotransmitter release and uptake. By measuring the change of cellular capacitance using methods such as patch claiming methods of the present invention, a quantitative approach to measuring these biological phenomena are provided. High throughput assay s for endocytosis and exocytosis using the present invention can provide a cost effective and automatable alternative to existing methods. Such capacitance measurement can be performed using structures of the present invention, such as those depicted in FIG. 17 and FIG. 18. With a cell or particle electronically engaged onto the measurement chip, a total cell membrane capacitance can be measured by measuring the impedance between the top chamber and the bottom chamber. The cell or particle can be subjected to certain stimulation, such as regents by a perfusion process or by electronic or other environmental stimulation to result in a chain of cellular biological reaction events. Such a chain of molecular reaction events can lead to endocytosis or exocytosis or, when appropriate, blebbing.

The structures and method of the present invention are well-suited for use in primary or secondary screening in the pharmaceutical or biopharmaceutical industries and are also applicable to safety screening and target identification. The present invention can be adapted for use in primary screening where a compound library is tested against certain in channels or ion transport targets to screen for a hit that has modulatory effects, preferably modulatory effects, on the ion channel or ion transport activities. The present invention can also be used for secondary screening to confirm or otherwise further investigate the primary hits determined using the primary screening methods. Preferably, the chemical structures obtained from the primary hits are further investigated using additional information. For example, the same or different screen can be used to further investigate hits from a primary screen. Repeating a screen adds reliability to the screening procedure whereas the use of multiple screens, such as against different targets or against the same target only under different conditions can provide highly useful information for drug screening purposes. Safety screening, as discussed herein, can be used to identify potential toxic effects or adverse effects of leading drug candidates, drugs in the regulatory approval process or approved drugs.

The structures and methods of the present invention can also be used for performing sequences of nucleic acid molecules such as DNA or RNA or both in single, double or triple stranded configurations or combinations thereof. In such cases, nucleic acid segments can be pulled through an aperture on a chip by a controlled force such as positive or negative pressure, electrophoretic or electroosmotic forces, or the activity of an ion channel or ion transport molecule that accepts a nucleic acid molecule or enzyme such as polymerases, topoisomerases, helicases etc. When different bases or base pairs to through the aperture, the impedance between the top chamber and the bottom chamber would vary according to the type of bases or base pairs, such as A, G, T, C, U and others, going through the aperture. Preferably, the degree and duration of the block of impedance signals is measured to discriminate between different base pairs or bases. In this way, the impedance sequence would be a direct reflection of the nucleic acid sequences being pulled or being pushed through an aperture. Preferably, such nucleic acid molecules are manipulated with physical forces exerting on the segments driving and/or pulling such molecules through the aperture. In one aspect of the present invention, step-wise cleavage of individual bases with a nucleic acid molecule can be utilized. Each cleaved base is driven through an aperture and the impedance readout can be used for sequence nucleic acid segments.

In one aspect of the present invention, membranes such as artificial membranes or other membranes can be used as a biosensor. For example, a membrane with an inserted ion channels or ion transport molecules can be immobilized over an aperture. These ion channels or ion transport molecules may have specific electric-current responses to target analytes to be detected or senses. Thus, when a sample potentially containing a target analyte is flown over the membrane, the target analyte, if present, will alter the ion channel response. In this way, the chips and methods of the present invention can be used as specific detection tools for monitoring target analytes and other molecules. Preferred targets include analytes of interest, including but not limited to biomolecules, pesticides, toxins, poisons, venoms, drugs, drugs of abuse and analogues, precursors or metabolites thereof. These devices and methods may have a very high sensitivity for detecting target analytes and could represent a low cost alternative to other detection methodologies.

One application of such ion channel chips is for agricultural applications. Plant ion channels in guard cells and root systems are known in the art. These ion channels have been found to play important roles in regulating water conservation, nutrient absorption and other plant functions. High throughput identification of molecules that modulate these channels can help to develop agri-chemicals that can help plants withstand unfavorable environmental conditions such as draught or to identify ion channels that can be engineered into plants and expressed to alter their ability to withstand environments such as draught or absorb nutrients.

II An Array of Microfabricated Capillaries Optionally with Electrodes and Methods of Use The present invention also includes a biochip that includes an array of capillaries, wherein members of said array comprises an ion transport measuring structure.

Figure 15:
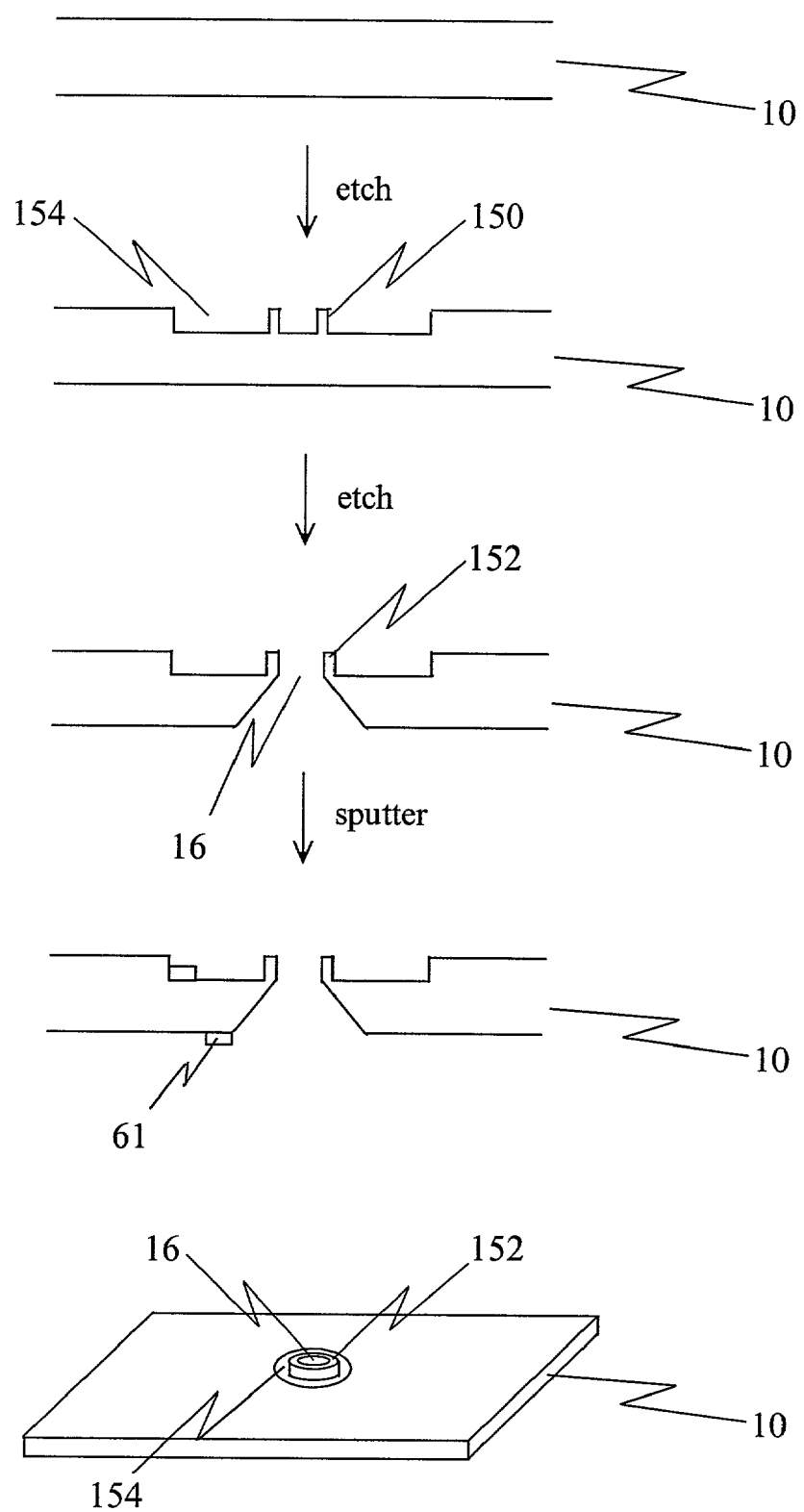
FIG. 15 depicts the manufacture of a capillary of the present invention that can be used as an ion transport detection structure in a manner generally depicted in FIG. 9. The process starts with providing a substrate (10), which is then etched to form protrusions (150) that will form a capillary structure (52). This etching forms a trench (154) that defies the protrusion (150) or capillary (152). Further etching from the other side of the substrate forms a hole (16) that can have a funnel shape. Sputtering of conductive material can be used to provide electrode structures (61) for use in ion transport function or property determinations using methods of the present invention. In one aspect of the present invention, the protrusion (150) can be hollow and be open or closed at the top of the structure.

As depicted in FIG. 15, the present invention can include capillary structures that are useful in the present invention. These capillary structures can be provided in an array on a substrate. The substrate can be of any appropriate size, but preferably, the substrate is between about 1 mm$^2$ and about 2,500 cm$^2$, having a density of capillary structures between about 1 and about 2,500 capillary structures per mm$^2$. The capillary structures can be any appropriate distance apart, but are preferably between about 20 micrometers and about 10 cm apart.

Figure 9:
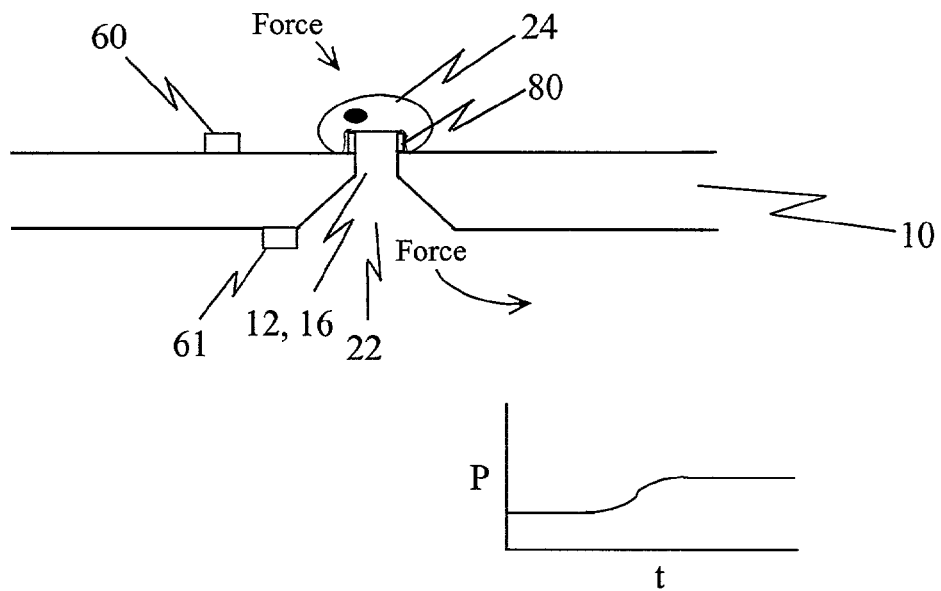
FIG. 9 depicts the operation of the structure depicted in FIG. 8 or FIG. 15.
Figure 9:
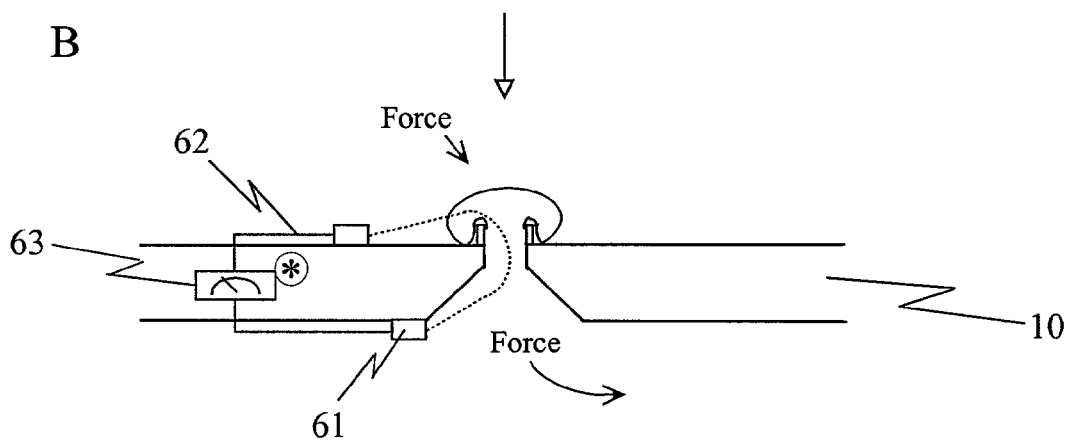
Figure 10:
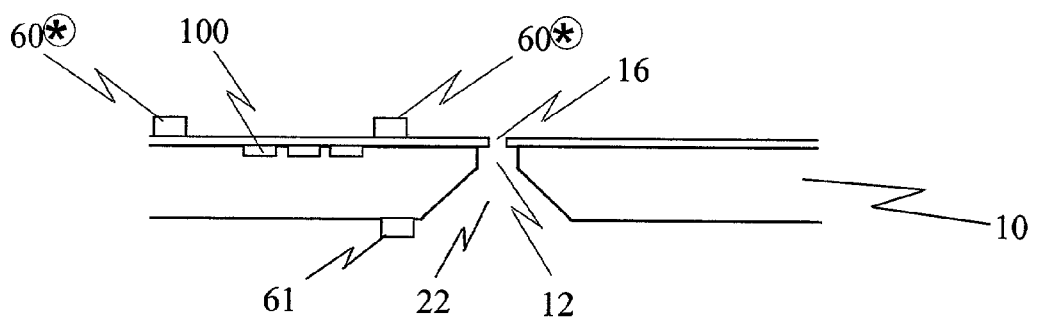
FIG. 10 depicts one preferred aspect of the present invention. In cross section a substrate (10) with a coating (14) is shown with a hole (12) in the substrate and a hole (16) in the coating with a funnel structure (22) and fitted with electrodes (60, 61). Also depicted are particle positioning means (100), which in this case are depicted as traveling wave dielectrophoresis structures (100).
Figure 11:
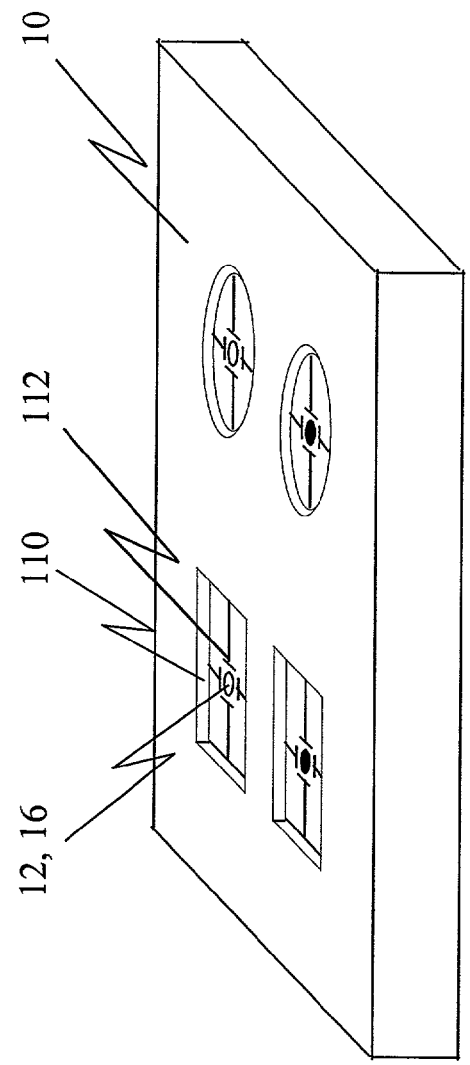
FIG. 11 depicts one aspect of the present invention wherein wells (110) are formed on a substrate (10). The wells can be of any appropriate shape, such as but not limited to the circles and squares depicted. The wells can be made using appropriate methods, such as a machining or etching. The wells preferably, but optionally, include particle positioning means (112). The wells are reminiscent of wells of a microtiter plate, but are preferably much smaller. In this way, a particle or population of particles, such as cells, can be added into the well or wells using introduction or dispensation methods and technologies appropriate for the type of particles being used. Also, appropriate introduction or dispensation methods and technologies can be used to add reagents, such as test reagents, to the wells. Appropriate dispensation methods include piezo dispensers, ink jet technologies, pipetters, micropipetters, electrophoretic dispensations, connected tubings, other microfluidics methods and devices and the like, such as they are known in the art or later developed. For example, the introduction methods could be realized through microfluidic channels in which electroosmotic pumping or pressure driven pumping of the fluid is utilized. A number of examples of traveling wave dielectrophoretic structures are provided herein and in U.S. patent application Ser. No. 09/678,263 and U.S. patent application Ser. No. 09/679,024.
Figure 12:
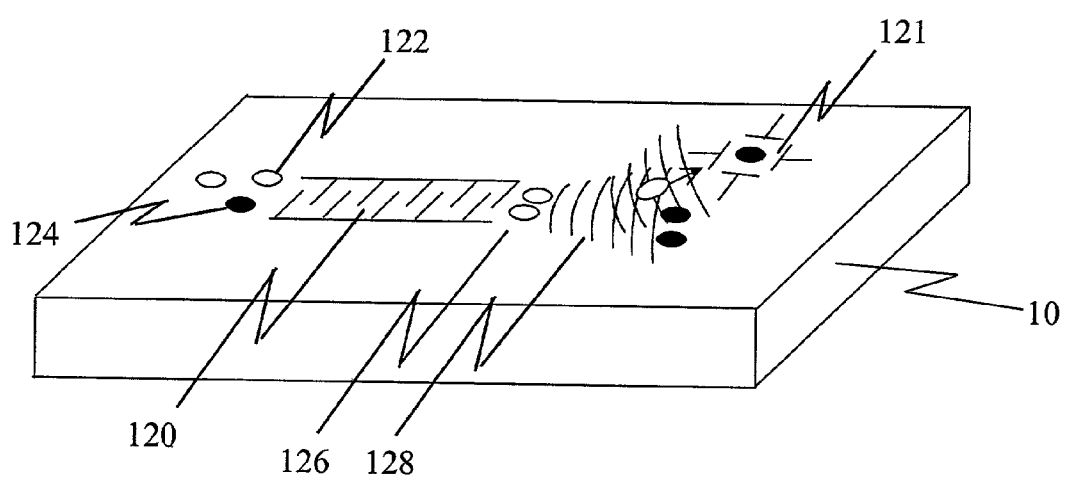
FIG. 12 depicts one preferred aspect of the present invention that includes particle separation structures along with particle positioning means. In this figure, a substrate (10) is fitted with traveling wave dielectrophoretic structure (120) that can separate particles (122, 124) of differing dielectric properties and/or other properties, such as live cells (122) and dead cells (124) which can be visualized using trypan blue exclusion or other viability dyes. The separated cells (126) are subject to one or more particle positioning means, such as a particle switch (128) which can further separate members of a population of cells (122, 124) and direct the desired population of cells to an ion transport measuring means (121). The cell directed to the ion transport measuring means is then engaged therewith for ion transport functional analysis.

FIG. 15 depicts the manufacture of a capillary of the present invention that can be used as an ion transport detection structure in a manner generally depicted in FIG. 9. The process beings with providing a substrate (10), which is then etched to form protrusions (150) that will form a capillary structure (52). This etching forms a trench (154) that defies the protrusion (150) or capillary (152). Further etching from the other side of the substrate forms a hole (16) that can have a funnel shape. Sputtering of conductive material can be used to provide electrode structures (61) for use in ion transport function or property determinations using methods of the present invention.

The present invention also includes a method of detecting ion transport function or property of a particle that includes contacting a sample comprising at least one particle with the biochip that includes capillary structures. Positioning the at least one particle at or near said ion transport measuring means and measuring ion transport function or property of the sample or particle using said ion transport measuring means. This method is generally depicted in FIG. 9.

Figure 7:
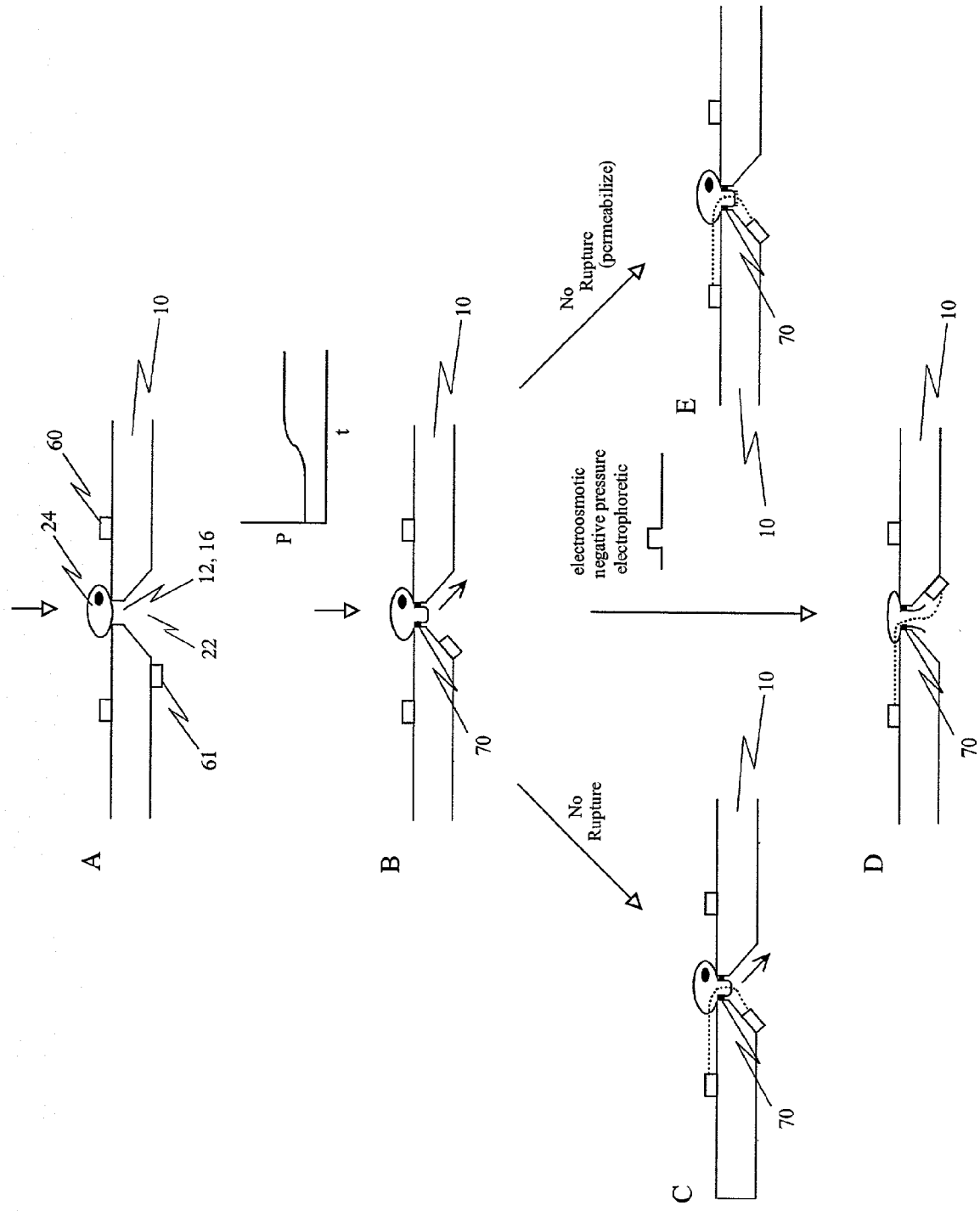
FIG. 7A depicts a process of the present invention wherein a particle (24) such as a cell engages a hole (12, 16) on a biochip of the present invention including a substrate (10) and electrodes (60, 61). The particle (24) has preferably been localized at or near the hole (12, 16) using particle positioning means (not shown). As depicted in FIG. 7B, once engaged, a portion of the particle (24) is moved into the space of the hole (12, 16) using appropriate forces, such as acoustic forces to push the cell (24) into the hole (12, 16) or electroosmotic, electrophoretic or negative pressure to pull the cell (24) into the hole (12, 16). Appropriate structures, such as acoustic structures, electroosmotic structures, electrophoretic structures or negative pressure structures can be provided on or near the biochip or a chamber connected thereto to allow for operations thereof. A good seal (70) between the substrate or coating thereon and the cell is preferable. Depending on the electric parameters being measured, mega ohm or giga ohm sealing between the particle and the hole is preferred.
FIG. 7D depicts the rupturing of the membrane of the cell using a pulse of force, such as negative pressure or positive pressure or electric field pulse. When the electric field pulse over microsecond to millisecond is applied, a strong electric field is applied to the membrane patch in the hole causing the rupture of the membrane. A negative pressure pulse would result in a ruptured membrane as well. The rupturing of the membrane patch allows for direct electrical access to the particle interior (for example cell interior) from the hole (12, 16), and this is called "whole cell configuration" or "whole cell access." In such a case, electrical voltage applied to the recording electrode structures (60, 61) in contact to the two ends of the hole through the measurement solutions introduced into the regions surrounding the biochip (for example above and below the biochip in FIG. 7A) is directly applied to the membrane of the particle, thus applied to the ion transports located in the membrane. After the membrane patch of the particle (24) inside the hole is ruptured, a good seal (70) between the substrate or coating thereon and the particle (for example a cell) is preferably maintained during the measurement of the ion transports. Electrical responses or electrical properties of the ion transports located in the membrane of the particle can be measured or detected by using various recording circuits, which may include a patch clamp amplifier. The recording of the ion transports under the whole cell configuration is typically called "whole cell recording." The good seal, e.g., high resistance seal such as >1 gigaohm, ensures that the electrical current from the ion transports' activity can be accurately measured with only small background leakage current.
FIG. 7C depicts the case in which the membrane patch of the particle (24) located in the hole (12, 16) is not ruptured. In such a case, the ion transport(s) in the membrane patch of the particle located in the hole (12, 16) can be measured. Such measurement provides property information of one or a few ion transport molecules in the membrane patch and is sometimes referred as "cell-attached patch" recording.
FIG. 7E depicts the case in which the membrane patch of the particle (24) located in the hole (12, 16) is not ruptured, but the electrical access of the particle interior is achieved by permeabilizing the membrane patch by using "membrane permeabilization molecules or reagents." In this way, the pores (as alternate pathways for the movement of ions and electrons) are formed in the membrane patch and electrical voltages can also be applied to the ion transports on the membrane of the particle (other than those in the membrane patch), and electrical recording of the ion transports can be performed in a similar fashion to that for FIG. 7D.
Figure 8:
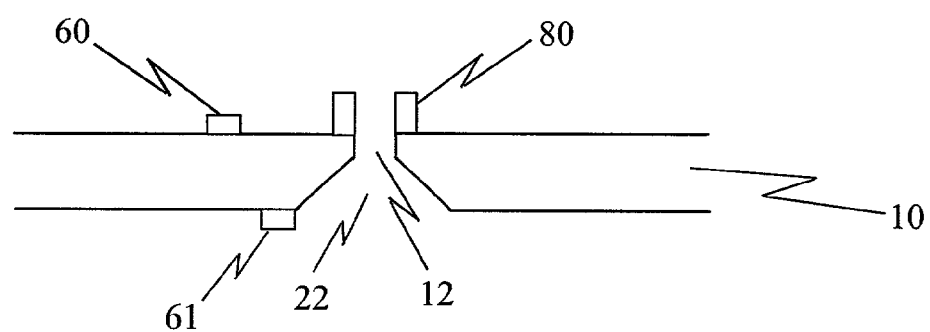
FIG. 8 depicts a structure of the present invention that includes protrusions or wires (80) that can be singular, partially circumnavigate or circumnavigate with regard to the hole (12, 16). The use of these structures is depicted in FIG. 9.

FIG. 9 depicts the operation of the structure depicted in FIG. 15. In FIG. 9A, a particle (24) such as a cell, is engaged with the capillary structure. This is preferably accomplished by applying a positive or negative force, such as depicted in FIG. 7. The particle, such as a cell, is ruptured, such as through a pulse of force, to form a patch clamp. The electrical connection leads (62) from the electrodes (60, 61) connect to a measuring device (63) that can monitor and optionally record the electric properties in the circuit completed as depicted by the dashed line. Optionally, other ion transport function or property determinations can be made using this structure. For example, whole cell determinations, patch clamp determinations, voltage gated determinations and ligand gated determinations and other ion transport assay methods described herein can also be made.

III An Array of Microfabricated Needle Electrodes on a Biochip and Methods of Use The present invention also provides a biochip that includes an array of needle electrodes wherein members of said array comprise an ion transport measuring means. The biochip can provide needle electrodes that are associated with a capillary or a hole on said biochip. In the alternative, the needle electrodes can penetrate a particle. The particle is preferably a cell or vesicle.

As depicted in FIG. 8, FIG. 9, FIG. 16A and FIG. 16B, the present invention can include needle electrode structures that are useful in the present invention. These needle electrode structures can be provided in an array on a substrate. The substrate can be of any appropriate size, but preferably, the substrate is between about 1 mm$^2$ and about 2,500 cm$^2$, having a density of needle electrodes between about 1 and about 2,500 needle electrodes per mm$^2$. The needle electrodes can be any appropriate distance apart, but are preferably between about 20 micrometers and about 10 cm apart.

Figure 16A:
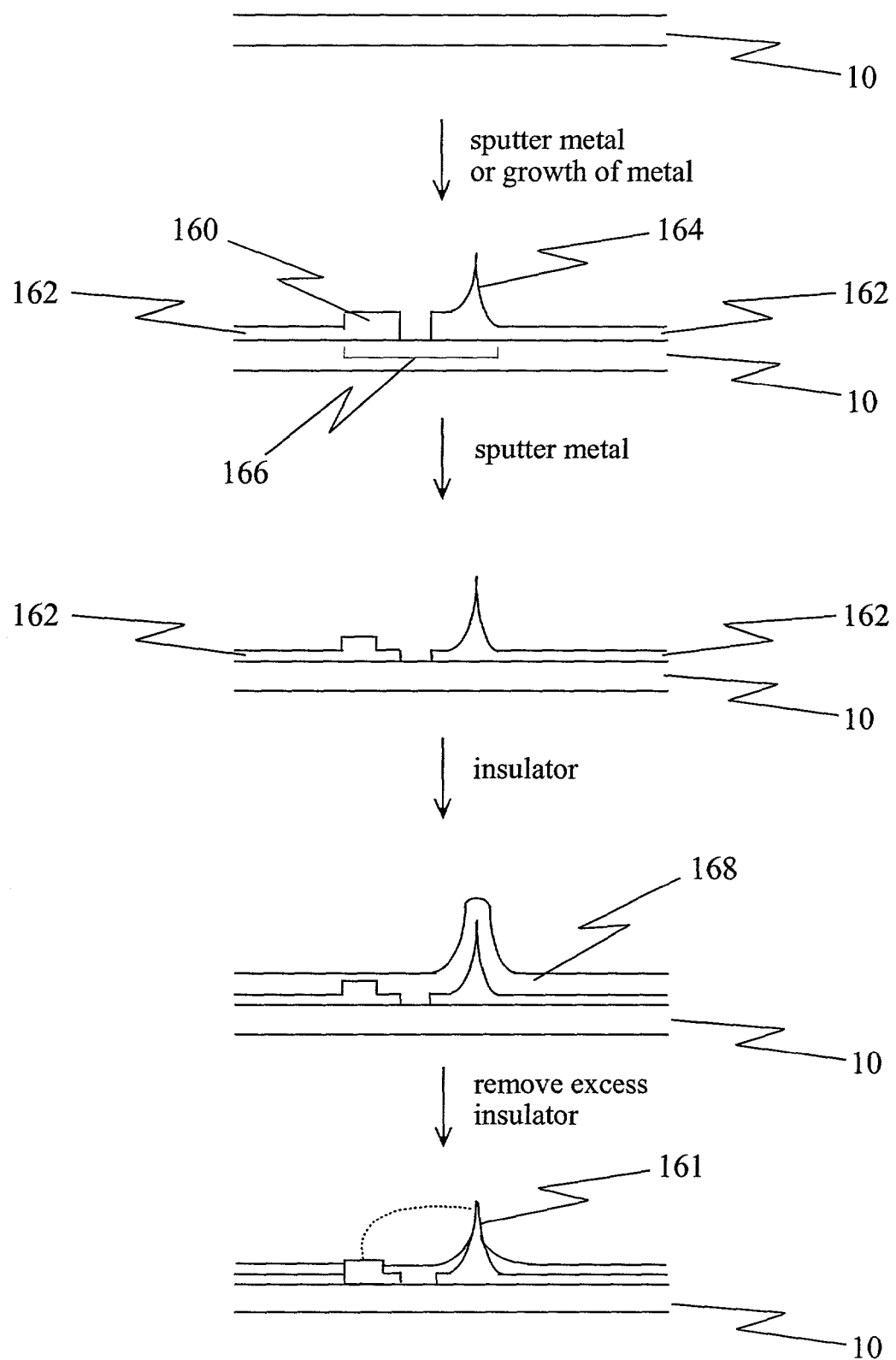
FIG. 16A depicts the manufacture of such a structure. A substrate (10) is provided, upon which a conductive material (160) is provided using, for example, sputtering, chemical growth, electrochemical growth or other growth methods. The conductive material provides an electrode portion (166) operably connected to a needle structure (164). Optionally, a button (162) of conductive material can be added to the electrode portion (166) via sputtering. An insulating material (168) such as resist (for example, PUMS) is then added over the conductive material (160) via sputtering, evaporation or other appropriate methods. Photolithographic methods and other patterning techniques can be used for these procedures. Excess insulating material is then removed by appropriate methods such as masked etching which results in a needle structure of the present invention (161). Electrical measurements can be made between the electrode portion (166) and the needle structure (164) as depicted by dashed lines. The needle structure can be connected to electrical connection leads (162) using appropriate methods, such as sputtering of conductive material at appropriate times during the manufacture of the device. Those skilled in microfabrication can choose appropriate protocols and materials for making these devices.

FIG. 16A depicts the manufacture of such a structure. A substrate (10) is provided, upon which a conductive material (160) is provided using sputtering. The conductive material provides an electrode portion (166) operably connected to a needle structure (164). Optionally, a button (162) of conductive material can be added to the electrode portion (166) via sputtering. An insulating material (168) such as resist is then added over the conductive material (160) via appropriate methods. Excess insulating material is then removed by appropriate methods such as masked etching which results in a needle structure of the present invention (161). Electrical measurements can be made between the electrode portion (166) and the needle structure (164) as depicted by dashed lines. The needle structure can be connected to electrical connection leads (162) using appropriate methods, such as sputtering of conductive material at appropriate times during the manufacture of the device.

The present invention also includes a method of detecting ion transport function or property of a particle that includes contacting a sample comprising at least one particle with the biochip that includes needle electrode structures such as in an array. Positioning the at least one particle at or near said ion transport measuring means and measuring ion transport function or property of the sample or particle using said ion transport measuring means. This method is generally depicted in FIG. 16B.

Figure 16B:
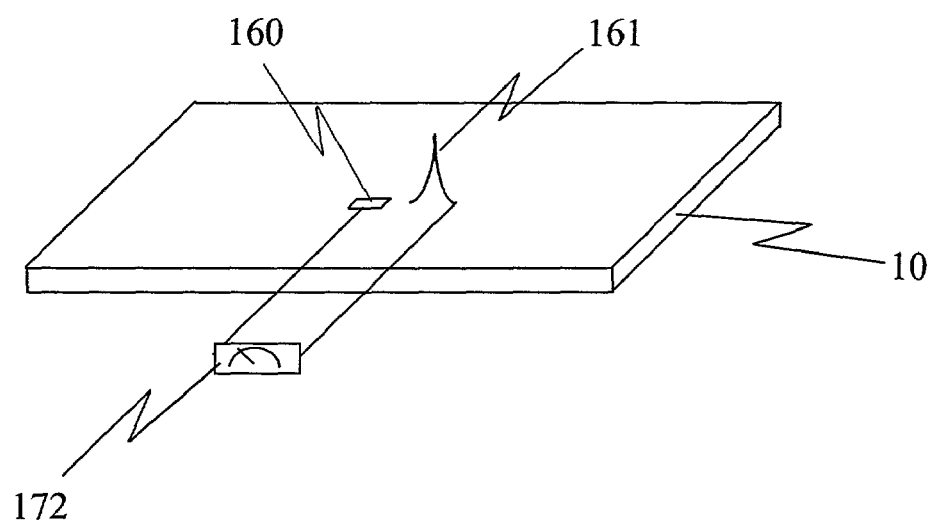
FIG. 16B and FIG. 16C depict the use of the device of FIG. 16A in an ion transport function or property determination. As depicted in FIG. 16C, the needle structure (161) is contacted with a sample including a particle (24) such as a cell. The cell is positioned at or near the needle structure such as by horizontal positioning structures (not depicted). The particle is then impaled upon the needle structure such as by vertical positioning structures (not depicted). As depicted in FIG. 16A, the needle structure has a conductive tip and an insulator surface covering the rest part of the needle structure. When the particle is impaled upon the needle structure, the conductive tip of the needle structure is fully inside the particle interior so that the needle structure engages the particle surface (for example cell membrane) at the insulator-covered regions of the needle structure. The electric seal between the particle and the needle structure can be enhanced using specific binding members at a location corresponding to the juncture of the particle with the needle structure. As depicted in FIGS. 16B and 16C, ion transport function or property determinations can be made using methods of the present invention by measuring the electrical properties between the electrode portion (162) and the needle structure (161) as depicted by the dashed line which completes the depicted circuit that includes an electrical measuring device (172) and an electrical source (174). Specific patterning methods such as photolithography can be used for producing electrode structures (160) at locations on the substrate.
Figure 16C:
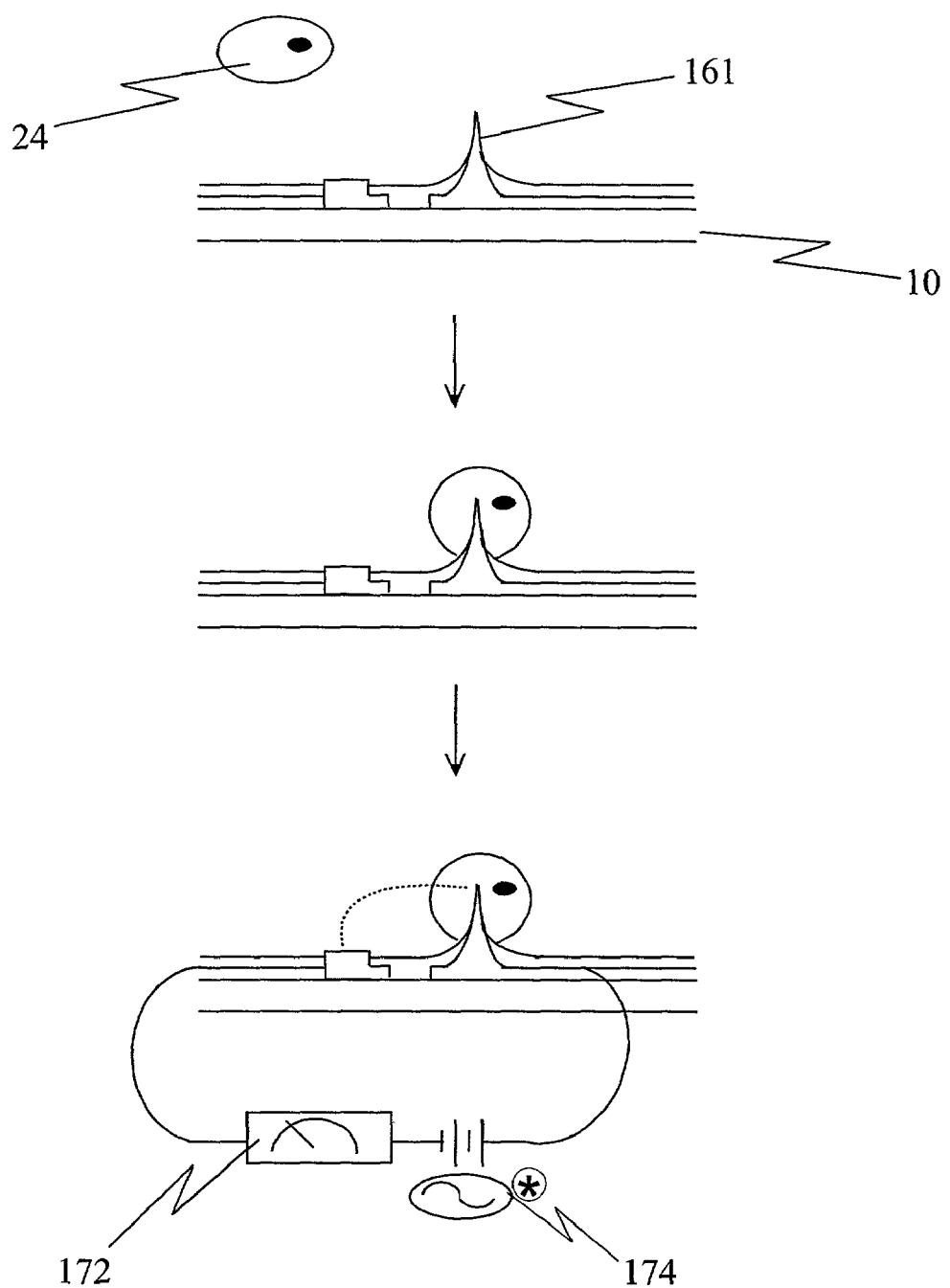

FIG. 16B depicts the use of the device of FIG. 16A in an ion transport function or property determination. The needle structure (170) is contacted with a sample including a particle (24) such as a cell. The cell is positioned at or near the needle structure such as by horizontal positioning structures (not depicted). The particle is then impaled upon the needle structure such as by vertical positioning structures (not depicted). The electric seal between the particle and the needle structure can be enhanced using specific binding members at a location corresponding to the juncture of the particle with the needle structure. Ion transport function or property determinations can be made using methods of the present invention by measuring the electrical properties between the electrode portion and the needle structure as depicted by the dashed line which completes the depicted circuit that includes an electrical measuring device (172) and an electrical source (174).

Various specific ion transport assay methods can be used for determining ion transport function or properties. These include but are not limited to patch clamp recording, whole cell recording, perforated patch or whole cell recording, whole cell recording, vesicle recording, outside out or inside out recording, single channel recording, artificial membrane channel recording, voltage gated ion transport recording, ligand gated ion transport recording, energy requiring ion transporters (such as ATP), non energy requiring transporters, toxins such a scorpion toxins, viruses, ligand perfusion, stretch gated (fluid flow or osmotic) and the like. See, generally Neher and Sakman, Scientific American 266:44-51 (1992); Sakman and Neher, Ann. Rev. Physiol. 46:455-472 (1984); Cahalan and Neher, Methods in Enzymology 207:3-14 (1992); Levis and Rae, Methods in Enzymology 207:14-66 (1992); Armstrong and Gilly, Methods in Enzymology 207:100-122 (1992); Heinmann and Conti, Methods in Enzymology 207:131-148 (1992); Bean, Methods in Enzymology 207:181-193 (1992); Leim et al., Neurosurgery 36:382-392 (1995); Lester, Ann. Rev. Physiol 53:477-496 (1991); Hamill and McBride, Ann. Rev. Physiol 59:621-631 (1997); Bustamante and Varranda, Brazilian Journal 31:333-354 (1998); Martinez-Pardon and Ferrus, Current Topics in Developmental Biol. 36:303-312 (1998); Herness, Physiology and Behavior 69:17-27 (2000); Aston-Jones and Siggins, www.acnp.org/GA/GN40100005/CH005.html (Feb. 8, 2001); U.S. Pat. Nos. 6,117,291; 6,107,066; 5,840,041 and 5,661,035; Boulton et al., Patch-Clamp Applications and Protocols, Neuromethods V. 26 (1995), Humana Press, New Jersey; Ashcroft, Ion Channels and Disease, Cannelopathies, Academic Press, San Diego (2000); Sakman and Neher, Single Channel Recording, second edition, Plenuim Press, New York (1995) and Soria and Cena, Ion Channel Pharmacology, Oxford University Press, New York (1998), each of which is incorporated by reference herein in their entirety.

IV. An Array of Microfabricated Holes on a Biochip and Method of Use

The present invention also includes a biochip that includes an array of holes, wherein members of the array comprise an ion transport measuring means. The particle is preferably a cell or vesicle, but that need not be the case. The ion transport measuring means can be any described herein, such as but not limited to patch clamp detection structures and whole cell detection structures. As depicted in FIG. 1, FIG. 2, and FIG. 5, the present invention can include holes that are useful in the present invention. These holes can be provided in an array on a substrate. The substrate can be of any appropriate size, but preferably, the substrate is between about 1 $mm^2$ and about 2,500 $cm^2$, having a density of holes between about 1 and about 2,500 holes per $mm^2$. The holes can be any appropriate distance apart, but are preferably between about 20 micrometers and about 10 cm apart.

FIG. 1 depicts one aspect of a biochip of the present invention. A substrate (10) made of appropriate material, such as fused silica, glass, silica, $SiO_2$, silicon, plastics, polymers or a combination or combinations thereof can define holes (12) that form at least in part ion transport measuring means of the present invention. Optionally, a coating (14) such as a polymer coating can be placed on top of the surface of the substrate. The coating can include functional groups to aid in the localization and immobilization particles at or near the holes (12). Such functional groups can include, for example, specific binding members that can facilitate such localization or immobilization of particles. The coating can also define holes (16) that can functionally engage the holes (16) defined by the substrate (10). In one aspect of the present invention, such holes (12) in the coating (14) are preferable because the accuracy and precision for machining or molding such holes in the coating is better suited for the coating (14) rather than the substrate (10). For example, it is more efficient, accurate and precise to manufacture holes in the thin coating (14) rather than the relatively thick substrate (10). This is particularly true when the coating (14) is made of polymers whereas the substrate (10) is made of harder materials that may be less suitable for machining, etching or molding, such as silica. FIG. 1A depicts a biochip of the present invention optionally with a coating. FIG. 1B depicts a cross section of FIG. 1A along A-A showing the coating in place.

FIG. 2 depicts different configurations of substrates (10) and coatings (14) to form holes in the substrate (12) and holes in the coating (16). FIG. 2A depicts the biochip of FIG. 1A with a cell (22) engaged thereto. FIG. 2B depicts a substrate (10) with a coating (14), wherein the substrate has been machined or etched to form a funnel shaped structure (20) continuous with a hole in the substrate (10). This funnel shaped structure (20) allows for less rigorous manufacturing parameters as compared to the straight walled holes (12) depicted in FIG. 2A. A cell (24) is depicted engaged on the structure of FIG. 2B. FIG. 2C depicts the structure of FIG. 2B inverted with a cell (24) engaged thereto. FIG. 2D depicts a structure having a double funnel structure (20, 22) that defines a hole (12) in the substrate (10). Although holes of particular shapes and dimensions are depicted, the holes can be of any appropriate shape or dimensions.

Shapes of holes can be geometric or non-geometric, such as circular, oval, square, triangular, pentagonal, hexagonal, heptagonal, octagonal or the like. Non-geometrical shapes such as kidney bead or other shapes are also appropriate. Geometric shapes can have the advantage of allowing higher density packing of holes, such as in a honey-comb configuration. The diameter or cross section of the holes at the portion where a particle is contacted can be any appropriate size, but is preferably between about 0.1 micrometer and about 100 micrometers, more preferably between about 1 micrometer and about 10 micrometers.

FIG. 5 depicts a structure such as depicted in FIG. 2B including a substrate (10) that defines a hole (12) with a funnel structure (22). FIG. 5A depicts such a structure with a coating (50) over all surfaces. The coating can be made of appropriate materials, such as polymers or functional coatings that can allow for immobilization of materials such as biological moieties or chemical moieties. The coating can also include binding members, such as specific binding members, such as antibodies, that can facilitate the localization or immobilization of particles such as cells at or near the hole (12). In one aspect of the present invention, the coating is made of a polymer that has the characteristic of changing size with temperature. By increasing in size, the polymer can promote the formation of an efficient seal between a particle (24) such as a cell and the hole. In FIG. 5B the coating (52) is depicted as being localized to an area in close proximity to the hole (12) in the substrate. In one aspect of the present invention, the coating in this configuration includes specific binding members present on particles such as cells. In FIG. 5C the coating is depicted as being localized to the hole (12) and optionally surrounding areas. This configuration can promote a strong seal between the cell and the hole (12). In one aspect of the present invention, the substrate (10) is made of silicon. The substrate (10) is then heated to make a structure that includes the substrate (10) of silicon and a coating (50) of silicon dioxide.

The present invention also includes a method of detecting ion transport function or property of a particle, including contacting a sample comprising at least one particle with a biochip including an array of holes, positioning the at least one particle at or near said ion transport measuring means; and measuring ion transport function or property of the particles or sample using said ion transport measuring means. This method is generally depicted in FIG. 6 and FIG. 7.

FIG. 6A depicts electrode structures (60, 61) present on either side of a hole (12,16) defined by a substrate (12) and depicted as including a funnel structure (24). The electrodes are positioned as to be on either side of particle, such as a cell (24). Electrical connection leads (62) connect the electrodes (60, 61) to a measuring device (63) that can measure and optionally record the electrical properties of the particle depicted by the dashed line, such as, for examples, electric current through the ion transports in the particle membrane under applied voltage conditions or the cell membrane potential under fixed current flow through the ion transports in the membrane. Measuring device (63) can be conventional electrophysiology measurement apparatus, such as described by Axon Corporation. Various ion transport assay methods can be achieved with these or other electrophysiology apparatuses. FIG. 6B depicts a variety of electrode structures as viewed from the top of FIG. 6A. In one aspect of the present invention, the electrode (60) can have any appropriate shape, such as square, circular or semi-circular. The electrode is preferably operably linked to at least one electrical connection lead (62). In one aspect of the present invention, there can be several electrodes, preferably independently attached to separate electrodes so as to be independently addressable, that are different distances from a hole (12, 16). Depending on the conditions of a particular method or the electrical parameter being measured, such as voltage or current, electrodes of different shape, size or geometries can be utilized. Although FIG. 6B is viewed from the top of FIG. 6A, similar structures can be provided as electrode (61) as viewed from the bottom of FIG. 6B. The electrode (61) can be provided in or outside of the funnel structure (22) when present.

FIG. 7A depicts a process of the present invention wherein a particle (24) such as a cell engages a hole (12, 16) on a biochip of the present invention including a substrate (10) and electrodes (60, 61). The particle (24) has preferably been localized at or near the hole (12,16) using particle positioning means (not shown). As depicted in FIG. 7B, once engaged, a portion of the particle (24) is moved into the space of the hole (12, 16) using appropriate forces, such as acoustic forces to push the cell (24) into the hole (12, 16) or electroosmotic, electrophoretic or negative pressure to pull the cell (24) into the hole (12, 16). Appropriate structures, such as acoustic structures, electroosmotic structures, electrophoretic structures or negative pressure structures can be provided on or near the biochip or a chamber connected thereto to allow for operation thereof. A good seal (70) between the substrate or coating thereon and the cell is preferable. Depending on the electric parameter being measured, mega ohm or giga ohm sealing between the particle and the hole is preferred. FIG. 7C depicts the rupturing of the membrane of the cell using a pulse of force, such as negative pressure or electric field pulse. When the electric filed pulse is applied, a strong electric filed is applied to the membrane patch in the hole causing rupture of the membrane. A negative pressure pulse would result in a ruptured membrane as well. A good seal (70) between the substrate or coating thereon and the cell is preferable.

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

What is claimed is:

1. A biochip system comprising:
   a) a biochip comprising at least two horizontal fluidic channels;
   b) an ion transport measuring means that comprises a vertical hole through said biochip in fluid communication with said horizontal fluidic channels; and
   c) at least one horizontal particle positioning means comprising a pressure generation structure;
   wherein said horizontal particle positioning means positions a particle or a population of particles relative to the X-Y coordinates of said biochip at or near said vertical hole.

2. The biochip system of claim 1, wherein said pressure generation structure comprises at least one syringe.

3. The biochip system of claim 1, wherein said pressure generation structure comprises at least one pump.

4. The biochip system of claim 1, wherein said pressure generation structure is not part of said ion transport measuring means.

5. The biochip system of claim 1, wherein said particle is a cell.

6. The biochip system of claim 1, wherein said population of particles is a population of cells.

7. The biochip system of claim 1, further comprising a vertical positioning means.

8. The biochip system of claim 1, wherein said horizontal particle positioning means positions a single cell at or near a single vertical hole through the biochip, said vertical hole having an opening between about 0.1 micrometers and 100 micrometers in diameter.

9. The biochip system of claim 8, wherein said horizontal particle positioning means positions a single cell inside a single vertical well.

10. The biochip system of claim 1, wherein said horizontal particle positioning means positions a single particle at or near a single vertical hole through the biochip, said vertical hole having an opening between about 0.1 micrometers and 100 micrometers in diameter.

11. The biochip system of claim 10, wherein said horizontal particle positioning means positions a single particle inside a single vertical well.

12. The biochip system of claim 1, wherein said ion transport measuring means comprises a structure for whole cell recording or single channel recording or a combination thereof.

13. The biochip system of claim 1, wherein said horizontal particle positioning means comprises a horizontal capillary.

14. The biochip system of claim 13, wherein said horizontal particle positioning means comprises a hole that extends through said horizontal capillary.

15. The biochip system of claim 1, wherein said ion transport measuring means comprises at least one recording electrode.

16. The biochip system of claim 1, wherein said ion transport measuring means comprises at least one needle electrode.

17. The biochip system of claim 1, further comprising an additional particle manipulation means.

18. The biochip system of claim 1, wherein at least one of said horizontal fluidic channels comprises a horizontal capillary.

19. The biochip system of claim 18, wherein the horizontal capillary is created in situ by microfabrication methods.

20. The biochip system of claim 1, wherein at least one of said horizontal fluidic channels when in combination with external fluidic devices is used for delivering intracellular solutions, extracellular solutions, cell suspensions, or compound solutions or a combination thereof to the ion transport measuring means.

21. The biochip system of claim 20, wherein said at least one horizontal fluidic channel comprises a horizontal capillary.

22. A device for detecting ion transport activity of a particle, comprising: the biochip system of claim 1, at least two fluidic compartments separated by the biochip and operably connected by said vertical hole through said biochip, and at least one fluidic inlet and at least one outlet for one or more of said at least two fluidic compartments.

23. The device of claim 22, wherein said device comprises a material selected from the group consisting of glass, plastics, elastomers, ceramics, and quartz.

24. The device of claim 22, further comprising:
a plurality of vertical holes through said biochip; and a plurality of fluidic compartments located on two sides of said biochip, wherein each of said vertical holes through said biochip is connected to two fluidic compartments.

25. The device of claim 22, further comprising horizontal fluidic channels for delivering particle suspensions, compound solutions or both to said at least two fluidic compartments.

26. The device of claim 22, further comprising a means for connecting a measuring device to said at least two fluidic compartments.

27. The biochip system of claim 1, wherein the vertical hole through the biochip has an opening between about 0.1 micrometers and 100 micrometers in diameter.

28. The biochip system of claim 1, wherein the biochip comprises a coating.

29. The biochip system of claim 1, wherein the biochip comprises an additional built-in particle positioning means comprising an acoustic structure.

30. The biochip system of claim 1, further comprising at least one structure selected from the group consisting of: a dielectric focusing structure, a quadrupole electrode structure, an electrorotation structure, a traveling wave dielectrophoresis structure, a concentric circular electrode structure, a spiral electrode structure, a square spiral electrode structure, a particle switch structure, an electromagnetic structure, a DC electric field-induced fluid motion structure, an AC electric field induced fluid motion structure, an electrophoretic structure, an electroosmosis structure, an acoustic structure and a negative pressure structure,
wherein at least one of said structures is integrated into said biochip.

31. The biochip system of claim 1, wherein the biochip further comprises a substrate with at least one micro-electromagnetic unit fabricated on the substrate.

32. The biochip system of claim 1, which comprises a plurality of ion transport measuring means, and each of said ion transport measuring means comprises a vertical hole through said biochip.

* * * * *